(12) United States Patent
Czekai et al.

(10) Patent No.: US 12,246,026 B2
(45) Date of Patent: *Mar. 11, 2025

(54) GANAXOLONE FOR USE IN TREATMENT OF STATUS EPILEPTICUS

(71) Applicant: Marinus Pharmaceuticals, Inc., Radnor, PA (US)

(72) Inventors: David Czekai, Radnor, PA (US); Maciej Gasior, Radnor, PA (US); Lorianne Masuoka, Radnor, PA (US); Julia Tsai, Radnor, PA (US); Joseph Hulihan, Radnor, PA (US); Alex Aimetti, Radnor, PA (US)

(73) Assignee: Marinus Pharmaceuticals, Inc., Radnor, PA (US)

(*) Notice: Subject to any disclaimer, the term of this patent is extended or adjusted under 35 U.S.C. 154(b) by 296 days.

This patent is subject to a terminal disclaimer.

(21) Appl. No.: 17/393,566

(22) Filed: Aug. 4, 2021

(65) Prior Publication Data

US 2022/0202831 A1 Jun. 30, 2022

Related U.S. Application Data

(63) Continuation of application No. 17/186,569, filed on Feb. 26, 2021, now Pat. No. 11,110,100, which is a continuation of application No. PCT/US2020/044843, filed on Aug. 4, 2020.

(60) Provisional application No. 62/882,648, filed on Aug. 5, 2019.

(51) Int. Cl.
*A61K 31/573* (2006.01)
*A61K 9/00* (2006.01)
*A61P 25/08* (2006.01)

(52) U.S. Cl.
CPC .......... *A61K 31/573* (2013.01); *A61K 9/0019* (2013.01); *A61P 25/08* (2018.01)

(58) Field of Classification Search
CPC ............................. A61K 9/0019; A61P 25/08
See application file for complete search history.

(56) References Cited

U.S. PATENT DOCUMENTS

| | | | |
|---|---|---|---|
| 2,671,750 | A | 3/1954 | Macek |
| 4,540,602 | A | 9/1985 | Motoyama et al. |
| 4,783,484 | A | 11/1988 | Violante et al. |
| 4,826,689 | A | 5/1989 | Violanto et al. |
| 4,997,454 | A | 3/1991 | Violante et al. |

(Continued)

FOREIGN PATENT DOCUMENTS

| | | |
|---|---|---|
| CA | 2541811 C | 4/2005 |
| CA | 2892811 A1 | 6/2014 |

(Continued)

OTHER PUBLICATIONS

International Search Report and Written Opinion in PCT/US2020/044843, dated Nov. 18, 2020.

(Continued)

*Primary Examiner* — Carlos A Azpuru
(74) *Attorney, Agent, or Firm* — Hogan Lovells US LLP

(57) ABSTRACT

This invention relates to methods for treating status epilepticus by administering to the subject in need thereof an intravenous bolus of ganaxolone and a continuous intravenous infusion of a neurosteroid. The method provides SE suppression and continued suppression of SE.

26 Claims, 16 Drawing Sheets

(56) References Cited

U.S. PATENT DOCUMENTS

| | | |
|---|---|---|
| 5,134,127 A | 7/1992 | Stella et al. |
| 5,145,684 A | 9/1992 | Liversidge et al. |
| 5,209,746 A | 5/1993 | Balahan et al. |
| 5,213,808 A | 5/1993 | Bar-Shalom et al. |
| 5,221,278 A | 6/1993 | Linkwitz et al. |
| 5,260,068 A | 11/1993 | Chen |
| 5,260,069 A | 11/1993 | Chen |
| 5,298,262 A | 3/1994 | Na et al. |
| 5,299,131 A | 3/1994 | Haas et al. |
| 5,312,390 A | 5/1994 | Wong |
| 5,318,588 A | 6/1994 | Horzewski et al. |
| 5,340,590 A | 8/1994 | Wong et al. |
| 5,346,702 A | 9/1994 | Na et al. |
| 5,352,459 A | 10/1994 | Hollister et al. |
| 5,356,476 A | 10/1994 | Oshlack et al. |
| 5,376,645 A | 12/1994 | Stella et al. |
| 5,391,381 A | 2/1995 | Wong et al. |
| 5,399,363 A | 3/1995 | Liversidge et al. |
| 5,429,824 A | 7/1995 | June |
| 5,445,829 A | 8/1995 | Paradissis et al. |
| 5,456,679 A | 10/1995 | Balaban et al. |
| 5,470,583 A | 11/1995 | Na et al. |
| 5,472,708 A | 12/1995 | Chen |
| 5,494,683 A | 2/1996 | Liversidge et al. |
| 5,508,040 A | 4/1996 | Chen |
| 5,510,118 A | 4/1996 | Bosch et al. |
| 5,518,187 A | 5/1996 | Bruno et al. |
| 5,534,270 A | 7/1996 | De Castro |
| 5,543,133 A | 8/1996 | Swanson |
| 5,560,932 A | 10/1996 | Bagchi et al. |
| 5,573,783 A | 11/1996 | Desieno et al. |
| 5,629,277 A | 5/1997 | Plishka |
| 5,662,883 A | 9/1997 | Bagchi et al. |
| 5,665,331 A | 9/1997 | Bagchi et al. |
| 5,672,360 A | 9/1997 | Sackler et al. |
| 5,718,388 A | 2/1998 | Czekai et al. |
| 5,741,522 A | 4/1998 | Violante et al. |
| 5,776,496 A | 7/1998 | Violante et al. |
| 5,840,329 A | 11/1998 | Bai |
| 5,862,999 A | 11/1999 | Czekai et al. |
| 5,980,508 A | 11/1999 | Cardanibe et al. |
| 6,039,979 A | 3/2000 | Gendrot et al. |
| 6,161,536 A | 12/2000 | Redmon et al. |
| 6,214,379 B1 | 4/2001 | Hermelin |
| 6,228,398 B1 | 5/2001 | Devane et al. |
| 6,248,363 B1 | 6/2001 | Patel et al. |
| 6,264,922 B1 | 7/2001 | Wood et al. |
| 6,267,989 B1 | 7/2001 | Liversidge et al. |
| 6,316,029 B1 | 11/2001 | Jain et al. |
| 6,375,986 B1 | 4/2002 | Ryde et al. |
| 6,423,746 B1 | 7/2002 | Yarbrough et al. |
| 6,428,814 B1 | 8/2002 | Bosch |
| 6,432,381 B2 | 8/2002 | Liversidge et al. |
| 6,514,518 B2 | 2/2003 | Monkhouse et al. |
| 6,569,463 B2 | 5/2003 | Patel et al. |
| 6,592,903 B2 | 7/2003 | Ryde et al. |
| 6,607,751 B1 | 8/2003 | Odidi et al. |
| 6,627,223 B2 | 9/2003 | Percel et al. |
| 6,682,759 B2 | 1/2004 | Lim et al. |
| 6,689,378 B1 | 2/2004 | Sun et al. |
| 6,730,325 B2 | 5/2004 | Devane et al. |
| 6,793,936 B2 | 9/2004 | Devane et al. |
| 6,902,742 B2 | 6/2005 | Devane et al. |
| 6,908,626 B2 | 6/2005 | Cooper et al. |
| 6,923,988 B2 | 8/2005 | Patel et al. |
| 6,969,529 B2 | 11/2005 | Bosch |
| 6,976,647 B2 | 12/2005 | Reed et al. |
| 7,078,057 B2 | 7/2006 | Kerkhof |
| 7,198,795 B2 | 4/2007 | Cooper et al. |
| 7,550,445 B2 | 6/2009 | Nerurkar et al. |
| 7,842,232 B2 | 11/2010 | Bosch |
| 7,858,609 B2 | 12/2010 | Shaw et al. |
| 8,022,054 B2 | 9/2011 | Shaw et al. |
| 8,252,228 B1 | 8/2012 | Freeman et al. |
| 8,318,714 B2 | 11/2012 | Shaw et al. |
| 8,362,286 B2 | 1/2013 | Shaw et al. |
| 8,367,651 B2 | 2/2013 | Shaw et al. |
| 8,455,002 B2 | 6/2013 | Shaw et al. |
| 8,604,011 B2 | 12/2013 | Mellon |
| 8,618,087 B2 | 12/2013 | Shaw et al. |
| 8,658,692 B2 | 2/2014 | Kim et al. |
| 8,697,678 B2 | 4/2014 | Goodchild et al. |
| 8,975,245 B2 | 3/2015 | Goodchild et al. |
| 9,017,728 B2 | 4/2015 | Shaw et al. |
| 9,029,355 B2 | 5/2015 | Shaw et al. |
| 9,056,116 B2 | 6/2015 | Shaw et al. |
| 9,452,176 B2 | 9/2016 | Shaw et al. |
| 11,110,100 B2 * | 9/2021 | Czekai ............... A61K 9/0019 |
| 11,395,817 B2 | 7/2022 | During |
| 2002/0012675 A1 | 1/2002 | Jain et al. |
| 2002/0150616 A1 | 10/2002 | Vandercruys |
| 2003/0054042 A1 | 3/2003 | Liversidge et al. |
| 2003/0129242 A1 | 7/2003 | Bosch et al. |
| 2003/0215502 A1 | 11/2003 | Pruss et al. |
| 2004/0067251 A1 | 4/2004 | Johnston et al. |
| 2004/0105778 A1 | 6/2004 | Lee et al. |
| 2004/0105889 A1 | 6/2004 | Ryde et al. |
| 2004/0214746 A1 | 10/2004 | Bosch et al. |
| 2004/0224020 A1 | 11/2004 | Schoenhard |
| 2004/0258757 A1 | 12/2004 | Bosch et al. |
| 2005/0031691 A1 | 2/2005 | McQurk et al. |
| 2005/0118268 A1 | 6/2005 | Percel et al. |
| 2005/0181050 A1 | 8/2005 | Hirsch et al. |
| 2005/0196416 A1 | 9/2005 | Kipp et al. |
| 2005/0226927 A1 | 10/2005 | Han et al. |
| 2005/0232890 A1 | 10/2005 | Hoath et al. |
| 2006/0003005 A1 | 1/2006 | Cao et al. |
| 2006/0216353 A1 | 9/2006 | Liversidge et al. |
| 2007/0141161 A1 | 6/2007 | Shaw et al. |
| 2007/0148252 A1 | 6/2007 | Shaw et al. |
| 2009/0004262 A1 | 1/2009 | Shaw et al. |
| 2011/0236487 A1 | 9/2011 | Shaw et al. |
| 2011/0306579 A1 | 12/2011 | Stein |
| 2012/0052098 A1 | 3/2012 | Shaw et al. |
| 2014/0057885 A1 | 2/2014 | Reddy et al. |
| 2014/0066417 A1 | 3/2014 | Goodchild et al. |
| 2014/0235600 A1 | 8/2014 | Covey et al. |
| 2014/0249120 A1 | 9/2014 | Covey et al. |
| 2015/0018327 A1 | 1/2015 | Reddy |
| 2015/0158903 A1 | 6/2015 | Upasani et al. |
| 2015/0175651 A1 | 6/2015 | Salituro et al. |
| 2015/0291654 A1 | 10/2015 | Upasani et al. |
| 2015/0315230 A1 | 11/2015 | Covey et al. |
| 2015/0335659 A1 | 11/2015 | Jones et al. |
| 2016/0228454 A1 * | 8/2016 | Zhang .................... A61P 25/08 |
| 2017/0202855 A1 | 7/2017 | Shaw et al. |
| 2017/0246188 A1 | 8/2017 | Reddy |
| 2017/0258812 A1 | 9/2017 | Zhang et al. |
| 2018/0071315 A1 | 3/2018 | Cashman et al. |

FOREIGN PATENT DOCUMENTS

| | | |
|---|---|---|
| CA | 2960611 A1 | 3/2016 |
| EP | 169618 A2 | 1/1986 |
| EP | 498824 A1 | 8/1992 |
| EP | 499299 A2 | 8/1992 |
| EP | 580690 A1 | 2/1994 |
| JP | 2009524582 A1 | 2/2009 |
| WO | 9526715 A2 | 10/1995 |
| WO | 9857648 A1 | 12/1998 |
| WO | 145677 A1 | 6/2001 |
| WO | 2007062266 A1 | 5/2007 |
| WO | 2008066899 A2 | 6/2008 |
| WO | 2011088503 A1 | 7/2011 |
| WO | 2013063279 A1 | 5/2013 |
| WO | 2013112605 A2 | 8/2013 |
| WO | 2014028398 A2 | 2/2014 |
| WO | 2014085668 A1 | 6/2014 |
| WO | 2014127201 A1 | 6/2014 |
| WO | 2014160441 A1 | 10/2014 |
| WO | 2014160480 A1 | 10/2014 |
| WO | 2014169831 A1 | 10/2014 |
| WO | 2014169832 A1 | 10/2014 |
| WO | 2014169833 A1 | 10/2014 |

(56) References Cited

FOREIGN PATENT DOCUMENTS

| WO | 2014169836 A1 | 10/2014 |
|---|---|---|
| WO | 2015010054 A1 | 1/2015 |
| WO | 2015081170 | 6/2015 |
| WO | 2015180679 A1 | 12/2015 |
| WO | 2016040322 A1 | 3/2016 |
| WO | 2017066626 A1 | 4/2017 |
| WO | 2017156103 A1 | 9/2017 |
| WO | 2018031748 A1 | 2/2018 |

OTHER PUBLICATIONS

Horioka et al., "Injection Agent—Basics, Preparations, and Applications," Nanzando Co. Ltd., pp. 20-25 (1995).

Loftsson, et al., "Expert Opinion on Drug Delivery", Cyclodextrins in drugs delivery, pp. 335-351 (2005).

Fabian, "Azabenzenes (azines)—The nitrogen derivatives of benzene with one to six N atoms: Stability. homodesmotic stabilization energy, electron distribution, and magnetic ring current; a computational study" Canadian J. Chem, 2004, 82, 50-69.

Press Release: "Marinus Pharmaceuticals' Ganaxolone IV Demonstrates Robust Efficacy in Benzodiazepine-Resistant Models of Status Epilepticus," Published on Apr. 19, 2016, (available at: https://ir.marinuspharma.com/news/news-details/2016/Marinus-Pharmaceuticals-Ganaxolone-IV-Demonstrates-Robust-Efficacy-in-Benzodiazepine-Resistant-Model-of-Status-Epilepticus/default.aspx).

Marinus Pharmaceuticals, "Marinus Pharmaceuticals, Inc. enters into use agreement with CyDex Pharmacweuticals, Inc. for use of Captisol® for Ganaxolone IV," Aug. 12, 2014, Retrieved from the Internet: URL: http://ir.marinuspharma.com/releasedetail.cfm?release id_065715.

Monaghan et al., "Initial Human Experience with Ganaxolone, a Neuroactive Steroid with Antiepileptic Activity" Epilepsia, vol. 38(9), pp. 1026-1031 (1997).

Mula, "Emerging drugs for focal epilepsy." Expert Opinion on Emerging Drugs,18(1):87-95, (2013).

Sham et al., "Formulation and characterization of spray-dried powders containing nanoparticles for aerosol delivery to the lung", International Journal of Pharmaceuticals, vol. 269, pp. 45 (2004).

Valotis et al., "Human Receptor Kinetics, Tissue Binding Affinity, and Stability of Mometasone Furoate" Journal of Pharmaceutical Sciences, vol. 93(5). 14 Pages.

Captisol, accessed from www.captisol.com website maintained by Ligand, on Sep. 26, 2019, five pages.

Hogenkamp et al.; "Synthesis and in Vitro Activity of 3Beta-Substituted-3Alpha-hydroxypregnan-20-ones:Allocteric Modulations of the GABA(A) Receptor"; J. Med. Chem., 40; pp. 61-72 (1997).

Nohria et al.; "Ganaxolone"; The Journal of the American Society for Experimental Neuro Therapeutics; vol. 4; pp. 102-105 (2004).

Pramanick et al.; "Excipient Selection in Parenteral Formulation Development"; Pharma Times, vol. 45(3); pp. 65-77 (2013).

Rogawski et al.; "Neuroactive Steroids for the Treatment of Status Epilepticus"; Epilepsia, vol. 54(6); pp. 93-98 (2013).

Rosetti et al.; "Management of Refractory Status Epilepticus in Adults: Still More Questions Than Answers"; Lancet Nuerol., vol. 10; pp. 922-930 (2011).

Shorvon et al.; "The Treatment of Super-Refractory Status Epilepticus: A Critical Review of Available Therapies and a Clinical Treatment Protocol", Brain, vol. 134; pp. 2802-2818 (2011).

Botella, et al., "Neuroactive Steroids. 1. Positive Allosteric Modulators of the (gamma-Aminobutyric Acid)a eceptor: Structure-Activity Relationships of Heterocyclic Substitution at C-21" Journal of Medicinal Chemistry, vol. 58, pp. 3500-3511 (2015).

Wong et al. "Suspensions for intravenous (IV) injection: A review of development, preclinical and clinical aspects," Advanced Drug Delivery Reviews, vol. 60, pp. 939-954 (2008).

Moyne, et al., "Sterilization of injectable drugs solutions by irradiation" Radiation Physics and Chemistry, vol. 63; pp. 703-704 (2002).

Chai, et al., "Protective effect of polysaccharides on the stability of parenteral emulsions," Drug Development and Industrial Pharmacy, 2013; vol. 39(5), pp. 646-656.

Press Release: "Marinus Pharmaceuticals Provides Business Update and Reports Second Quarter 2016 Financial Results," Published on Aug. 9, 2016 (available at: https://ir.marinuspharma.com/news/news-details/2016/Marinus-Pharmaceuticals-Provides-Business-Update-and-Reports-Second-Quarter-2016-Financial-Results/default.aspx).

Marques, "Dissolution Technologies", Simulated Biological Fluids with Possible Application in Dissolution Testing, p. 15-28.(2011).

"VFEND Full Prescibing Information," updated Jan. 2019, 37 pages.

Saporito et al., Intravenous Administration of Ganaxolone Attenuates Electroencephalographic Seizures in a Diazepam Resistant Model of Status Epilepticus, Neurobiology, 86 (16 supplement), published Apr. 4, 2016.

Press Release: "Marinus Pharmaceuticals Doses First Subject in Phase 1 Clinical Trial for Ganaxolone IV," Published on Jun. 22, 2016, Available at: https://ir.marinuspharma.com/news/news-details/2016/Marinus-Pharmaceuticals-Doses-First-Subject-in-Phase-1-Clinical-Trial-for-Ganaxolone-IV/default.aspx.

Press Release: "Marinus Pharmaceuticals Receives FDA Orphan Drug Designation for Ganaxolone IV to Treat Status Epilepticus," Published Apr. 15, 2016, Available at: https://ir.marinuspharma.com/news/news-details/2016/Marinus-Pharmaceuticals-Receives-FDA-Orphan-Drug-Designation-for-Ganaxolone-IV-to-Treat-Status-Epilepticus/default.aspx.

Chez, "Ganaxolone Therapy Improves Interictal EEG and Seizure Control in Lennox Gastaut Syndrome in Patients with PCDH19 and CDKL5," Annals of Neurol. 80 (suppl 20)published Oct. 26, 2016.

Liptakova, et al., "Effect of Ganaxolone on Flurothyl Seizures in Developing Rats," Epilepsia, 41(7):788-793 (2000).

Pieribone, et al., "Clinical Evaluation of Ganaxolone in Pediatric and Adolescent Patients with Refractory Epilepsy" Epilepsia, vol. 48(10), 5 pages (2007).

Saporito, et al., Ganaxolone Administered Intravenously Prevents Behavioral Seizures and Promotes Survival in the Rat Lithium-Pilocarpine Model of Status Epilepticus, Neurology, 86 (16 Supplement), published Apr. 5, 2016 (available at: https://n.neurology.org/content/86/16_Supplement/111.003).

Press Release: "Marinus Announces Clinical Development Plans for Ganaxolone Intravenous Formulation," Published on Oct. 29, 2015 (available at: https://ir.marinuspharma.com/news/news-details/2015/Marinus-Announces-Clinical-Development-Plans-for-Ganaxolone-Intravenous-Formulation/default.aspx).

Reddy and Kuruba, "Experimental Models of Status Epilepticus and Neuronal Injury for Evaluation of Therapeutic Interventions," Int. J. Mol. Sci. 14:18284-318 (2013).

Seinfeld et al., "Status Epilepticus," in Additional Perspectives on Epilepsy: The Biology of a Spectrum Disorder (Cold Spring Harbor Laboratory Press, 2016, ed. Gregory L. Holmes and Jeffrey L Noebels).

Imtiyaz et al., "The Evolution of the Pilocarpine Animal Model of Status Epilepticus," Heliyon (2020) e04557(2020).

Turski, et al. "Review: Cholinergic Mechanisms and Epileptogenesis. The Seizures Induced by Pilocarpine: A Novel Experimental Model of Intractable Epilepsy," Synapse 3: 154-171 (1989).

Kokate et al., "Neuroactive Steroids Protect Against Pilocarpine- and Kainic Acid-induced Limbic Seizures and Status Epilepticus in Mice," Neuropharmacology, 35(8): 1049-1056 (1996).

American Academy of Neurology ("AAN") 2016 Annual Meeting Scientific Abstract Listing and Meeting Information AAN 2016 Annual Meeting, Vancouver, BC, Canada, Apr. 15, 2016, Available at: https://issuu.com/americanacademyofneurology/docs/16am_abstraclistingdigi_v1424.

Saporito et al., "Ganaxolone Administered Intravenously Prevents Behavioral Seizures and Promotes Survival in the Rat Lithium-Pilocarpine Model of Status Epilepticus," Poster, presented Apr. 17, 2016, at the 2016 AAN Annual Meeting.

(56) References Cited

OTHER PUBLICATIONS

Saporito et al., "Intravenous Administration of Ganaxolone Attenuates Electroencephalographic Seizures in a Diazepam Resistant Model of Status Epilepticus," Poster, presented Apr. 19 and Apr. 20, 2016, at the 2016 AAN Annual Meeting.

Saporito et al., "Ganaxolone Administered IV Blocks Experimental Status Epilepticus," "Data Blitz" Presentation, Apr. 20, 2016, at the 2016 AAN Annual Meeting.

Wylie et al., Status Epilepticus. [Updated May 15, 2022]. In: StatPearls [Internet]. Treasure Island (FL): StatPearls Publishing; Jan. 2022—. Available from: https://www.ncbi.nlm.nih.gov/books/NBK430686/.

Trinka et al., "A definition and classification of status epilepticus—Report of the ILAE Task Force on Classification of Status Epilepticus." Epilepsia, 56(10):1515-1523 (2015).

Tsai et al., "Phase I Study to Determine the Pharmaceutics, Pharmacodynamics, and Safety of IV Ganaxolone in Healthy Adults," Abstract of Poster Presented at the 6th London-Innsbruck Colloquium on Status Epilepticus and Acute Seizures Apr. 6-8, 2017, Salzburg, Austria.

Drug Development and Review Definitions, Aug. 20, 2015, Available at: https://www.fda.gov/drugs/investigational-new-drug-ind-application/drug-development-and-review-definitions.

Press Release: "Marinus Pharmaceuticals Doses First Subject in Phase I Clinical Trial for Ganaxolone IV," Published on Jun. 22, 2016, Available at: https://ir.marinuspharma.com/news/news-details/2016/Marinus-Pharmaceuticals-Doses-First-Subject-in-Phase-1-Clinical-Trial-for-Ganaxolone-IV/default.aspx.

Carter et al., "Characterization of the Anticonvulsant Properties of Ganaxolone (CCD 1042: 3α-Hydroxy-3β-methyl-5α-pregnan-20-one), a Selective, High-Affinity, Steroid Modulator of the γ-Aminobutyric AcidA Receptor," The Journal of Pharmacology and Experimental Therapeutics, 280(3):1284-95 (1997).

Saporito et al., Intravenous Administration of Ganaxolone Attenuates Electroencephalographic Seizures in a Diazepam Resistant Model of Status Epilepticus, Neurobiology, 86 (16 supplement), Abstract, published Apr. 4, 2016.

Saporito et al., Ganaxolone Administered Intravenously Prevents Behavioral Seizures and Promotes Survival in the Rat Lithium-Pilocarpine Model of Status Epilepticus, Neurology 86 (16 Supplement), Abstract, published Apr. 4, 2016.

Chez, "Ganaxolone Therapy Improves Interictal EEG and Seizure Control in Lennox Gastaut Syndrome in Patients with PCDH19 and CDKL5," Annals of Neurol. 80 (suppl 20), S326 published Oct. 26, 2016.

Petition for an Inter Partes Review of U.S. Pat. No. 11,110,100, United States Patent & Trademark Office, Before the Patent Trial and Appeal Board, Case IPR2024-00726, U.S. Pat. No. 11,110,100 B2, dated Mar. 26, 2024.

NCT03350035 Clinical Trial Study Details, ClinicalTrials.gov (Nov. 17, 2017), https://clinicaltrials.gov/study/NCT03350035?term=NCT03350035&rank=1&tab=history&a=1 (last visited Sep. 28, 2023).

Tsai et al., "Phase I study to determine the pharmacokinetics, pharmacodynamics, and safety of IV ganaxolone in healthy adults, Final Programme of the 6th London-Innsbruck Colloquium on Status Epilepticus and Acute Seizures," 74-75 (Apr. 6-8, 2017).

Tsai et al., Phase I Study to Determine the Pharmacokinetics, Pharmacodynamics, and Safety of IV Ganaxolone in Healthy Adults 80 Annals of Neurology S77-78 (Supp. 20 2016).

Ganaxolone Phase 1 Data Supports Progressing to Phase 2 in Patientswith Status Epilepticus, Clinical Leader (Oct. 19, 2016), https://www.clinicalleader.com/doc/ganaxolone-phase-data-progressing-phase-patients-epilepticus-0001 (last visited Sep. 28, 2023).

Ramsay et al., "Pharmacokinetic and Pharmacodynamic (PK/PD) Relationship of Intravenous Ganaxolone in Refractory Status Epilepticus," (Nov. 25, 2019), https://aesnet.org/abstractslisting/pharmacokinetic-and-pharmacodynamic-(pk/pd)-relationship-of-intravenous-ganaxolone-in-refractory-status-epilepticus.

Husain et al., "Intravenous Ganaxolone Achieves Rapid and Dose-Dependent Sustained Improvement in EEG Seizure Burden in Patients with Refractory Status Epilepticus," 37 J. Clin. Neurophysiol. 332 (Jul. 2020).

Treatment of Refractory Status Epilepticus Prevents Need for Induced Coma with Intravenous Anesthetics in Phase 2 Trial, Practical Neurology (Oct. 18, 2019), https://practicalneurology.com/news/treatment-of-refractory-status-epilepticus-prevents-need-for-induced-coma-with-intravenous-anesthetics-in-phase-2-trial (last visited Sep. 28, 2023).

Ramsay, "Pharmacokinetic and Pharmacodynamic (PK/PD) Relationship of Intravenous Ganaxolone in Refractory Status Epilepticus, Marinus Pharmaceuticals," (Dec. 7, 2019), https://marinuspharma.com/wp-content/uploads/2020/09/AES-2019-GNX-in-RSE-Ph2-Poster-vFINAL.pdf (last visited Sep. 28, 2023).

Reddy et al., "Experimental Models of Status Epilepticus and Neuronal Injury for Evaluation of Therapeutic Interventions," 14 Int'l J. Mol. Sci. 18284-318 (2013).

Marinus Corporate Presentation Jun. 2023, Marinus Pharmaceuticals (Jun. 2023), https://s25.q4cdn.com/443656056/files/doc_financials/ 2023/Corporate-Deck-June-FINAL.pdf (last visited Jun. 19, 2023).

Vaitkevicius, "Intravenous ganaxolone for the treatment of refractory status epilepticus: Results from an open-label, dose-finding, phase 2 trial, 63 Epilepsia," 2381-91 (2022).

Hixson, "Stopping Antiepileptic Drugs: When and Why?, 12 Current Treatment Options in Neurology," 434-442 (2010).

Ozdemir et al., "Efficacy of continuous midazolam infusion and mortality in childhood refractory generalized convulsive status epilepticus," 14 Seizure 129-132 (2005).

Sperling et al., "Randomized, double-blind, placebo-controlled phase 2 study of ganaxolone as add-on therapy in adults with uncontrolled partial-onset seizures," 58 Epilepsia 558-564 (2017).

Tsai et al., "Phase 1 Study to Determine the Pharmacokinetics, Pharmacodynamics, and Safety of IV Ganaxolone in Healthy Adults,".

Broomall et al., "Pediatric Super-Refractory Status Epilepticus Treated with Allopregnanolone," 76 Ann Neurol. 911-915 (2014).

Zolkowska et al., "Intramuscular allopregnanolone and ganaxolone in a mouse model of treatment-resistant status epilepticus," 59 Epilepsia 220-227 (Supp. 2 2018).

Vaitkevicius et al., "First-in-man allopregnanolone use in super-refractory status epilepticus," 4 Annals of Clinical Translational Neurol. 411-414 (2017).

Sankar, "Treatment of status epilepticus: Physiology, pharmacology, and future directions," Epilepsia Open 1-8 (May 2023), https://onlinelibrary.wiley.com/doi/epdf/10.1002/epi4.12725.

Marinus Pharmaceuticals Presents Clinical Data of Ganaxolone in Pediatric Epilepsies at Antiepileptic Drug and Device Trials XIII Conference, Marinus Pharmaceuticals (May 18, 2015), https://ir.marinuspharma.com/news/news-details/2015/Marinus-Pharmaceuticals-Presents-Clinical-Data-of-Ganaxolone-in-Pediatric-Epilepsies-at-Antiepileptic-Drug-and-Device-Trials-XIII-Conference/default.aspx (last viewed Sep. 28, 2023).

Currie, "Pharmacology, Part 2: Introduction to Pharmacokinetics," 46 J. Nuclear Med. Tech. 221-30 (Sep. 2018).

141st Annual Meeting of the American Neurological Society, Annals of Neurology, S1-S265, https://onlinelibrary.wiley.com/doi/10.1002/ana.24759 (last accessed Feb. 8, 2024).

* cited by examiner

GANAXOLONE FOR USE IN TREATMENT OF STATUS EPILEPTICUS

The present application is a Continuation of U.S. application Ser. No. 17/186,569 filed Feb. 26, 2021, which is a Continuation of International Patent Application No. PCT/US2020/044843, filed on Aug. 4, 2020, which claims the benefit of U.S. Provisional Application No. 62/882,648 filed on Aug. 5, 2019, each of which are incorporated herein by reference in their entirety.

1. BACKGROUND

Status epilepticus ("SE") is a life-threatening neurological emergency associated with significant morbidity and mortality (Betjemann and Lowenstein, (2015) The Lancet Neurology, 14(6):615-624). In fact, it is the second most common neurologic emergency in the United States with approximately 150,000 cases per year and 55,000 associated deaths per year (Moghasddasi et al., (2015) J. Epilepsy Res., 5(1):13-16).

SE is manifested by prolonged seizure activity, typically persisting more than 5 minutes, or recurrent seizures without recovery of consciousness between seizures. Id. SE requires aggressive treatment to stop the seizure and prevent neurological damage, including neuronal death. SE becomes more difficult to control as its duration increases, and prolonged SE and refractoriness to treatment are associated with poor prognosis (Cherian & Thomas (2009), Ann. Indian. Acad. Neurol., 12(3):140-153). Goals of treatment are rapid seizure cessation, maintenance of seizure control, preventing progression to anesthetics and avoiding further medical complications. Id.

Current treatment protocols for SE take a three-stage approach (Shorvon and Ferlisi (2011), Brain, 134(10)-2802-2818). The first-line treatment is typically with benzodiazepines (e.g., diazepam, lorazepam, and midazolam) (Trinka and Kälviäinen (2017), Seizure, 44:65-73; Glauser et al., (2016), Epilepsy Curr. 26(1):48-61). However, benzodiazepines are ineffective in about 35%-45% of cases and are associated with cardiovascular and respiratory side effects. Id. If SE continues despite treatment with benzodiazepines, other anti-seizure medications (e.g., fosphenytoin, levetiracetam, and valproate) are administered intravenously (IV) as second-line treatment. Id. In instances when SE continues despite first-line and second-line treatment, also called refractory SE, intravenous anesthetics (e.g., thiopental, propofol, and midazolam) are used as third-line treatment. Id. About 31%-41% of patients with SE develop refractory SE. The use of third-line agents produces iatrogenic coma, which necessitates protection of the airways by intubation and mechanical ventilation. Further, use of anesthetics is associated with high morbidity and approximately 35% mortality. If SE continues despite induction of iatrogenic coma, it is termed super-refractory SE. A summary of available therapies for SE, including their adverse effects, is provided in table 1.

TABLE 1

| Summary of Available Therapies in Status Epilepticus | |
|---|---|
| Therapy | Adverse Effects and Other Clinical Considerations |
| First-line Therapy | |
| Benzodiazepines | Respiratory depression and hypotension |
| Second-line Therapy | |
| Fosphenytoin | Cardiovascular risk associated with rapid infusion and must be delivered slowly with cardiac monitoring for toxicity including severe hypotension and cardiac arrhythmias |
| Phenytoin | QT interval prolongation, arrhythmias, and purple glove syndrome; narrow therapeutic range |
| Valproic acid | Hepatotoxic effects, thrombocytopenia, pancreatitis, and hyperammonemia |
| Levetiracetam | Significantly less efficacious than valproic acid and phenytoin |
| Phenobarbital | Respiratory and circulatory depression |
| Lacosamide | Cardiac rhythm and conduction abnormalities |
| Third-line Therapy | |
| Propofol | Hypotension, respiratory depression, and propofol infusion syndrome; hemodynamic complications due to intubation |
| Midazolam | Respiratory depression and hypotension; hemodynamic complications due to intubation |
| Pentobarbital | Respiratory depression, hypotension, and bradycardia; hemodynamic complications due to intubation |

At best, current treatments effectively control moderately severe SE in only about 50% of patients. In severe SE, the success rate is further reduced (Shorvon and Ferlisi, (2011), Brain, 134(1):2802-2818). Moreover, some recent attempts to develop new treatments have failed. For example, brexanolone (SAGE-547), a synthetic form of endogenous allopregnanolone, failed to show efficacy over placebo in a randomized, double-blind, placebo-controlled trial for the treatment in super-refractory SE. (Sage Pharmaceuticals press release Sep. 12, 2017, www.businesswire.com/news/home/20170912005509/en/Sage-Therapeutics-Reports-Top-Line-Results-Phase-3). Accordingly, there is a significant unmet need for effective therapies for treating SE.

2. SUMMARY

This disclosure relates to a method for treating SE. SE is an extremely complicated condition to treat and developing new treatments for SE has been significantly challenging and largely unsuccessful. As noted above, conventional therapies are ineffective in more than 50% of patients. Attempts to develop new treatments for SE have generally failed. For example, brexanolone (i.e., allopregnanolone)

failed to show efficacy over placebo in a double blind, placebo-controlled Phase 3 trial in patients with super refractory SE.

As further described and exemplified herein, the inventors believed that ganaxolone could provide effective therapy for SE. But, given the complexity and difficulties in treating SE, and failure of prior studies to show efficacy, the inventors expected that a high drug exposure for at least 4 days, followed by a maintenance dose for at least about 1 day, would be required for effective treatment of SE. Contrary to these expectations, the inventors surprisingly discovered that administering ganaxolone as a bolus plus continuous infusion to maintain plasma concentration of ganaxolone at a much lower than expected serum level for at least about 8 hours (or possibly at least about 4 hours in some subjects) resulted in rapid and continued suppression of SE. As further described and exemplified herein, continued suppression of SE was achieved when the continuous infusion maintains a plasma concentration of ganaxolone of about 500 ng/ml or higher for a target concentration period of at least about 8 hours or at least about 12 hours (although in some patients 4 hours can be sufficient), in the patients that were studied.

Accordingly, this disclosure relates to a method for effectively treating SE that provides rapid suppression of SE, sustained efficacy (i.e., prevents SE-relapse and provides for continued suppression of SE), and improved safety.

The methods disclosed herein comprise administering to a subject in need thereof a therapeutically effective amount of a neurosteroid, preferably ganaxolone, as an intravenous bolus and a continuous intravenous infusion. The intravenous bolus is administered in an amount to suppress SE. Suppression of SE reduces seizure burden. Typically a ganaxolone plasma concentration of about 500 ng/ml to about 1000 ng/ml is sufficient to suppress SE. For example, to achieve a ganaxolone plasma concentration level of 500 ng/ml to about 1000 ng/ml, an infusion of about 5 mg to about 40 mg of ganaxolone can be infused into the subject at the initiation the intravenous bolus. Preferably, about 30 mg of ganaxolone is infused into the subject at the initiation of the intravenous bolus or during the intravenous bolus The intravenous bolus can be administered (i.e., infused) into the subject for about 1 minute to about 5 minutes.

The continuous intravenous infusion of ganaxolone is administered for a target concentration period in an amount sufficient for continued suppression of SE. Clinically, continued suppression of SE is a reduction in seizure burden.

The continuous intravenous infusion of ganaxolone is initiated periprocedural with the intravenous bolus. The continuous intravenous infusion is generally administered concurrently with the administration of the intravenous bolus. In some cases, the continuous intravenous infusion can be initiated before or after the intravenous bolus.

Continued suppression of SE is achieved when the continuous infusion maintains a plasma concentration of ganaxolone of about 500 ng/ml or higher throughout a target concentration period. The continuous infusion is administered throughout the treatment period, which include the target concentration period, during which the subject's plasma concentration of ganaxolone is maintained at or above a target concentration, such as about 425 ng/ml, about 45 ng/ml, about 475 ng/ml or preferably about 500 ng/ml. Although, it is recognized that a plasma concentration of about 425 ng/ml, at least about 450 ng/ml, or at least about 475 ng/ml or is preferably at least about 500 ng/ml is sufficient to maintain continued SE suppression. Generally, it is desired that the ganaxolone plasma concentration is not higher than about 1000 ng/ml. This is because a ganaxolone plasma concentration of higher than 1000 ng/ml can induce anesthesia, which is not a desired effect of the treatment. The target concentration period is typically at least about 8 hours or at least 12 hours. In some cases, it is possible that the target concentration can be at least about 4 hours. Typically, the amount of ganaxolone administered to the subject per hour by continuous intravenous infusion during the target concentration period can be increased or decreased to maintain continued suppression of SE, but is sufficient to maintain a ganaxolone plasma concentration of at least about 500 ng/ml.

The amount of ganaxolone administered to the subject per hour by continuous intravenous infusion can be decreased over a period of about 24 hours from the initiation of the continuous intravenous infusion. The amount of ganaxolone administered to the subject per hour by continuous intravenous infusion can be decreased about 2 hours and/or about 10 hours to about 14 hours after the initiation of the continuous intravenous infusion. The amount of ganaxolone administered to the subject per hour by continuous intravenous infusion is preferably decreased about 2 hours after the initiation of the continuous intravenous infusion and then about 10 hours to about 14 hours after the initiation of the continuous intravenous infusion.

The amount of ganaxolone administered to the subject per hour by continuous intravenous infusion can be decreased by about 50%, relative to the amount administered per hour at the initiation of the continuous intravenous infusion, about 2 hours after the initiation of the continuous intravenous infusion. The amount of ganaxolone administered to the subject per hour by continuous intravenous infusion can be decreased by about 75%, relative to the amount administered per hour at the initiation of the continuous intravenous infusion, about 10 hours to about 14 hours after the initiation of the continuous intravenous infusion. The amount of ganaxolone administered to the subject per hour by continuous intravenous infusion can be decreased by about 50%, relative to the amount administered per hour at the initiation of the continuous intravenous infusion, about 2 hours after the initiation of the continuous infusion, and then by about 75%, relative to the amount administered per hour at the initiation of the continuous intravenous infusion, about 10 hours to about 14 hours after the initiation of the continuous infusion.

The amount of ganaxolone administered to the subject per hour by continuous intravenous infusion can be decreased by about 50%, relative to the rate given during the target concentration period at 2 to 12 hours after initiation of the infusion. After another 12 to 24 hours after the initiation of the continuous intravenous, the continuous intravenous infusion can again be decreased by half, or 75% of the target concentration period infusion rate.

About 20 mg of ganaxolone per hour to about 80 mg of ganaxolone per hour can infused into the subject during the continuous infusion treatment period. In general, about 80 mg of ganaxolone per hour can be infused into the subject at the initiation of the continuous intravenous infusion. After about 2 hours, amount of ganaxolone can then be decreased to about 40 mg of ganaxolone per hour then to about 20 mg of ganaxolone per hour during the treatment period. In some instances, about 80 mg of ganaxolone can be administered to the subject by the continuous intravenous infusion from initiation and for about 2 hours thereafter, then about 40 mg of ganaxolone per hour can be administered to the subject by continuous intravenous infusion starting about 2 hours after initiation and for about 2 hours to about 10 hours thereafter, then about 20 mg of ganaxolone per hour can be administered to the subject by continuous intravenous infusion starting about 12 hours after initiation and for about 12 hours to about 24 hours thereafter.

The amount of ganaxolone administered to the subject per by continuous intravenous infusion can be increased after about 24 hours from the initiation of the intravenous infusion. In general, the amount of ganaxolone administered per hour by continuous intravenous infusion can be increased by up to by about 45%, relative to the amount administered per hour starting after about 24 hours after initiation of the continuous intravenous infusion. For instance, the amount of ganaxolone infused into the subject by continuous intravenous infusion can be increased up to about 45 mg of ganaxolone per hour, but preferably does not exceed 45 mg, starting about 24 hours after the initiation and for up to about 12 hours thereafter. The amount of ganaxolone can be increased for a period of up to 12 hours.

The treatment period of the continuous intravenous infusion can be for a period of about 36 hours, about 48 hours, about 72 hours, or about 96 hours after the initiation of the intravenous infusion. Preferably, the treatment period is for a period of at least about 8 hours to about 36 hours after the initiation of the continuous intravenous infusion.

The continuous intravenous infusion is typically followed by a tapering period. The taper period generally starts at about 36 hours from the initiation of the continuous intravenous infusion. During the taper period the continuous intravenous infusion of ganaxolone is systematically decreased, typically by reducing the amount of ganaxolone that is administered to the subject by about one third every four hours until the subject no longer requires ganaxolone.

The methods disclosed herein are suitable to treat any form of SE. For example, generalized convulsive SE, non-convulsive SE, refractory SE, and super refractory SE. The method is particularly useful for treating refractory SE. The method can also be used to treat subjects that have failed first-line treatment (e.g., benzodiazepine), second-line treatment (e.g. fosphenytoin, valproic acid or levetiracetam), and/or third-line treatment (thiopental, midazolam, pentobarbital, or propofol). During the treatment, the subject can be monitored for plasma concentration of ganaxolone and using EEG for seizure activity.

The ganaxolone formulation used in the methods disclosed herein preferably comprises sulfobutylether-β-cyclodextrin.

To summarize, an exemplary method of treating SE includes administering a subject an intravenous bolus dose of ganaxolone of about 5 to about 40 mg, preferably about 30 mg, over a period of about 1 to about 5 minutes, typically about 3 minutes, to achieve a short term increase in ganaxolone plasma concentration of about 800 ng/ml to about 1000 ng/ml. The intravenous bolus suppresses SE. Concurrently with the intravenous bolus or after the intravenous bolus, the subject is administered a continuous intravenous infusion. The continuous intravenous infusion provides continued suppression of SE. Continued suppression of SE is achieved when the continuous intravenous infusion maintains a plasma concentration of ganaxolone of about 500 ng/ml or higher for a target concentration period. The target concentration period is typically for a period of at least about 8 hours or at least about 12 hours. Although, in some cases, at least about 4 hours may be a sufficient target concentration period. During the target concentration period, the amount of ganaxolone infused can be increased and/or decreased to maintain the desired plasma ganaxolone concentration. The amount of ganaxolone administered to the subject per hour is typically decreased by about 50% relative to the amount administered per hour at the initiation of the continuous infusion about 2 hours about the initiation of the continuous intravenous infusion. The amount of ganaxolone administered to the subject per hour can then be decreased by 75% relative to the amount administered at the initiation of the continuous intravenous infusion. The continuous intravenous infusion is typically followed by a tapering period.

The methods disclosed herein comprise administering a therapeutically effective amount of ganaxolone to reduce or eliminate seizure activity and/or reduce or eliminate convulsions and/or completely suppresses status epilepticus (i.e., suppress EEG seizure activity and convulsions) in the subject. In certain embodiments, the therapeutically effective amount of ganaxolone to reduce or eliminate seizure activity and/or completely suppresses status epilepticus in the subject is the amount that provides and maintains a plasma concentration of ganaxolone of about 50 ng/ml to about 3500 ng/ml in the subject over a time period sufficient to reduce or eliminate seizure activity and/or reduce or eliminate convulsions and/or completely suppresses status epilepticus in the subject. In certain embodiments, the plasma concentration of about 50 mg/ml to about 3500 ng/ml is provided by (i) administering a bolus (e.g., from about 5 mg to about 100 mg, from about 25 mg to about 60 mg, or from about 25 mg to about 30 mg) of ganaxolone over about 1 to about 5 minutes intravenously; (ii) administering a continuous intravenous infusion of ganaxolone at a rate between about 5 mg/hour and about 130 mg/hour (e.g., from about 5 mg/hour to about 85 mg/hour) for about 8 hours to about 120 hours (e.g., for about 10 hours to about 96 hours), the continuous intravenous infusion starting at about the time of the bolus injection or a short time thereafter (e.g., within about 30 min); and (iii) lowering the rate of intravenous infusion rate over about 12 hours to about 24 hours (e.g., over 12 hours, about 10 hours, about 14 hours, about 16 hours, about 18 hours, or about 20 hours) before the continuous infusion is stopped. In certain embodiments, the plasma concentration of about 50 mg/ml to about 3500 ng/ml is provided by (i) administering a bolus (e.g., from about 5 mg to about 100 mg, from about 25 mg to about 60 mg, or from about 25 mg to about 30 mg) of ganaxolone over about 1 to about 5 minutes intravenously; (ii) administering a continuous intravenous infusion of ganaxolone at a rate between about 5 mg/hour and about 130 mg/hour (e.g., from about 5 mg/hour to about 85 mg/hour) for about 24 hours to about 120 hours (e.g., for about 48 hours to about 96 hours), the continuous intravenous infusion starting at about the time of the bolus injection or a short time thereafter (e.g., within about 30 min); and (iii) lowering the rate of intravenous infusion rate over about 10 hours to about 24 hours (e.g., over 10 hours, about 12 hours, about 14 hours, about 16 hours, about 18 hours, or about 20 hours) before the continuous infusion is stopped. In some embodiments, a portion of the therapeutically effective amount (e.g., from about 5 mg to about 100 mg, from about 10 mg to about 90 mg, from about 15 mg to about 80 mg, from about 20 mg to about 70 mg, from about 25 mg to about 60 mg, etc.) is administered via a bolus intravenous injection, and the remaining portion of the therapeutically effective amount is administered via a continuous intravenous infusion. In some embodiments, for subjects weighing 40 kg or more, from about 5 mg to about 100 mg (e.g., from about 10 mg to about 90 mg, from about 15 mg to about 80 mg, from about 20 mg to about 70 mg, from about 25 mg to about 60 mg, etc.) of ganaxolone may be administered via the bolus intravenous injection, and the remainder of dose is administered via an intravenous infusion at a rate greater than about 10 mg/hour, 15 mg/hour, 20 mg/hour or 25 mg/hour for about 1 hour to about 120 hours. In some embodiments, the continuous intravenous infusion is at a rate from about 5 mg/hour to about 130 mg/hr, about 5 mg/hour to about 120 mg/hour, from about 5 mg/hour to about 110 mg/hr, from about 5 mg/hour to about 100 mg/hr, from about 5 mg/hour to about 90 mg/hr, or from about 5 mg/hour to about 85 mg/hr for about 1 hour to about 120 hours. In some embodiments, the continuous intravenous infusion is at a rate from about 50 mg/hr to about 130 mg/hr for at least 1 hour. In some embodiments, the therapeutically effective dose, or a portion thereof, is administered intravenously at a rate from about 40 mg/hour to about 140 mg/hour for about 1 hour to about 4 hours; thereafter, at a rate from about 20 mg/hour to about 70 mg/hour for about 1 hour to about 4 hours; thereafter, at a rate from about 10 mg/hour to about 35 mg/hour for about 1 hour to about 4 hours; thereafter, at a rate from about 10 mg/hour to about 30 mg/hour for about 1 hour to about 96 hours; and, thereafter at about 15 mg/hour to about 35 mg/hour for about 1 hour to about 96 hours. In some embodiments, after the administration at the rate from about 15 mg/hour to about 35 mg/hour for about 1 hour to about 96 hours, the rate is reduced by about 10% to about 50% every 1 hour to 12 hours (e.g., the rate may be reduced from about 15% to about 30% every 4 hours to 8 hours). In some of these embodiments, ganaxolone is administered at about 18 mg/hour, about 20 mg/hour, about 22 mg/hour; about 25 mg/hour, about 28 mg/hour, about 30 mg/hour, about 35 mg/hour, about 40 mg/hour, about 45 mg/hour, about 50 mg/hour, about 60 mg/hour, about 65 mg/hour, or about 70 mg/hour, for at least about 1 hour of the administration. For subjects weighing less than 40 kg, in some embodiments, a bolus dose from about 0.07 mg/kg to about 1.43 mg/kg (e.g., from about 0.125 mg/kg to about 0.4 mg/kg) is administered (over 1 to 5 minutes); and, thereafter, via a continuous infusion from about 0.8 mg/kg/hour to about 2 mg/kg/hour for about 1 to 3 hours; followed by a continuous infusion at a rate from about 0.6 mg/kg/hour to about 1 mg/hr for about 4 to 8 hours; and, thereafter, followed by a continuous infusion at a rate from about 0.15 mg/kg/hour to about 0.4 mg/kg/hour for 13 to 19 hours. At the end of the 24 hours of continuous infusion, the infusion rate may be increased to, e.g., a rate from about 0.2 mg/kg/hour to about 0.6 hour for 24 to 48 hours or 24 to 96 hours.

This disclosure is also directed to a method of treating status epilepticus (e.g., a generalized convulsive status epilepticus, non-convulsive status epilepticus, early status epilepticus, established status epilepticus, refractory status epilepticus, or super-refractory status epilepticus), comprising administering a therapeutic dose of ganaxolone to a subject experiencing status epilepticus in a manner which provides a plasma concentration of ganaxolone of about 50 ng/ml to about 3500 ng/ml over a time period of about 24 hours to about 120 hours, and from about 2 to 5 peaks in the plasma concentration of ganaxolone during said 24 hours to about 120 hours. In certain embodiments, a portion of the therapeutic dose is administered via an intravenous infusion at a rate from about 20 mg/hour to about 140 mg/hour for about 4 hours to about 120 hours, a ganaxolone plasma level from about 800 ng/ml to about 1600 ng/ml is maintained for about 1 hour to about 96 hours, and a portion of the dose is administered via a bolus injection. For subjects weighing 40 kg or more, the bolus injection may comprise, e.g., from about 5 mg to about 100 mg ganaxolone, and the amount of ganaxolone delivered via an intravenous infusion may be, e.g., from about 450 mg to about 3000 mg. In some embodiments, from about 450 mg to about 1000 mg of ganaxolone is administered over each 24 hours of said 24 hours to about 120 hours. For subjects weighing less than 40 kg, the bolus injection may comprise, e.g., from about 0.25 mg to about 16 mg, and from about 100 mg to about 600 mg of ganaxolone may be administered over each 24 hours of the intravenous infusion.

This disclosure is also directed to a method of treating status epilepticus (e.g., generalized convulsive status epilepticus, non-convulsive status epilepticus, early status epilepticus, established status epilepticus, refractory status epilepticus, or super-refractory status epilepticus) comprising administering intravenously a therapeutically effective dose of ganaxolone, or a portion thereof, to reduce or eliminate seizure activity and/or reduce or eliminate convulsions and/or completely suppresses status epilepticus in the subject experiencing status epilepticus over a time period from about 1 hours to about 120 hours, from about 2 hours to about 100 hours, from about 3 hours to about 100 hours, from about 4 hours to about 100 hours, from about 4 hours to about 96 hours (e.g., via a continuous intravenous infusion), wherein the intravenous infusion is started after a bolus dose from about 5 mg to about 100 mg (e.g., about 6 mg, 8 mg, 10 mg, 12 mg, 14 mg, 16 mg, 18 mg, 20 mg, 22 mg, 24 mg, 26 mg, 28 mg, 30 mg, 32 mg, 34 mg, 36 mg, 38 mg, 40 mg, 42 mg, 44 mg, 46 mg, 48 mg, 50 mg, 52 mg, 54 mg, 56 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, or 99 mg) is intravenously administered to the subject (e.g., from about 1 second to about 1 hour, from about 1 second to about 45 minutes, from about 1 second to about 30 minutes, from about 1 second to about 15 minutes, from about 1 second to about 10 minutes, from about 1 second to about 5 minutes or from about 2 seconds to about 3 minutes after the bolus dose). In some of the these embodiments, the bolus dose is from about 5 mg to about 90 mg, from about 5 mg to about 80 mg, form about 5 mg to about 70 mg, from about 5 mg to about 60 mg, from about 5 mg to about 50 mg, from about 5 mg to about 40 mg, or form about 5 mg to about 30 mg.

This disclosure is further directed to a method of treating a subject experiencing status epilepticus (e.g., a generalized convulsive status epilepticus, non-convulsive status epilepticus, early status epilepticus, established status epilepticus, refractory status epilepticus, or super-refractory status epilepticus) comprising administering intravenously from about 450 mg to about 3000 mg ganaxolone over a time period from about 4 hours to about 120 hours at a rate sufficient to reduce or eliminate seizure activity and/or reduce or eliminate convulsions and/or completely suppresses status epilepticus in the subject. In certain embodiments, the rate is greater than about 10 mg/hour, 15 mg/hour, 20 mg/hour, 25 mg/hour, or 30 mg/hour. In some embodiments from about 5 mg to about 100 mg of ganaxolone is administered via a bolus intravenous injection, and the remainder of dose is administered via a continuous intravenous infusion at a rate greater than about 25 mg/hour for a time period from about 1 hour to about 120 hours.

This disclosure is also directed to a method of treating status epilepticus (e.g., a generalized convulsive status epilepticus, non-convulsive status epilepticus, early status epilepticus, established status epilepticus, refractory status epilepticus, or super-refractory status epilepticus) in a subject comprising administering from about 1 gram to about 100 grams (e.g., from about 20 grams to about 70 grams, from about 25 grams to about 65 grams, from about 30 grams to about 60 grams, from about 35 grams to about 55 grams, etc.) sulfobutylether-β-cyclodextrin to the subject per day in a formulation comprising ganaxolone.

This disclosure is further directed to a method of treating a subject experiencing status epilepticus (e.g., a generalized convulsive status epilepticus, non-convulsive status epilepticus, early status epilepticus, established status epilepticus, refractory status epilepticus, or super-refractory status epilepticus) comprising administering intravenously to the subject a formulation comprising ganaxolone and sulfobutylether-β-cyclodextrin in a weight ratio from about 1:50 to about 1:75, wherein from about 450 mg to about 1000 mg of ganaxolone and from about 1 gram to about 100 grams sulfobutylether-β-cyclodextrin is administered per day. In some embodiments, the weight ratio is about 1:60, about 1:65 or about 1:70.

This disclosure is further directed to a method of treating a subject experiencing status epilepticus (e.g., a generalized convulsive status epilepticus, non-convulsive status epilepticus, early status epilepticus, established status epilepticus, refractory status epilepticus, or super-refractory status epilepticus) comprising administering intravenously to the subject a formulation comprising ganaxolone and sulfobutylether-β-cyclodextrin in a weight ratio from about 1:50 to about 1:75 at a rate and for a duration sufficient to provide plasma concentration of ganaxolone of about 50 ng/ml to about 3500 ng/ml over a time period of about 24 hours to about 120 hours. In some of these embodiments, the weight ratio ganaxolone and sulfobutylether-β-cyclodextrin is about 1:51, about 1:52, about 1:53, about 1:54, about 1:55, about 1:56, about 1:57, about 1:58, about 1:59, about 1:60, about 1:61, about 1:62, about 1:63, about 1:64, about 1:65, about 1:66, about 1:67, about 1:68, about 1:69, about 1:70, about 1:71, or about 1:72.

In an additional aspect, the method of treating status epilepticus (e.g., a generalized convulsive status epilepticus, non-convulsive status epilepticus, early status epilepticus, established status epilepticus, refractory status epilepticus, or super-refractory status epilepticus) comprises administering ganaxolone via an intravenous infusion at a rate that is varied during administration from about 10 mg/hour to about 150 mg/hour, about 15 mg/hour to about 150 mg/hour or about 20 mg/hour to about 150 mg/hour. In some embodiments, the therapeutically effective dose, or a portion thereof, is administered parenterally at a rate from about 40 mg/hour to about 140 mg/hour for about 1 hour to about 4 hours; then, at a rate from about 20 mg/hour to about 70 mg/hour for about 1 hour to about 4 hours; then, at a rate from about 10 mg/hour to about 35 mg/hour for about 1 hour to about 4 hours; then, at a rate from about 10 ng/hour to about 30 mg/hour for about 1 hour to about 96 hours; and, then, at a rate from about 15 mg/hour to about 35 mg/hour for about 1 hour to about 96 hours. In some embodiments, after the administration at the rate from about 15 mg/hour to about 35 mg/hour for about 1 hour to about 96 hours, the rate is reduced by about 10% to about 50% every 1 hour to 12 hours (e.g., the rate may be reduced from about 15% to about 30% every 4 hours to 8 hours). In some of these embodiments, ganaxolone may be administered at a rate of at least about 18 mg/hour, about 20 mg/hour, about 22 mg/hour; about 25 mg/hour, about 28 mg/hour, about 30 mg/hour, about 35 mg/hour, about 40 mg/hour, about 45 mg/hour, about 50 mg/hour, about 60 mg/hour, about 65 mg/hour, or about 70 mg/hour, for at least about 1 hour of the administration. In certain embodiments, a bolus dose of ganaxolone is administered intravenously before the start of the intravenous infusion. The bolus dose of ganaxolone may comprise, e.g., from about 5 mg to about 100 mg ganaxolone. In certain embodiments, one or more additional bolus doses of ganaxolone are administered intravenously before, during or after the intravenous infusion. The additional bolus dose may comprise, e.g., from about 5 mg to about 100 mg ganaxolone.

This disclosure is also directed in part to a method of treating status epilepticus (e.g., a generalized convulsive status epilepticus, non-convulsive status epilepticus, early status epilepticus, established status epilepticus, refractory status epilepticus, or super-refractory status epilepticus) comprising administering ganaxolone over a time period from about 2 hours to about 120 hours, from about 2 hours to about 100 hours, from about 3 hours to about 100 hours, from about 4 hours to about 100 hours, from about 4 hours to about 96 hours, from about 5 hours to about 96 hours, from about 6 hours to about 96 hours, from about 6 hours to about 90 hours, from about 6 hours to about 88 hours, or from about 10 hours to about 72 hours to a subject experiencing status epilepticus in an amount and at a rate sufficient to provide a plasma concentration of ganaxolone from about 50 ng/ml to about 3500 ng/ml, from about 75 ng/ml to about 3250 ng/ml, from about 100 ng/ml to about 3000 ng/ml, from about 125 ng/ml to about 2750 ng/ml, from about 150 ng/ml to about 2500 ng/ml, from about 175 ng/ml to about 2250 ng/ml, from about 200 ng/ml to about 2200 ng/nil, about 250 ng/ml to about 2150 ng/ml, from about 300 ng/ml to about 2100 ng/ml, from about 350 ng/ml to about 2100 ng/ml, from about 400 ng/ml to about 2100 ng/ml, or from about 450 ng/ml to about 2100 ng/ml, from about 500 ng/ml to about 2000 ng/ml, from about 500 ng/ml to about 1800 ng/ml, from about 500 ng/ml to about 1600 ng/ml, from about 500 ng/ml to about 1500 ng/ml, from about 600 ng/ml to about 1400 ng/ml, from about 600 ng/ml to about 1300 ng/ml, from about 650 ng/ml to about 1200 ng/ml, from about 700 ng/ml to about 1200 ng/ml, from about 750 ng/ml to about 1100 ng/ml, from about 800 ng/ml to about 1100 ng/ml for a time period from about 30 min to about 120 hours (e.g., for about 1 hour, 3 hours, 5 hours, 7 hours, 9 hours, 11 hours, 13 hours, 15 hours, 17 hours, 19 hours, 21 hours, 23 hours, 25 hours, 27 hours, 29 hours, 31 hours, 33 hours, 35 hours, 37 hours, 39 hours, 41 hours, 43 hours, 45 hours, 47 hours, 49 hours, 51 hours, 53 hours, 55 hours, 57 hours, 59 hours, 61 hours, 63 hours, 65 hours, 67 hours, 69 hours, 71 hours, 73 hours, 75 hours, 77 hours, 79 hours, 81 hours, 83 hours, 85 hours, 87 hours, 89 hours, 91 hours, 93 hours, or 95 hours).

The present disclosure is also directed in part to a method of treating status epilepticus (e.g., a generalized convulsive status epilepticus, non-convulsive status epilepticus, early status epilepticus, established status epilepticus, refractory status epilepticus, or super-refractory status epilepticus) comprising administering a bolus dose of ganaxolone intravenously in an amount sufficient to achieve a maximum plasma ganaxolone concentration (Cmax) from about 50 ng/ml to about 3500 ng/ml, from about 75 ng/ml to about 3250 ng/ml, from about 100 ng/ml to about 3000 ng/ml, from about 125 ng/ml to about 2750 ng/ml, from about 150 ng/ml to about 2500 ng/ml, from about 175 ng/ml to about 2250 ng/ml, from about 200 ng/ml to about 2200 ng/ml, from about 250 ng/ml to about 2150 ng/ml, from about 300 ng/ml to about 2100 ng/ml, from about 350 ng/ml to about 2100 ng/ml, from about 400 ng/ml to about 2100 ng/ml, from about 450 ng/ml to about 2100 ng/ml, or from about 500 ng/ml to about to about 2000 ng/ml within 5 minutes of administration, and, after the bolus dose is administered (i.e., from about 1 second to about 1 hour, from about 1 second to about 45 minutes, from about 1 second to about 30 minutes, from about 1 second to about 15 minutes, from about 1 second to about 10 minutes, from about 1 second to about 5 minutes or from about 2 seconds to about 3 minutes after the bolus dose), administering ganaxolone via a continuous intravenous infusion over a time period from about 2 hours to about 120 hours, from about 2 hours to about 100 hours, from about 3 hours to about 100 hours, from about 4 hours to about 100 hours, or from about 4 hours to about 96 hours (e.g., over about 6 hours, 8 hours, 10 hours, 12 hours, 14 hours, 16 hours, 18 hours, 20 hours, 22 hours, 24 hours, 26 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, 72 hours, 74 hours, 76 hours, 78 hours, 80 hours, 82 hours, 84 hours, 86 hours, 88 hours, 90 hours, 92 hours, or 94 hours) in an amount and at a rate sufficient to maintain a plasma concentration of ganaxolone from about 50 ng/ml to about 3500 ng/ml, from about 75 ng/ml to about 3250 ng/ml, from about 100 ng/ml to about 3000 ng/ml, from about 125 ng/ml to about 2750 ng/ml, from about 150 ng/ml to about 2500 ng/ml, from about 175 ng/ml to about 2250 ng/ml, from about 200 ng/ml to about 2200 ng/ml, from about 250 ng/ml to about 2150 ng/ml, from about 300 ng/ml to about 2100 ng/ml, from about 350 ng/ml to about 2100 ng/ml, from about 400 ng/ml to about 2100 ng/ml, from about 450 ng/ml to about 2100 ng/ml, from about 500 ng/ml to about 1800 ng/ml, from about 600 ng/ml to about 1700 ng/ml, from about 650 ng/ml to about 1600 ng/ml, from about 700 ng/ml to about 1500 ng/ml, from about 750 ng/ml to about 1400 ng/ml, from about 800 ng/ml to about 1300 ng/ml for from about 1 hour to about 96 hours. For subjects weighing 40 kg, or more, the total daily dose of ganaxolone may be, e.g., from about 450 mg to about 2000 mg, from about 500 mg to about 1900 mg, from about 500 mg to about 1800 mg, from about 550 mg to about 1600 mg, from about 550 mg to about 1400 mg, from about 550 mg to about 1200 mg, or from about 600 mg to about 1100 mg, and the bolus dose may comprise, e.g., from about 5 mg to about 100 mg.

The present disclosure is further directed in part to a method of treating status epilepticus (e.g., a generalized convulsive status epilepticus, non-convulsive status epilepticus, early status epilepticus, established status epilepticus, refractory status epilepticus, or super-refractory status epilepticus) comprising administering, a bolus dose of ganaxolone intravenously in an amount sufficient to achieve a maximum plasma ganaxolone concentration (Cmax) from about 50 ng/ml to about 3500 ng/ml, from about 75 ng/ml to about 3250 ng/ml, from about 100 ng/ml to about 3000 ng/ml, from about 125 ng/ml to about 2750 ng/ml, from about 150 ng/ml to about 2500 ng/ml, from about 175 ng/ml to about 2250 ng/ml, from about 200 ng/ml to about 2200 ng/ml, from about 250 ng/ml to about 2150 ng/ml, from about 300 ng/ml to about 2100 ng/ml, from about 350 ng/ml to about 2100 ng/ml, from about 400 ng/ml to about 2100 ng/ml, from about 450 ng/ml to about 2100 ng/ml, or from about 500 ng/ml to about 1500 ng/ml within about 5 minutes of administration; and, after the bolus dose (e.g., from about 1 second to about 1 hour, from about 1 second to about 45 minutes, from about 1 second to about 30 minutes, from about 1 second to about 15 minutes, from about 1 second to about 10 minutes, from about 1 second to about 5 minutes or from about 2 seconds to about 3 minutes after the bolus dose), administering ganaxolone intravenously over a time period from about 2 hours to about 120 hours, from about 2 hours to about 100 hours, from about 3 hours to about 100 hours, from about 4 hours to about 100 hours, from about 4 hours to about 96 hours, from about 5 hours to about 96 hours, from about 6 hours to about 96 hours, from about 6 hours to about 90 hours, or from about 6 hours to about 88 hours, or from about 10 hours to 72 hours via an intravenous infusion in an amount and at a rate to maintain a plasma concentration of ganaxolone from about 600 ng/ml to about 1500 ng/ml for more than 1 hour (e.g., for about 2 hours, 4 hours, 6 hours, 8 hours, 10 hours, 12 hours, 14 hours, 16 hours, 18 hours, 20 hours, 22 hours, 24 hours, 26 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, 72 hours, 74 hours, 76 hours, 78 hours, 80 hours, 82 hours, 84 hours, 86 hours, 88 hours, 90 hours, 92 hours, 94 hours, 96 hours, etc.).

The present disclosure is also directed in part to a method of treating status epilepticus (e.g., a generalized convulsive status epilepticus, non-convulsive status epilepticus, early status epilepticus, established status epilepticus, refractory status epilepticus, or super-refractory status epilepticus) in a subject comprising administering parenterally (e.g., via an intravenous (IV) infusion) from about 400 mg to about 1500 mg ganaxolone for at least one day to a subject experiencing status epilepticus. In certain embodiments, a portion of the daily dose is administered via a bolus injection, and the remaining portion of the dose is administered via a continuous infusion.

In addition, the disclosure is directed to a method of treating status epilepticus (e.g., a generalized convulsive status epilepticus, non-convulsive status epilepticus, early status epilepticus, established status epilepticus, refractory status epilepticus, or super-refractory status epilepticus) in a subject comprising administering from about 700 mg to about 1200 mg of ganaxolone intravenously, wherein the administration provides a plasma level of ganaxolone from about 50 ng/ml to about 3500 ng/ml, from about 75 ng/ml to about 3250 ng/ml, from about 100 ng/ml to about 3000 ng/ml, from about 125 ng/ml to about 2750 ng/ml, from about 150 ng/ml to about 2500 ng/ml, from about 175 ng/ml to about 2250 ng/ml, from about 200 ng/ml to about 2200 ng/ml, from about 250 ng/ml to about 2150 ng/ml, from about 300 ng/ml to about 2100 ng/ml, from about 350 ng/ml to about 2100 ng/ml, from about 400 ng/ml to about 2100 ng/ml, from about 450 ng/ml to about 2100 ng/ml, from about 500 ng/ml to about 1400 ng/ml, from about 500 ng/ml to about 1300 ng/ml, from about 500 ng/ml to about 1200 ng/ml, from about 600 ng ml to about 1200 ng/ml, from about 600 ng/ml to about 1100 ng/ml, from about 650 ng/ml to about 1100 ng/ml, from about 700 ng/ml to about 1100 ng/ml, from about 750 ng/ml to about 1100 ng/ml, from about 800 ng/ml to about 1100 ng/ml for at least 1 hour (e.g., 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 24 hours, etc.), wherein a portion of the dose is administered via a bolus intravenous injection, and the remaining dose is administered via a continuous intravenous infusion.

This disclosure is also directed to a method of treating status epilepticus (e.g., a generalized convulsive status epilepticus, non-convulsive status epilepticus, early status epilepticus, established status epilepticus, refractory status epilepticus, or super-refractory status epilepticus) in a subject comprising administering from about 500 mg to about 1200 mg of ganaxolone parenterally (e.g., intravenously) for a time period from about 1 hour to 8 hours (e.g., 2, 4, 5 or 6 hours) at a variable rate from about 10 mg/hr to about 150 mg/hr, from about 15 mg/hr to about 140 mg/hr, or from about 15 mg/hr to about 120 mg/hr, wherein the administration stops EEG seizure activity (e.g., continuous ictal discharges) in the subject. In embodiments, ganaxolone is administered at a rate from about 50 mg/hr to about 130 mg/hr.

This disclosure is further directed in part to a method of treating a subject experiencing non-convulsive EEG seizures, the method comprising administering a therapeutically effective amount of ganaxolone to stop or reduce frequency of the non-convulsive EEG seizures in the subject. In certain embodiments, the therapeutically effective amount of ganaxolone is the amount that provides and maintains a plasma concentration of ganaxolone from about 50 ng/ml to about 3500 ng/ml, from about 75 ng/ml to about 3250 ng/ml, from about 100 ng/ml to about 3000 ng/ml, from about 125 ng/ml to about 2750 ng/ml, from about 150 ng/ml to about 2500 ng/ml, from about 175 ng/ml to about 2250 ng/ml, from about 200 ng/ml to about 2200 ng/ml, from about 250 ng/ml to about 2150 ng/ml, from about 300 ng/ml to about 2100 ng/ml, from about 350 ng/ml to about 2100 ng/ml, from about 400 ng/ml to about 2100 ng/ml, from about 450 ng/ml to about 2100 ng/ml, or from about 500 ng/ml to about 1900 ng/ml in the subject. In some embodiments, a portion of the therapeutically effective amount is administered via a bolus intravenous injection, and the remaining portion of the therapeutically effective amount is administered via a continuous intravenous infusion. For example, when the subject weighs 40 kg, or more, in some embodiments, from about 5 mg to about 100 mg of ganaxolone is administered via the bolus intravenous injection, and the remainder of dose is administered via an intravenous infusion at a rate greater than 10 mg/hour, 15 mg/hour, 20 mg/hour, 25 mg/hour, 30 mg/hour, 35 mg/hour, 40 mg/hour, 45 mg/hour, 50 mg/hour, 55 mg/hour, 60 mg/hour, 65 mg/hour, 70 mg/hour, 75 mg/hour, 80 mg/hour, or 85 mg/hour for a time period from about 1 hour to about 120 hours (e.g., 2 hours, 3 hours, 4 hours, 5 hours, 6 hours, 7 hours, 8 hours, 9 hours, 10 hours, 11 hours, 12 hours, etc.).

This disclosure is also directed to a method of treating non-convulsive EEG seizures comprising administering intravenously a therapeutically effective dose of ganaxolone, or a portion thereof, to stop or reduce frequency of the non-convulsive EEG seizures in the subject over a time period from about 2 hours to about 120 hours, from about 2 hours to about 100 hours, from about 3 hours to about 100 hours, from about 4 hours to about 100 hours, from about 4 hours to about 96 hours, from about 5 hours to about 96 hours, from about 6 hours to about 96 hours, from about 6 hours to about 90 hours, from about 6 hours to about 88 hours, or from about 10 hours to 72 hours via a continuous intravenous infusion, wherein the intravenous infusion is started after (e.g., from about 1 second to about 1 hour, from about 1 second to about 45 minutes, from about 1 second to about 30 minutes, from about 1 second to about 15 minutes, from about 1 second to about 10 minutes, from about 1 second to about 5 minutes or from about 2 seconds to about 3 minutes after the bolus dose) a bolus dose from about 5 mg to about 100 mg is intravenously administered to the subject.

This disclosure is further directed to a method of treating a subject experiencing non-convulsive EEG seizures comprising administering intravenously from about 450 mg to about 3000 mg ganaxolone over a time period from about 4 hours to about 120 hours at a rate greater than about 10 mg/hour, 15 mg/hour, 20 mg/hour, 25 mg/hour, or 30 mg/hour. In some embodiments from about 2 mg to about 100 mg of ganaxolone is administered via the bolus intravenous injection, and the remainder of dose is administered via a continuous intravenous infusion at a rate greater than 10 mg/hr, 15 mg/hour, 20 mg/hr, 25 mg/hr, or 30 mg/hr for a time period from about 1 hour to about 120 hours.

This disclosure is also directed to a method of treating status epilepticus (e.g., a generalized convulsive status epilepticus, non-convulsive status epilepticus, early status epilepticus, established status epilepticus, refractory status epilepticus, or super-refractory status epilepticus), comprising administering from about 450 mg to about 1000 mg of ganaxolone intravenously to a subject in need thereof for about 24 hours to about 120 hours, and administering a dose of an additional antiepileptic drug during said 24 hours to about 120 hours. The additional antiepileptic drug may be selected from the group consisting benzodiazepines, phenytoin, fosphenytoin, valproic acid, phenobarbital, and/or levetiracetam. In certain embodiments, the antiepileptic drug is a benzodiazepine (e.g., diazepam, lorazepam, etc.). In some of these embodiments, administration of ganaxolone and the additional antiepileptic drug provides a synergistic effect.

This disclosure is also directed to a method of treating Acute Repetitive Seizures (ARS) comprising administering a therapeutically effective amount of ganaxolone intravenously to a subject in need thereof. The therapeutically effective amount may comprise, e.g., from about 1 mg to about 1000 mg of ganaxolone and may be administered as one or more bolus doses, each bolus dose comprising from about 1 mg to about 50 mg, from about 1 mg to about 45 mg, from about 1 mg to about 40 mg, from about 2 mg to about 35 mg, from about 3 mg to about 30 mg, or from about 5 mg to about 30 mg and administered over about 1 to about 5 minutes. In some embodiments, the method further comprises administering, after the one or more bolus doses of ganaxolone, a continuous intravenous infusion of ganaxolone at a rate between about 5 mg/hour and about 130 mg/hour (e.g., from about 5 mg/hour to about 85 mg/hour) for about 24 hours to about 120 hours (e.g., for about 48 hours to about 96 hours), the continuous intravenous infusion started at about the time of the bolus injection or a short time thereafter (e.g., within about 30 min); and lowering the rate of intravenous infusion rate over about 10 hours to about 24 hours (e.g., over 10 hours, about 12 hours, about 14 hours, about 16 hours, about 18 hours, or about 20 hours) before the continuous infusion is stopped.

In certain embodiments, the methods of the invention further comprise administering one or more rescue bolus dose(s) of ganaxolone from about 1 mg to about 50 mg, from about 1 mg to about 45 mg, from about 1 mg to about 40 mg, from about 2 mg to about 35 mg, from about 3 mg to about 30 mg, or from about 5 mg to about 30 mg may be administered intravenously over about 1 to about 5 minutes during the intravenous infusion. The one or more rescue dose(s) may be administered, e.g., in the event there is seizure(s) (i.e., abnormal EEG activity) and/or convulsion(s) relapse. In some embodiments, one, two, three, four or five rescue doses are administered during the intravenous infusion.

In certain embodiments, the methods of the invention comprise administering some or all of the doses of ganaxolone in the form of nanoparticles.

3. BRIEF DESCRIPTION OF THE DRAWINGS

The drawings are not necessarily to scale or exhaustive. Instead, the emphasis is generally placed upon illustrating the principles of the inventions described herein. The accompanying drawings, which constitute a part of the specification, illustrate several embodiments consistent with the disclosure and, together with the description, serve to explain the principles of the disclosure. In the drawings.

4. DETAILED DESCRIPTION

Figure 1:
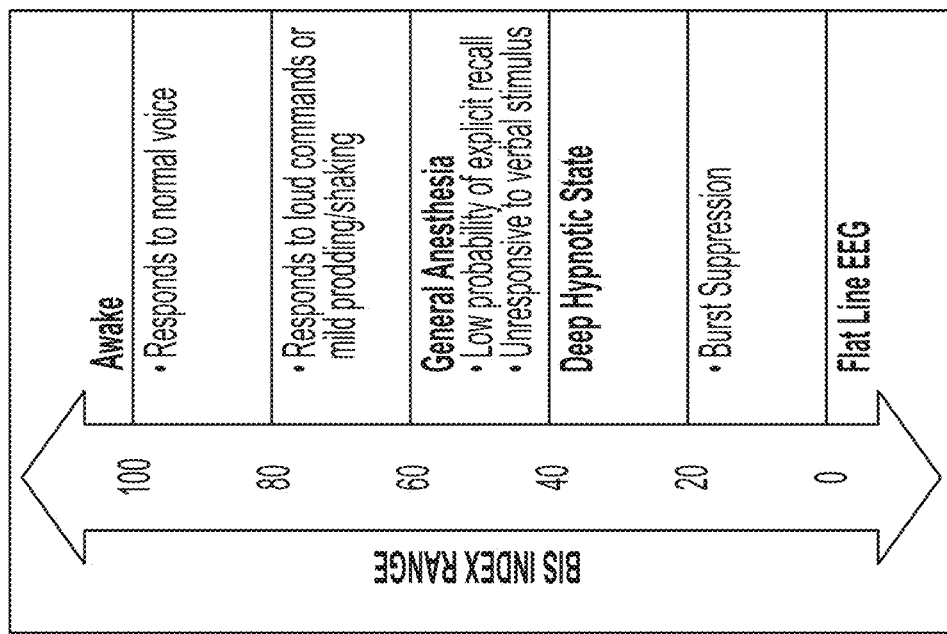
FIG. 1 depicts EEG and BIS changes of the Phase 1 clinical study of Example 1. The changes are consistent with sedative/anesthetic effects of ganaxolone.
Figure 1:
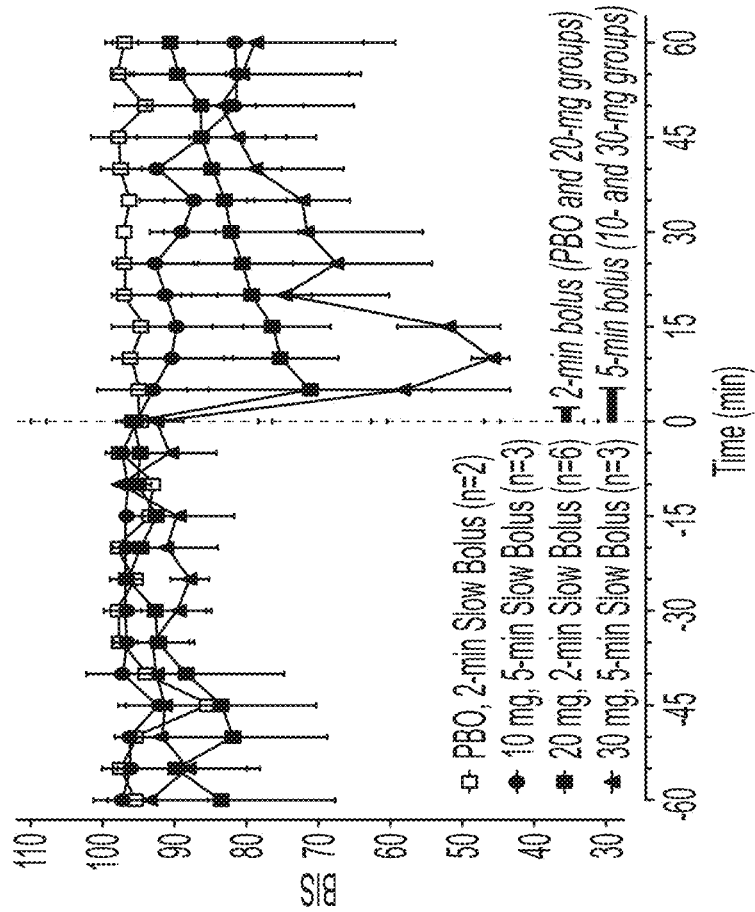

Effectively treating SE has been challenging, and conventional treatment protocols are not effective for many patients. About 50% of subjects fail to respond to treatment with first-line agents, and about 50% of such subjects also fail to respond to treatment with second-line agents, thus progressing to refractory SE. Approximately one third of refractory subjects die and another third recover, but with neurological or other deficits. There is clearly a need for improved methods for treating SE.

The disclosure relates to a new method for treating SE. As exemplified and described herein, treatment according to the method provides rapid SE suppression, and also provides for continued suppression of SE. The method can be used to treat any form of SE, including generalized convulsive SE, non-convulsive SE, refractory SE, and super refractory SE. The method is particularly useful for treating refractory SE. The method can also be used to treat subjects that have failed first-line treatment, second-line treatment, and/or third-line treatment.

SE presents as a prolong seizure for a period of at least 5 minutes or longer or seizures without recovery consciousness between seizures. Suppression of SE typically breaks the seizures (i.e., suppresses or reduces seizure activity). Clinically, suppression of SE can be reduction in seizure burden (i.e., the percent of time during which there is electrographic seizure activity). For instance, a clinician may consider a seizure burden less than 20% suppression of SE and/or a seizure burden that is at least 50% less than during the 30 minutes prior to the initiation of treatment (i.e., intravenous bolus plus continuous intravenous infusion).

The method described herein comprises administering to a subject a therapeutically effective amount of a neurosteroid (e.g., ganaxolone) as an intravenous bolus and a continuous intravenous infusion. The intravenous bolus of ganaxolone is administered in an amount that is sufficient to suppress SE. Typically, a neurosteroid (e.g. ganaxolone) plasma concentration of about 500 ng/ml to about 1000 ng/ml is sufficient to suppress SE. For example, to achieve a ganaxolone plasma concentration of about 500 ng/ml to about 1000 ng/ml, about 30 mg bolus of ganaxolone can be administered. Treatment according to the method lasts for a treatment period, which includes a period during which the continuous intravenous infusion is administered to maintain the subject's serum concentration of neurosteroid (e.g., ganaxolone) at or about a target level (i.e., a target concentration period), and periods during which the subjects plasma concentration of neurosteroid (e.g., ganaxolone) is allowed to or caused to fall below the target concentration, and a taper period during which the patient is weaned off the neurosteroid.

The continuous intravenous infusion of neurosteroid (e.g. ganaxolone) is administered for a target concentration period in an amount sufficient for continued suppression of SE. Continued suppression of SE is achieved when the continuous infusion maintains a plasma concentration of neurosteroid (e.g. ganaxolone) of about 500 ng/ml or higher throughout the target concentration period. The target concentration period is typically at least about 8 hours or at least about 12 hours, although it is possible that the target concentration period can be at least about 4 hours in some subjects. During the target concentration period, the amount of neurosteroid (e.g. ganaxolone) administered to the subject (i.e., by the continuous intravenous infusion) can be increased or decreased to maintain continued suppression of SE, but is sufficient to maintain a plasma concentration of ganaxolone in the subject of at least about 500 ng/ml for at least 4 hours, or preferably about 8 hours following the administration of the intravenous bolus and, optionally throughout the treatment period. Typically, the amount of ganaxolone administered by the continuous intravenous infusion is decreased over a period of about 24 hours from the initiation of the intravenous infusion. For instance, the amount of ganaxolone administered to the subject can be decreased about 2 hours after the initiation of the continuous intravenous infusion, and then about 10 hours to about 14 hours after infusion. Surprisingly, SE continues to be suppressed by the continuous intravenous infusion even though the amount of neurosteroid (e.g. ganaxolone) administered during the continuous intravenous infusion is decreased during the treatment period. As a result, the method provide enhanced safety and efficacy with lower exposure to ganaxolone than was expected. During treatment the subject can be monitored for plasma concentration of neurosteroid (e.g. ganaxolone) and using EEG for seizure activity. If the subject appears to show signs of SE re-lapse, the amount of ganaxolone administered can be adjusted accordingly. For instance, an additional intravenous bolus can be provided or the amount of ganaxolone infused can be increased. The amount of neurosteroid (e.g. ganaxolone) administered during infusion is typically adjusted by increasing or decreasing the infusion rate.

The continuous intravenous infusion is generally administered concurrently with the administration of the intravenous bolus. Although, in some cases, the continuous intravenous infusion can be initiated before or after the intravenous bolus.

The continuous intravenous infusion is typically followed by a taper period during which the subject is weaned off ganaxolone. During the taper period the continuous intravenous infusion of ganaxolone is systematically decreased, typically by reducing the amount of ganaxolone that is administered to the subject (e.g., by the continuous intravenous infusion) by about one third every four hours until the subject no longer requires ganaxolone.

Additional description of the method and guidance for the practice of the method are provided herein. For ease of presentation, further details and guidance are provided with respect to a preferred aspect using ganaxolone. It is intended that the further details and guidance also relate to treatment with other neurosteroids.

a. Intravenous Bolus

The method for treating SE comprises administering to a subject in need thereof an intravenous bolus of ganaxolone in an amount sufficient to suppress SE, which typically is an amount sufficient to produce a ganaxolone plasma concentration of at least about 500 ng/ml to about 1000 ng/ml. Typically the intravenous bolus results in a ganaxolone plasma concentration of about 750 ng/ml to about 1000 ng/ml, and more typically about 1000 ng/ml.

For example, the intravenous bolus of ganaxolone can include an amount of ganaxolone that is sufficient to achieve a ganaxolone plasma concentration of at least about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1000 ng/ml, about 1025 ng/ml, about 1050 ng/ml, about 1075 ng/ml, or about 1100 ng/ml. Preferably, the intravenous bolus achieves a ganaxolone plasma concentration of at least about 500 ng/ml to about 1000 ng/ml.

While a ganaxolone plasma concentration of at least about 500 ng/ml to about 1000 ng/ml is preferable to suppress SE, there can be some variability based on, for example a differences in subjects' weight, metabolism, age, duration of SE and/or severity of SE. Accordingly, a skilled clinician will understand that lower exposure to ganaxolone, such as a plasma concentration of at least about 425 ng/ml, at least about 450 ng/ml, at least about 475 ng/ml, could suppress SE in some SE patients. However, it is preferred that the bolus delivers an amount of ganaxolone that is sufficient to achieve a plasma concentration of ganaxolone of about 1000 ng/ml. A plasma concentration of ganaxolone above about 1000 ng/ml can induce anesthesia in a subject, which is generally not an intended effect or desired outcome of the methods described herein. Preferably, the intravenous bolus of ganaxolone results in minimal or no anesthetic effects. For example, preferably, the amount of ganaxolone administered does not result in loss of consciousness, does not result in paralysis, and/or does not cause deep sedation. Preferably, treatment in accordance with the methods described herein does not require the subject to undergo controlled ventilation and/or endotracheal intubation.

In some instances, a plasma concentration of about 1005 ng/ml, about 1010 ng/ml, 1020 ng/ml, 1030 ng/ml, 1040 ng/ml, 1050 ng/ml, 1060 ng/ml, 1070 ng/ml, 1080 ng/ml, can be achieved to suppress SE without resulting in anesthesia. In other instances, a ganaxolone plasma concentration that is greater than 1000 ng/ml by about 1%, about 2%, about 3%, about 4%, about 5%, about 6%, about 7%, about 8%, about 9%, about 10%, about 11%, about 12%, about 13%, about 14%, or about 15% can be sufficient to suppress SE without resulting in anesthesia.

The intravenous bolus of ganaxolone can be administered (i.e., infused) into the subject at an amount of about 1 mg, about 2 mg, about 3 mg, about 4 mg/hr, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg. Preferably, about 30 mg of ganaxolone is infused into the subject during the intravenous bolus.

In subjects weighing less than about 40 kg, about 0.10 mg/kg, about 0.11 mg/kg, about 0.12 mg/kg, about 0.13 mg/kg, about 0.14 mg/kg, about 0.15 mg/kg, about 0.16 mg/kg, about 0.17 mg/kg, about 0.18 mg/kg, about 0.19 mg/kg, about 0.20 mg/kg, about 0.21 mg/kg, about 0.22 mg/kg, about 0.23 mg/kg, about 0.24 mg/kg, about 0.25 mg/kg, about 0.26 mg/kg, about 0.27 mg/kg, about 0.28 mg/kg, about 0.29 mg/kg, about 0.30 mg/kg, about 0.31 mg/kg, about 0.32 mg/kg, about 0.33 mg/kg, about 0.34 mg/kg, about 0.35 mg/kg, about 0.36 mg/kg, about 0.37 mg/kg, about 0.38 mg/kg, about 0.39 mg/kg, about 0.40 mg/kg, about 0.41 mg/kg, about 0.42 mg/kg, about 0.43 mg/kg, about 0.44 mg/kg, about 0.45 mg/kg, about 0.46 mg/kg, about 0.47 mg/kg, about 0.48 mg/kg, about 0.49 mg/kg, about 0.5 mg/kg, about 0.51 mg/kg, about 0.52 mg/kg, about 0.53 mg/kg, about 0.54 mg/kg, about 0.55 mg/kg, about 0.56 mg/kg, about 0.57 mg/kg, about 0.58 mg/kg, about 0.59 mg/kg, about 0.60 mg/kg, about 0.61 mg/kg, about 0.62 mg/kg, about 0.63 mg/kg, about 0.64 mg/kg, about 0.65 mg/kg, about 0.66 mg/kg, about 0.67 mg/kg, about 0.68 mg/kg, about 0.69 mg/kg, about 0.7 mg/kg, about 0.75 mg/kg, about 0.80 mg/kg, about 0.85 mg/kg, about 0.90 mg/kg, about 0.95 mg/kg of ganaxolone can be infused into the subject during the intravenous bolus. Preferably, about 0.43 mg/kg of ganaxolone is infused into the subject during the intravenous bolus.

The intravenous bolus can be administered to the subject for any desired period of time and is typically administered from about 1 minute to about 10 minutes, such as, from about 1 minute to about 5 minutes, about 1 minute to about 4 minutes, about 1 minute to about 3 minutes, about 1 minute to about 2 minutes, about 2 minutes to about 5 minutes, about 2 minutes to about 4 minutes, about 2 minutes to about 3 minutes, about 3 minutes to about 5 minutes, or about 3 minutes to about 4 minutes. The intravenous bolus can preferably be administered to the subject for about 1 minute, about 2 minutes, about 3 minutes, or about 5 minutes. More preferably, the intravenous bolus is administered to the subject for about 3 minutes.

In instances when a ganaxolone plasma concentration of at least about 500 ng/ml is not achieved after the intravenous bolus of ganaxolone, the subject may be administered an additional intravenous bolus of ganaxolone to achieve a ganaxolone plasma concentration of at least about 500 ng/ml, and preferably about 1000 ng/ml.

b. Continuous Intravenous Infusion

The continuous intravenous infusion of ganaxolone is administered periprocedural with the intravenous bolus. For instance, the continuous intravenous infusion can be initiated concurrently with the administration of the intravenous bolus. Alternatively, the continuous intravenous infusion can be initiated before or after the administration of the intravenous bolus. Typically, the intravenous infusion and continuous intravenous infusion is administered from the same ganaxolone source (e.g., and intravenous bag connect to IV line) and are initiated concurrently. The continuous intravenous infusion of ganaxolone is administered in an amount to continue SE suppression throughout the treatment period and beyond. The continuous intravenous infusion of ganaxolone provides durable suppression of SE that lasts preferably through the treatment period, preferably through the taper period, preferably after the taper period, and preferably post-treatment.

In embodiments, the continuous intravenous infusion of ganaxolone achieves suppression of SE for at least 1 hour, at least 2 hours, at least 3 hours, at least 4 hours, at least 5 hours, at least 6 hours at least 7 hours, at least 8 hours, at least 9 hours, at least 10 hours, at least 11 hours, at least 12 hours, at least 1 day, at least 2 days, at least 3 days, at least 4 days, at least 5 days, at least 6 days, at least 7 days or longer post-treatment. In embodiments, the continuous intravenous infusion of ganaxolone achieves suppression of SE for at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks or longer post-treatment. In embodiments, the continuous intravenous infusion of ganaxolone achieves suppression of SE for at least 1 month, at least 2 months, at least 3 months, at least 4 months, at least 5 months, at least 6 months, at least 7 months, at least 8 months, at least 9 months, at least 10 months, at least 11 months, at least 12 months or longer post-treatment.

Continued SE suppression is achieved by administering to the subject a continuous intravenous infusion in an amount sufficient to produce a ganaxolone plasma concentration of at least about 500 ng/ml for a target concentration period, which typically is at least about 4 hours, or preferably at least about 8 hours or at least about 12 hours following the administration of the intravenous bolus, and optionally throughout the treatment period. In practice, the patient's plasma concentration of ganaxolone can be monitored and the amount of ganaxolone that is infused can be adjusted or titrated to maintain a plasma concentration of at least about 500 ng/ml throughout the treatment period. A ganaxolone plasma concentration of at least about 500 ng/ml period, for example for about 4 hours, about 5 hours about 6 hours, about 7 hours, about 8 hours, about 9 hours, about 10 hours, about 11 hours, about 12 hours or longer can achieve continued SE suppression.

The continuous intravenous infusion of ganaxolone can be administered to the subject in an amount to achieve a ganaxolone plasma concentration of about 500 ng/ml to about 1000 ng/ml for at least 4 hours, and preferably at least about 8 hours or at least about 12 hours.

While a plasma concentration of at least about 500 ng/ml is preferable for continued SE suppression, there can be some variability based on, for example, differences in subjects' weight, metabolism, age, duration of SE and/or severity of SE. Accordingly, a skilled clinician will understand that, for example, a ganaxolone plasma concentration of at least about 425 ng/ml, at least about 450 ng/ml, at least about 475 ng/ml can be sufficient for continued SE suppression in some SE subjects. A ganaxolone plasma concentration less than 400 ng/ml or less than 500 ng/mL will typically not be sufficient for continued SE suppression. In embodiments, the continuous intravenous infusion of ganaxolone achieves a ganaxolone plasma concentration of about 425 ng/ml, about 450 ng/ml, about 475 ng/ml, about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1000 ng/ml, about 1025 ng/ml, about 1050 ng/ml, about 1075 ng/ml, or about 1100 ng/ml. Preferably, a ganaxolone plasma concentration of about 500 ng/ml to about 1000 ng/ml is desired.

A plasma concentration of ganaxolone above about 1000 ng/ml can induce anesthesia in a subject, which is generally not an intended effect or desired outcome of the methods described herein. Preferably, the continuous intravenous infusion of ganaxolone results in minimal or no anesthetic effects. For example, preferably, the amount of ganaxolone administered does not result in loss of consciousness, does not result in paralysis, and/or does not cause deep sedation. Preferably, treatment in accordance with the methods described herein does not require the subject to undergo controlled ventilation and/or endotracheal intubation.

In some instances, a ganaxolone plasma concentration of about 1005 ng/ml, about 1010 ng/ml, 1020 ng/ml, 1030 ng/ml, 1040 ng/ml, 1050 ng/ml, 1060 ng/ml, 1070 ng/ml, 1080 ng/ml, can result in continued SE suppression without causing anesthesia. In instances, a ganaxolone plasma concentration less than about 1%, less than about 2%, less than about 3%, less than about 4%, less than about 5%, less than about 6%, less than about 7%, less than about 8%, less than about 9%, less than about 10%, less than about 11%, less than about 12%, less than about 13%, less than about 14%, or less than about 15% of 500 ng/ml can be sufficient to suppress SE. In other instances, a ganaxolone plasma concentration greater about 1%, than about 2%, bout 3%, about 4%, about 5%, about 6%, about 7%, about 8%, about 9%, about 10%, about 11%, about 12%, about 13%, about 14%, or about 15% of 1000 ng/ml can be sufficient for continued SE suppression without resulting in anesthesia.

The amount of ganaxolone administered to the subject per hour by continuous intravenous infusion can be decreased over the continuous intravenous infusion treatment period. In instances, the continuous intravenous infusion can be decreased over a period of about 24 hours from the initiation of the intravenous infusion. For example, the amount of ganaxolone administered to the subject per hour by continuous intravenous infusion can be decreased about 1 hour, about 1.5 hours, about 2 hours, about 2.5 hours, about 3 hours, about 3.5 hours, about 4 hours, about 4.5 hours, about 5 hours, about 6 hours, about 7 hours, about 8 hours, about 9 hours, about 10 hours, about 11 hours, about 12 hours, about 14 hours, about 15 hours, about 16 hours, about 17 hours, about 18 hours, about 19 hours, about 20 hours, about 21 hours, about 22 hours, about 23 hours, or about 24 hours after the initiation of the continuous intravenous infusion.

The amount of ganaxolone administered to the subject per hour by continuous intravenous infusion can be decreased or further decreased at one or more periods over the continuous intravenous infusion treatment period. For example, the amount of ganaxolone administered to the subject per hour by continuous intravenous infusion can be decreased at one interval, two intervals, three intervals, four intervals, five intervals or more during the continuous intravenous infusion treatment period. In the methods provided herein, the amount of ganaxolone administered to the subject per hour by continuous intravenous infusion is preferably decreased at two time intervals over about 24 hours from the initiation of the continuous intravenous infusion.

The amount of ganaxolone administered to the subject per hour by continuous intravenous infusion can be deceased or further decreased between about 1 hours to about 5 hours, about 1 hour to about 4 hours, about 1 hour to about 3 hours, about 2 hours to about 3 hours, about 2 hours to about 4 hours, about 2 hours to about 4 hours, about 2 hours to about 5 hours, about 3 hours to about 4 hours, about 4 hours to about 5 hours after the initiation of the continuous intravenous infusion. The amount of ganaxolone administered to the subject per hour by continuous intravenous infusion is preferably decreased about 2 hours after the initiation of the continuous intravenous infusion.

The amount of ganaxolone administered to the subject per hour by continuous intravenous infusion can be decreased or further decreased about 8 hours to about 16 hours, about 8 hours to about 15 hours, about 8 hours to about 14 hours, about 8 hours to about 13 hours, about 8 hours to about 12 hours, about 8 hours to about 11 hours, about 8 hours to about 10 hours, about 9 hours to about 16 hours, about 9 hours to about 15 hours, about 9 hours to about 14 hours, about 9 hours to about 13 hours, about 9 hours to about 12 hours, about 9 hours to about 11 hours, about 9 hours to about 10 hours, about 10 hours to 16 hours, about 10 hours to about 15 hours, about 10 hours to about 14 hours, about 10 hours to about 13 hours, about 10 hours to about 12 hours, about 10 hours to about 11 hours after the initiation of the continuous intravenous infusion. The amount of ganaxolone administered to the subject per hour by continuous intravenous infusion is preferably decreased at about 10 hours to about 14 hours after the initiation of the continuous intravenous infusion. More specifically, the amount of ganaxolone administered to the subject per hour by continuous intravenous infusion is decreased at about 12 hours after the initiation of the continuous intravenous infusion.

The amount of ganaxolone administered to the subject per hour by continuous intravenous infusion can be decreased between about 1 hours to about 5 hours, about 1 hour to about 4 hours, about 1 hour to about 3 hours, about 2 hours to about 3 hours, about 2 hours to about 4 hours, about 2 hours to about 4 hours, about 2 hours to about 5 hours, about 3 hours to about 4 hours, about 4 hours to about 5 hours after the initiation of the continuous intravenous infusion, and then about 8 hours to about 16 hours, about 8 hours to about 15 hours, about 8 hours to about 14 hours, about 8 hours to about 13 hours, about 8 hours to about 12 hours, about 8 hours to about 11 hours, about 8 hours to about 10 hours, about 9 hours to about 16 hours, about 9 hours to about 15 hours, about 9 hours to about 14 hours, about 9 hours to about 13 hours, about 9 hours to about 12 hours, about 9 hours to about 11 hours, about 9 hours to about 10 hours, about 10 hours to 16 hours, about 10 hours to about 15 hours, about 10 hours to about 14 hours, about 10 hours to about 13 hours, about 10 hours to about 12 hours, about 10 hours to about 11 hours after the initiation of the continuous intravenous infusion.

The amount of ganaxolone administered to the subject per hour by continuous intravenous infusion is preferably decreased at about 2 hours after the initiation of the continuous intravenous infusion, and then about 10 hours to about 14 hours after the initiation of the continuous intravenous infusion.

The amount of ganaxolone administered to the subject per hour by continuous intravenous infusion can be decreased by about 40%, about 45%, about 50%, about 55%, about 65%, about 75%, about 80%, about 85%, or about 90% relative to the amount administered per hour at the initiation of the continuous intravenous infusion.

In embodiments, the amount of ganaxolone administered to the subject per hour by continuous intravenous infusion can be decreased by about 40%, about 45%, about 50%, about 55%, about 65%, about 75%, about 80%, about 85%, or about 90%, relative to the amount administered per hour at the initiation of the continuous intravenous infusion, about 1 hour, about 1.5 hours, about 2 hours, about 2.5 hours, about 3 hours, about 3.5 hours, about 4 hours, about 4.5 hours, about 5 hours, about 6 hours, about 7 hours, about 8 hours, about 9 hours, about 10 hours, about 11 hours, about 12 hours, about 14 hours, about 15 hours, about 16 hours, about 17 hours, about 18 hours, about 19 hours, about 20 hours, about 21 hours, about 22 hours, about 23 hours, or about 24 hours after the initiation of the continuous intravenous infusion.

The amount of ganaxolone administered to the subject per hour by continuous intravenous infusion can be decreased by about 40%, about 45%, about 50%, about 55%, or about 60% relative to the amount administered per hour at the initiation of the continuous intravenous infusion, about 1 hour to about 5 hours after the initiation of the continuous intravenous infusion. The amount of ganaxolone administered to the subject per hour by continuous intravenous is preferably decreased by about 50%, relative to the amount administered per hour at the initiation of the continuous intravenous infusion, about 2 hours after the initiation of the continuous intravenous infusion.

The amount of ganaxolone administered to the subject per hour by continuous intravenous infusion can be decreased by about 50%, about 55%, about 60%, about 65%, about 70%, about 75%, about 80%, or about 85% relative to the amount administered per hour at the initiation of the continuous intravenous infusion, about 10 hours to about 14 hours after the initiation of the continuous intravenous infusion. The amount of ganaxolone administered to the subject per hour by continuous intravenous infusion is preferably decreased by about 75%, relative to the amount administered per hour at the initiation of the continuous intravenous infusion, about 10 hours after the initiation of the continuous intravenous infusion.

The continuous intravenous infusion comprises infusing into the subject about 10 mg, about 15 mg, about 20 mg, about 25 mg, about 30 mg, about 35 mg, about 40 mg, about 45 mg, about 50 mg, about 60 mg, about 65 mg, about 70 mg, about 80 mg, about 85 mg, about 90 mg, about 95 mg, or about 100 mg of ganaxolone per hour during the continuous intravenous infusion. Preferably, the continuous intravenous infusion comprises infusing into the subject about 20 mg of ganaxolone per hour to about 80 mg of ganaxolone per hour during the continuous infusion treatment period.

In embodiments, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, or about 89 mg, about 90 mg of ganaxolone are infused into the subject at the initiation of the continuous intravenous infusion. About 80 mg of ganaxolone per hour is preferably infused into the subject at the initiation of the continuous intravenous infusion. The amount of ganaxolone can then be decreased to about 60 mg, about 55 mg, about 40 mg, about 35 mg, about 30 mg, about 25 mg, about 20 mg, about 15 mg, or about 10 mg. Preferably the amount of ganaxolone is decreased to about 40 mg of ganaxolone and then about 20 mg of ganaxolone during the treatment period.

In embodiments, about 40 mg of ganaxolone per hour is administered to the subject by continuous intravenous infusion starting about 2 hours after initiation of the continuous intravenous infusion and for about 6 hours to about 10 hours thereafter. In embodiments, about 20 mg of ganaxolone per hour is administered to the subject by continuous intravenous infusion starting about 12 hours after initiation of the continuous intravenous infusion and for about 12 hours to about 24 hours thereafter. If desired or medically indicated, the amount of ganaxolone infused into the subject by continuous intravenous infusion can be increased up to about 45 mg of ganaxolone per hour starting about 24 hours after initiation and for up to about 12 hours thereafter. In general, the amount of ganaxolone administered to the subject by continuous intravenous infusion does not exceed 45 mg ganaxolone per hour.

The amount of ganaxolone administered to the subject per hour by continuous intravenous infusion can be decreased or increased by increasing or decreasing the rate of infusion. The rate of infusion will generally vary between about 5 mg/hour of ganaxolone to about 130 mg/hour of ganaxolone, depending on clinical response and safety. In certain embodiments, the rate of administration is from about 5 mg/hour to about 90 mg/hour.

The treatment period of the continuous intravenous infusion can be for a period of at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 31 hours, at least 32 hours, at least 33 hours, at least 34 hours, at least 35 hours, at least 36 hours, at least 37 hours, at least 38 hours, at least 39 hours, at least 40 hours after the initiation of the continuous intravenous infusion. A preferred continuous intravenous infusion period is for a period of about 8 hours to about 36 hours after the initiation of the continuous intravenous infusion. Generally, the continuous intravenous infusion is a period of about 36 hours but can be longer, such as for about 48 hours, about 72 hours, or about 96 hours.

During continuous intravenous infusion of ganaxolone, one or more additional intravenous bolus of ganaxolone can be administered to a subject that shows signs of SE re-lapse or experiences SE re-lapse. Electroencephalogram (EEG) can be used to detect signs of SE re-lapse. Plasma concentration of ganaxolone can alternatively or in combination with EEG be used to detect signs of SE re-lapse or a subject that experiences SE re-lapse. For example, a ganaxolone plasma concentration below 400 ng/ml can suggest that the subject is likely to re-lapse.

One or more additional intravenous bolus of ganaxolone from about 1 mg to about 100 mg, from about 1 mg to about 90 mg, about 1 mg to about 80 mg, about 2 mg to about 75 mg, from about 3 mg to about 70 mg, from about 5 mg to about 60 mg, from about 5 mg to about 50 mg, from about 5 mg to about 45 mg, or from about 5 mg to about 35 mg may be administered intravenously over about 1 to about 5 minutes, e.g., in the event there is seizure(s) (i.e., abnormal EEG activity) and/or convulsion(s) relapse.

The additional intravenous bolus of ganaxolone can be infused into the subject at an amount of about 1 mg/hr, about 2 mg/hr, about 3 mg/hr, about 4 mg/hr, about 5 mg/hr, about 6 mg/hr, about 7 mg/hr, about 8 mg/hr, about 9 mg/hr, about 10 mg/hr, about 11 mg/hr, about 12 mg/hr, about 13 mg/hr, about 14 mg/hr, about 15 mg/hr, about 16 mg/hr, about 17 mg/hr, about 18 mg/hr, about 19 mg/hr, about 20 mg/hr, about 21 mg/hr, about 22 mg/hr, about 23 mg/hr, about 24 mg/hr, about 25 mg/hr, about 26 mg/hr, about 27 mg/hr, about 28 mg/hr, about 29 mg/hr, about 30 mg/hr, about 31 mg/hr, about 32 mg/hr, about 33 mg/hr, about 34 mg/hr, about 35 mg/hr, about 36 mg/hr, about 37 mg/hr, about 38 mg/hr, about 39 mg/hr, about 40 mg/hr, about 45 mg/hr, about 50 mg/hr, about 55 mg/hr, about 60 mg/hr, about 65 mg/hr, about 70 mg/hr, about 75 mg/hr, about 80 mg/hr, about 85 mg/hr, about 90 mg/hr, about 95 mg/hr, or about 100 mg/hr of ganaxolone per hour prior to seizure re-lapse or upon detection of seizure re-lapse over a period of about 1 minute to about 5 minutes.

c. Taper Period

The method for treating SE can further comprise continuing to administer to a subject in need thereof the continuous intravenous infusion for a taper period. The taper period follows the target concentration period. Generally, the taper period immediately follows the continuous intravenous infusion treatment period. Although, in some cases, the taper period can immediately follow the target concentration period. When the continuous intravenous has a treatment period of about 36 hours or longer (i.e., 8 hours, about 72 hours, or about 96 hours), the taper period starts immediately after the treatment period.

During the taper period the amount of ganaxolone administered to the subject per hour is reduced by about 5%, about 10%, about 15%, about 20%, about 25%, about 30%, about 35%, about 40%, about 50% or more about every 1 hour, about 2 hours, about 3 hours, about 4 hours, about 5 hours, about 6 hours, about 7 hours, about 8 hours, about 9 hours, about 10 hours, about 11 hours, or about 12 hours until the subject is weaned off ganaxolone.

During the taper period the amount of ganaxolone administered to the subject per hour is reduced by about one third about every 1 hour, about 2 hours, about 3 hours, about 4 hours, about 5 hours, about 6 hours, about 7 hours, about 8 hours, about 9 hours, about 10 hours, about 11 hours, or about 12 hours. Preferably, during the taper period the amount of ganaxolone administered to the subject per hour is reduced by about one third about every four hours.

The taper period can be for a period of at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 32 hours, at least about 36 hours, at least about 48 hours, at least about 72 hours, at least about 96 hours, or longer until the subject is weaned off ganaxolone.

As an alternative, the continuous intravenous infusion can be stopped, and oral ganaxolone can be administered to the subject. Oral ganaxolone can be used in place of the taper period to maintain a ganaxolone serum concentration of about 200 ng/ml to about 400 ng/ml.

In certain embodiments, the methods disclosed herein further comprise, after stopping the continuous intravenous infusion of ganaxolone, orally administering ganaxolone to the subject. The oral daily dose of ganaxolone may be, e.g., from about 200 mg to about 3000 mg, from about 400 mg to about 2000 mg, from about 600 mg to about 1900 mg, or from about 900 mg to about 1800 mg, and may be administered in an oral capsule, oral suspension or an oral tablet. In certain embodiments, the oral daily dose of ganaxolone may be, e.g., from about 200 mg to about 2000 mg, from about 400 mg to about 1500 mg, from about 400 mg to about 1250 mg, or from about 400 mg to about 1000 mg, and may be administered in an oral capsule, oral suspension or an oral tablet. The oral administration may continue, e.g., for about 7 days, 14 days, 21 days, 28 days or longer.

In certain embodiments, one or more oral doses of ganaxolone are administered before or after the continuous intravenous infusion or intravenous doses of ganaxolone. The oral daily dose of ganaxolone may be, e.g., from about 200 mg to about 3000 mg, from about 400 mg to about 2000 mg, from about 600 mg to about 1900 mg, or from about 900 mg to about 1800 mg, and may be administered in an oral capsule, oral suspension or an oral tablet. In certain embodiments, the oral daily dose of ganaxolone may be, e.g., from about 200 mg to about 2000 mg, from about 400 mg to about 1500 mg, from about 400 mg to about 1250 mg, or from about 400 mg to about 1000 mg, and may be administered in an oral capsule, oral suspension or an oral tablet. The oral administration may continue, e.g., for about 7 days, 14 days, 21 days, 28 days or longer.

The methods of the present invention encompass, e.g., administration of one or more intravenous bolus of ganaxolone, followed by administration ganaxolone via an continuous intravenous infusion; administration of one or more intravenous bolus of ganaxolone, followed by administration ganaxolone via a continuous intravenous infusion; and followed by administration of ganaxolone orally, e.g., in an oral capsule, an oral tablet, an oral suspension, or an oral solution; administration of ganaxolone orally, e.g., in an oral capsule, an oral tablet, an oral suspension or an oral solution, followed by administration of ganaxolone via a continuous intravenous infusion; administration of ganaxolone orally, e.g., in an oral capsule, an oral tablet, an oral suspension or an oral solution, followed by administration of ganaxolone via a continuous intravenous infusion, wherein one or more intravenous bolus of ganaxolone is administered during the intravenous infusion; administration of ganaxolone orally, e.g., in an oral capsule, an oral tablet, an oral suspension or an oral solution, followed by administration of ganaxolone via one or more intravenous bolus of ganaxolone, and followed by administration of ganaxolone via a continuous intravenous infusion; administration of ganaxolone orally, e.g., in an oral capsule, an oral tablet, an oral suspension or an oral solution, followed by administration of ganaxolone via one or more intravenous bolus injection(s), followed by administration of ganaxolone via a continuous intravenous infusion, and followed by administration of ganaxolone orally, e.g., in an oral capsule, an oral tablet, an oral suspension or an oral solution, etc.

c. Additional Details and Guidance for Practicing the Method

The amount of ganaxolone administered intravenously in the methods of the present invention may vary, e.g., from about 0.25 mg to about 3000 mg (e.g., about 1 mg, 2 mg, 3 mg, 4 mg, 5, mg, 7.5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, 220 mg, 240 mg, 250 mg, 260 mg, 270 mg, 280 mg, 290 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 725 mg, 750 mg, 775 mg, 800 mg, 850 mg, 900 mg, 950 mg, 1000 mg, etc.).

The total daily dose of ganaxolone administered in the methods of the present invention may vary from about 450 mg to about 1000 mg. In certain embodiments, the total daily dose of ganaxolone is from about 500 mg to about 900 mg, from about 500 mg to about 875 mg, from about 525 mg to about 875 mg, from about 525 mg to about 850 mg, from about 525 mg to about 825 mg, from about 525 mg to about 800 mg, from about 525 mg to about 775 mg, from about 525 mg to about 750 mg, or from about 525 mg to about 725 mg.

In certain embodiments, the amount of ganaxolone administered is based on the subject's weight. A subject weighing less than 40 kg, may receive a bolus dose from about 0.07 mg/kg to about 1.43 mg/kg (e.g., from about 0.125 mg/kg to about 0.4 mg/kg) (over 1 to 5 minutes); and, thereafter, a continuous infusion at a rate from about 0.8 mg/kg/hour to about 2 mg/kg/hour for about 1 to 3 hours; and, thereafter, a continuous infusion at a rate from about 0.6 mg/kg/hour to about 1 mg/hr for about 4 to 8 hours; and, thereafter, at a rate from about 0.15 mg/kg/hour to about 0.4 mg/kg/hour for 13 to 19 hours. At the end of the 24 hours of continuous infusion, the infusion rate may be increased to, e.g., a rate from about 0.2 mg/kg/hour to about 0.6 hour for 24 to 48 hours or 24 to 96 hours. The dose may then be tampered by 10 to 25% every 6 hours and then discontinued. In some embodiments, the dose is reduced by about 25% every 6 hours (75%, 50%, and 25%) and then discontinued. In some embodiments, the taper is from 12 to 24 hours.

A subject weighing 40 kg or more, may receive a bolus dose from about 5 mg to about 100 mg (over about 1 to 5 minutes), and then a continuous infusion from about 60 mg/hour to about 160 mg/hour for 1 to 4 hours; followed by a continuous infusion rate from about 20 mg/hour to about 140 mg/hour for 4 to 8 hours; and, thereafter, at a rate from about 10 mg/hour to about 120 mg/hour for 12 to 19 hours. At the end of the first 24 hours of continuous infusion, the infusion rate may be increased for 24 to 48 hours or 24 to 96 hours. The dose may then be tampered by 10 to 25% every 6 hours and then discontinued. In some embodiments, the dose is reduced by about 25% every 6 hours (75%, 50%, and 25%) and then discontinued. In some embodiments, the taper is from 12 to 24 hours.

In certain embodiments, the methods of the invention comprise administering some or all of the doses of ganaxolone in the form of nanoparticles. Preparation and compositions of the exemplary nanoparticles are described in the Formulation section below.

In the embodiments, where the subject receives the drug for less than 2 hours or progresses to an IV anesthetic drug (a 3rd line treatment) for seizure suppression, tapering of the dose is not required, and the methods of the invention do not comprise a tapering step.

In some methods of the invention, ganaxolone dose, or a portion thereof, is administered through a dedicated (peripheral or central) IV line.

The duration of treatment may vary, e.g., from about 30 minutes to about 120 hours. In certain embodiments, the treatment duration is about 1 to about 5 days (e.g., about 24 hours, about 36 hours, about 48 hours, about 72 hours, about 96 hours, or about 120 hours). In certain embodiments, the treatment includes a taper period of from about 10 hours to about 24 hours (e.g., an 18-hour taper). In certain embodiments, treatment is continued until the subject achieves a seizure burden improvement of about 100.

Seizure burden is defined by the number of seizures in the entire duration of the EEG collection during the first 2 days of treatment. This will be compared to the seizure burden from the pre-dose EEG (up to 24 hours prior to study drug initiation through immediately prior to study drug administration). If a pre-dose EEG is not available the calculation should be done from the start of the EEG collection through the end of the first 2 days.

In certain embodiments, seizure burden assessed as duration of electrographic seizure activity per hour of EEG recording collected.

In certain embodiments, the seizure burden improvement is calculated about 12 to about 60 hours after the initiation of therapy.

If the seizure burden calculation indicates that the subject is unlikely to benefit from additional administration (e.g., if the partial seizure burden improvement is about 100%), the dosage may be tapered over 12 to 24 hours (e.g., 18 hours). Conversely, if the seizure burden calculation indicates that the subject may likely to benefit (e.g., if the partial seizure burden improvement is between 33-50%), administration of ganaxolone will continue for an additional time period (e.g., 24 to 48 hours). At the end of the additional time period, the subject may be reassessed and/or the dose of ganaxolone may be tapered over 12 to 24 hours (e.g., 18 hours).

For subjects who receive study drug for less than 2 hours and/or if at any time during study drug administration the subject progresses to an IV anesthetic (a 3rd line treatment) for seizure suppression no dose taper is required.

A. Methods for Treating SE

The disclosure relates to methods for treating SE comprising administering to a subject in need thereof an intravenous bolus of ganaxolone and a continuous intravenous infusion of ganaxolone. Preferred methods for treating SE comprise administering to a subject an intravenous bolus of ganaxolone in an amount sufficient to suppress SE and a continuous intravenous infusion for continued SE suppression. SE presents as a prolong seizure for a period of at least 5 minutes or without recovery between seizures. Suppression of SE typically breaks the seizures (i.e., suppresses or reduces the seizure activity). Clinically, suppression of SE can be reduction in seizure burden (i.e., the percent of time during which there is electrographic seizure activity). For instance, a clinician may consider a seizure burden less than 20% suppression of SE and/or a seizure burden that is at least 50% less than during the 30 minutes prior to the initiation of treatment (i.e., intravenous bolus plus continuous intravenous infusion).

The human subject might be male, female, adults, and children, seniors (65 and older). The human subject may be, e.g., from about 1 year to about 120 years old, from about 1 year to about 100 years old, from about 2 years to about 95 years old, from about 5 years to about 90 years old, from about 7 years to about 85 years old, from about 10 years old to about 85 years old, from about 12 years old to about 85 years old, from about 14 years old to about 85 years old, from about 16 years old to about 85 years old, from about 18 years old to about 85 years old, or from about 20 years old to about 85 years old.

SE can be classified into three subtypes: generalized convulsive SE, non-convulsive SE, and refractory SE. Generalized convulsive status epilepticus is the most commonly encountered form of SE and is characterized by convulsions that are associated with tonic-clonic movements of the extremities and mental status impairment. Nonconvulsive SE is defined as SE activity seen on EEG without clinical symptoms. Refractory SE occurs in subjects who do not respond to the standard SE treatment regimen of a first-line treatment and a second-line treatment. Each of these subtypes are suitable for treatment according to the methods described herein.

A subject suitable for treatment according to the methods described herein has and/or is experiencing status epilepticus. For example, but not limited to a generalized convulsive status epilepticus, non-convulsive status epilepticus, early status epilepticus, established status epilepticus, refractory status epilepticus, or super-refractory status epilepticus. A subject having refractory SE is particularly suitable for the treatment according to the methods described herein.

Treatment of SE typically occurs in stages, first-line, second-line, and third-line. The first-line standard of case treatment is parental benzodiazepines. Exemplary benzodiazepines include but are not limited to clonazepam, lorazepam, midazolam, and diazepam. Benzodiazepines are ineffective in about 35%-45% of cases. If SE continues despite treatment with benzodiazepines, other anti-seizure medications (e.g., fosphenytoin, levetiracetam, and valproate) are administered as a second-line treatment. In approximately 50% of cases are refractory to second-line treatment. In instances when SE continues despite first-line and second-line treatment, general anesthetics (e.g., thiopental, propofol, and midazolam) are used as third-line treatment. About 31%-41% of subjects with SE develop refractory SE. The use of third-line agents usually result in iatrogenic coma, which necessitates protection of the airways by intubation and mechanical ventilation. Further, use of general anesthetics is associated with high morbidity and approximately 35% mortality.

In embodiments, the SE subject to be treated in accordance with the methods provided herein has failed first-line treatment, second-line treatment, or third-line treatment. In other embodiments, the SE subject to be treated has failed first-line treatment and second-line treatment. In other embodiments, the SE subject to be treated has failed first-line treatment, second-line treatment and third-line treatment. A subject having SE can be treated according to the methods provided herein prior to receiving other treatments, such as standard of care first-line or second-line treatments. Alternatively the subject can be treated according to the methods provided herein after failure of first-line treatment (e.g., benzodiazepines). In some instances, the subject is to be treated according to the methods provided herein after failure of second-line treatment (e.g., an anti-seizure drug). The subject to be treated according to the methods provided herein may have failed one or more anti-seizure drugs. In other instances, the subject to be treated according to the methods provided herein may have failed third-line treatment (e.g., anesthetics). The subject to be treated according to the methods disclosed herein may have failed first-line treatment (e.g., benzodiazepine) and two or more second line second-line treatments. For instance, the subject may have failed two or more anti-seizure drugs. Exemplary anti-seizure drugs can include, but are not limited to, fosphenytoin/phenytoin, valproic acid, levetiracetam, lacosamide, or brivaracetam.

Super refractory status epilepticus is characterized by status epileptic seizures that persist despite treatment with a first line therapy, a second line therapy, and a general anesthetic for 24 hours or more. These patients are severely ill and will likely die without any further intervention. To treat these patients, it is recognized that a larger amount of ganaxolone may be required. To successfully treat these subjects according to the methods described herein an intravenous bolus of ganaxolone is administered to achieve a ganaxolone plasma concentration of about 800 mg/ml to about 1200 mg/ml and a continuous intravenous infusion of ganaxolone in an amount to achieve a ganaxolone plasma concentration of about 800 mg/ml to about 1200 mg/ml.

In certain embodiments, the subject does not have a refractory genetic condition selected from the group consisting of PCDH19-related epilepsy, CDKL5 Deficiency Disorder (CDD), Dravet Syndrome, Lennox-Gastaut syndrome (LGS), Continuous Sleep Wave in Sleep (CSWS), Epileptic Status Epilepticus in Sleep (ESES), and other intractable and refractory genetic epilepsy conditions that clinically resemble PCDH19-related epilepsy, CDKL5 Deficiency Disorder, Dravet Syndrome, LGS, CSWS, and ESES. In certain embodiments, the subject does not have CDKL5 gene disorder. In certain embodiments, the subject does not have PCDH19-related epilepsy.

B. Ganaxolone

Ganaxolone (alternatively known as 3α-hydroxy-3β-methyl-5α-pregnan-20-one, SPT3162, MD 9150000, CCD-1042, Mepalon, and 1042) is the subject of Investigational New Drug Application (IND) No. 129,433. The molecular formula of ganaxolone is $C_{22}H_{36}O_2$, and the chemical structure is:

c.

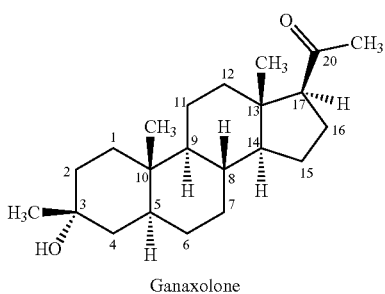

Ganaxolone

Ganaxolone (3α-hydroxy-3β-methyl-5α-pregnan-20-one) is a 3β-methylated synthetic analogue of the endogenous neurosteroid allopregnanolone with similar biological activity (Carter et al., (1997), The Journal of Pharmacology and Experimental Therapeutics, 280:1284-1295), but it is designed to not activate nuclear (classical) progesterone receptors. Also, in contrast to allopregnanolone, ganaxolone is orally bioavailable.

Ganaxolone acts as a positive allosteric modulator of γ-aminobutyric acid type A (GABAA) receptors in the CNS (Carter et al 1997). Ganaxolone affects GABAA receptors by interacting with a recognition site that is distinct from other allosteric GABAA receptor modulators, such as benzodiazepines and barbiturates. Ganaxolone binds to synaptic- and extrasynaptic receptors, mediating both phasic and tonic modulation, respectively. The unique binding of ganaxolone to these two distinct receptor types does not lead to the tolerance seen with benzodiazepines (Mares and Stehlikova (2010) Neurosci. Let. 469:396-399) and allows ganaxolone to act as a broad-spectrum GABAergic compound with the potential to treat the myriad of symptoms related to pediatric genetic epilepsies, refractory seizures, cognitive and behavioral disorders, and sleep dysfunction.

Ganaxolone provides an alternative mechanism in the treatment of seizures and could serve as effective therapy in the management of SE, including generalized convulsive status epilepticus, non-convulsive status epilepticus, early status epilepticus, established status epilepticus, refractory status epilepticus, or super-refractory status epilepticus.

Ganaxolone does not activate the progesterone receptor directly or indirectly, via metabolic conversion, confirming ganaxolones lack of hormonal activity.

Ganaxolone has the advantage of controlling both convulsive and non-convulsive seizures. In experimental animals, Ganaxolone produced immediate and prolonged cessation of benzodiazepine-resistant SE as evidenced by a block of convulsions, reduction of EEG seizure activity, and increased survival.

Ganaxolone is insoluble in water. Its solubility in 95% alcohol, propylene glycol and polyethylene glycol are 13 mg/mL, 3.5 mg/mL and 3.1 mg/mL, respectively. Ganaxolone has a relatively long half-life—approximately 20 hours in human plasma following oral administration (Nohria, V. and Giller, E., *Neurotherapeutics*, (2007) 4(1): 102-105). Furthermore, ganaxolone has a short $T_{max}$, which means that therapeutic blood levels are reached quickly.

Ganaxolone is metabolized by CYP3A4/5, and in vitro data and human PK data from subjects taking strong CYP inducers (carbamazepine and phenytoin) has shown increased ganaxolone clearance with approximately a 45% lowering in overall ganaxolone levels and exposure.

In the ganaxolone development program overall, no clinically significant trends in electrocardiogram (ECG) intervals, vital signs, or physical or neurological examinations have been noted, and no mean changes from baseline in clinical laboratory results have been identified. In the completed placebo-controlled Phase 1, 2, and 3 studies, 0.32% of subjects who received ganaxolone and 0.46% of subjects who received placebo developed elevated LFTs during the study (>3×ULN AST and/or ALT). A subject participating in the ganaxolone paediatric epilepsy study developed liver failure, which was not considered to be related to ganaxolone. The subject was diagnosed with short bowel syndrome, liver steatosis and IgG-cholangitis, which were considered to be the causal factors for the subject's liver failure. There have been no other cases of Hy's Law or liver failure in the ganaxolone development program. It is known that ganaxolone and its metabolites are excreted to breast milk. After cessation of the dosing, plasma ganaxolone levels are expected to drop rapidly, but it is possible that low sub-therapeutic levels persist for several days as ganaxolone is slowly released from tissues.

Previous toxicology studies in animals focusing on prenatal and neonatal development have not demonstrated toxicities associated with ganaxolone. Ganaxolone has been administered to infants with severe forms of epilepsy as early as 4 months of age. In clinical trials involving administration of ganaxolone over several weeks, the study drug has been tapered off over a 1 to 2-week period. There have been no reports of withdrawal symptoms emerging after cessation of ganaxolone.

D. Formulations

Contemplated herein are formulations that comprise a therapeutically effective amount of a neurosteroid for treating status epilepticus according the methods disclosed herein. Preferably the neurosteroid is ganaxolone. Other neurosteroid that can be used according to the methods disclosed herein include, but are not limited to allopregnanolone, 3α-Dihydroprogesterone, 5α-Dihydroprogesterone, 5β-Dihydroprogesterone, Allopregnanediol, Dihydrodeoxycorticosterone, Pregnanediol, Pregnanolone, Tetrahydrodeoxycorticosterone, Alfadolone, Alfadolone acetate, EIDD-036, Hydroxydione, Minaxolone, 21-chloro-2β-morpholin-4-yl-5β-pregnan-3α-ol-20-one, 2β-(2,2-dimethyl-4-morpholinyl)-3α-hydroxy-11,20-dioxo-5α-pregnan-21-yl methanesulfonate, or Renanolone, SGE-516, SGE-872, SAGE-217 (Zuranolone: 3α-hydroxy-3β-methyl-21-(4-cyano-1H-pyrazol-1'-yl)-19-nor-5β-pregnan-20-one).

The formulation is preferably an intravenous formulation of ganaxolone. The intravenous formulation of ganaxolone can comprise a cyclodextrin (e.g., a sulfobutyl ether β-cyclodextrin (Captisol®). The IV solution can comprise a sterile ready to administer solution containing 1 mg/ml ganaxolone in Captisol® (Captisol®:GNX ratio 60:1). The ready to administer solution can comprise 1 mg/ml ganaxolone in sulfobutyl ether β-cyclodextrin (Captisol®), a Captisol to ganaxolone ratio of 60:1, and a buffer (i.e., phosphate and/or sodium chloride). In embodiments, the IV solution is a sterile solution containing 3 mg/ml ganaxolone in Captisol® (Sulfobutylether-β-Cyclodextrin) (Captisol®:GNX ratio 70:1) or 5 mg/ml ganaxolone in Captisol, each of which may or may not be may be diluted with 0.9% saline (i.e., sodium chloride) solution, for example to produce a 1 mg/ml ganaxolone solution for administration, prior to administration.

In certain embodiments, the formulation (e.g., an intravenous formulation) comprises ganaxolone and sulfobutylether-β-cyclodextrin (e.g., Captisol®) in a weight ratio from about 1:50 to about 1:75. In some of these embodiments, the weight ratio ganaxolone and Captisol® is about 1:51, about 1:52, about 1:53, about 54:1, about 1:55, about 1:56, about 1:57, about 1:58, about 1:59, about 1:60, about 1:61, about 1:62, about 1:63, about 1:64, about 1:65, about 1:66, about 1:67, about 1:68, about 1:69, about 1:70, about 1:71, or about 1:72. In some of these embodiments, the weight ratio ganaxolone and Captisol® is about 1:60.

The intravenous formulation may be selected, e.g., from the group consisting of nanocrystal formulations; emulsions; lyocells; solvents or surfactants; liposomes; microemulsions; and liquids containing solid-lipid nanoparticles.

In certain embodiments, the intravenous formulation is an IV solution. An intravenous formulation is preferably a sterile liquid (e.g., aqueous liquid in the form of an emulsion, a suspension, a solution and the likes). In some of these embodiments, the IV solution comprises ganaxolone and a pharmaceutically acceptable solvent(s) and/or oil(s) that can solubilize ganaxolone.

In certain embodiments, the intravenous formulation is an oil-in-water emulsion.

In certain embodiments, the intravenous formulation is a liquid nanoparticulate formulation (e.g., a liquid comprising nanoparticles of ganaxolone). In some of the embodiments, the nanoparticulate formulation comprises ganaxolone and a polymeric and/or ionic stabilizer, and is free from complexing agents. In certain embodiments, the polymeric and ionic stabilizers are selected from the group consisting of surfactants. In certain embodiments, surfactants are selected from the group consisting of sorbitan esters, polyoxyethylene sorbitan fatty acid esters, poloxamers, cholesterol salts, and bile salts.

In certain embodiments, the formulation for the intravenous infusion may be a formulation as described and prepared in U.S. Patent Publication No. 2017/0258812 or U.S. Patent Publication No. 2016/0228454. However, formulations for the intravenous infusion may be prepared in accordance with other methods known to those skilled in the art.

As described in U.S. Patent Publication No. 2016/0228454, an aqueous injectable ganaxolone formulation may comprise a) ganaxolone and sulfobutyl ether-β-cyclodextrin in an inclusion complex; and b) water. In some embodiments, the complex comprising ganaxolone and sulfobutyl ether-β-cyclodextrin comprises a 1:1 ganaxolone: sulfobutyl ether-β-cyclodextrin complex; and the w/w ratio of sulfobutyl ether-β-cyclodextrin to ganaxolone is about 52:1 or greater. In some embodiments, the formulation may further comprise surfactant. In some embodiments, the surfactant is a sorbitan ester, a polyoxyethylene sorbitan fatty acid ester, a poloxamer, a cholesterol salt, or a bile salt. In some embodiments, the surfactant may comprise from about 1 to about 15 percent of the formulation by weight. In some embodiments, the surfactant is polysorbate 80. In some embodiments, the formulation further comprises a buffer and has a pH of about 6.0 to about 7.6. In some embodiments, the buffer is a phosphate buffer. In some embodiments, the buffer is a combination of a monobasic phosphate buffer and a dibasic phosphate buffer, wherein the concentration of each phosphate buffer is 2 mM to 50 mM. In some embodiments, the buffer is a phosphate buffer. In some embodiments, the buffer is a combination of a monobasic phosphate buffer and a dibasic phosphate buffer, wherein the concentration of each phosphate buffer is 2 mM to 50 mM. In some embodiments, the concentration of ganaxolone is 2 mg/ml to 8 mg/ml, the w/w ratio of sulfobutyl ether-β-cyclodextrin to ganaxolone is within the range from about 52:1 to about 90:1; the formulation contains a buffer and has a pH of 6.7 to 7.3 or a pH of 6.0 to 7.0; and the formulation contains from 1 to 15 weight percent surfactant. In some embodiments, the concentration of ganaxolone is 1 mg/ml to 5 mg/ml; the weight percent of sulfobutyl ether-β-cyclodextrin 25% to 35%; and the formulation contains from 5% to 15% (weight percent) of at least one of the following: a surfactant, ethanol, glycerin, or propylene glycol. In some embodiments, the formulation further comprises a preservative. In some embodiments, the preservative is benzyl alcohol, chlorbutanol, 2-ethoxyethanol, parabens (including methyl, ethyl, propyl, butyl, and combinations), benzoic acid, sorbic acid, chlorhexidene, phenol, 3-cresol, thimerosal, or a phenylmercurate salt.

As further described in U.S. Patent Publication No. 2016/0228454, the formulation may be a lyophilized ganaxolone formulation comprising ganaxolone and sulfobutyl ether-β-cyclodextrin, wherein the ganaxolone formulation is 1.0% to 1.5% ganaxolone. In some embodiments, the formulation may further comprise a bulking agent. In some embodiments, the bulking agent is mannitol, lactose, sucrose, trehalose, sorbitol, rafinose, glucose, glycine, histidine, polyethylene glycol (PEG), or polyvinyl pyrrolidone (PVP).

Ganaxolone formulations suitable for parenteral administration in the methods of the present invention may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propylene glycol, polyethyleneglycol, glycerol, cremophor and the like), suitable mixtures thereof, vegetable oils (such as olive oil) and injectable organic esters such as ethyl oleate. Additionally, ganaxolone can be dissolved at concentrations of >1 mg/ml using water soluble beta cyclodextrins (e.g. beta-sulfobutyl-cyclodextrin and 2-hydroxypropylbetacyclodextrin). A particularly suitable cyclodextrin is a substituted-β-cyclodextrin is Captisol®. Proper fluidity can be maintained, for example, by the use of a coating such as lecithin, by the maintenance of the required particle size in the case of dispersions, and by the use of surfactants. Ganaxolone formulations suitable for subcutaneous injection may also contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, sorbic acid, and the like. It may also be desirable to include isotonic agents, such as sugars, sodium chloride, and the like. Prolonged drug absorption of the injectable pharmaceutical form can be brought about by the use of agents delaying absorption, such as aluminum monostearate and gelatin. Ganaxolone suspension formulations designed for extended release via subcutaneous or intramuscular injection can avoid first pass metabolism and lower dosages of ganaxolone will be necessary to maintain plasma levels of about 50 ng/ml. In such formulations, the particle size of the ganaxolone particles and the range of the particle sizes of the ganaxolone particles can be used to control the release of the drug by controlling the rate of dissolution in fat or muscle.

In certain embodiments, the intravenous formulation is a solution comprising a complexing agent(s). In some of these embodiments, a complexing agent is a molecule with a lipophilic core and hydrophilic outer shell capable of solubilizing ganaxolone In certain embodiments, the formulation is an IV solution comprising ganaxolone and sulfobutylether cyclodextrin (Captisol®), wherein ganaxolone is solubilized in sulfobutylether cyclodextrin (Captisol®). In some embodiments, the solution comprises 3 mg of ganaxolone per 1 ml of the solution and is sterile. In certain embodiments, the solution is stable for at least 18 months, is stored refrigerated at a temperature from about 4° C. to about 8° C.

In certain embodiments, the liquid formulation of the present invention may be a formulation as described and prepared in U.S. Pat. No. 8,022,054, entitled "Liquid Ganaxolone Formulations and Methods for the Making and Use Thereof" However, the oral liquid (e.g., suspension) formulation of ganaxolone may be prepared in accordance with other methods known to those skilled in the art.

As described in U.S. Pat. No. 8,022,054, the liquid formulation may be an aqueous dispersion of stabilized particles comprising ganaxolone, a hydrophilic polymer, a wetting agent, and an effective amount of a complexing agent that stabilizes particle growth after an initial particle growth and endpoint is reached, the complexing agent selected from the group of small organic molecules having a molecular weight less than 550 and containing a moiety selected from the group consisting of a phenol moiety, an aromatic ester moiety and an aromatic acid moiety, wherein the stabilized particles have a volume weighted median diameter (D50) of the particles from about 50 nm to about 500 nm, the complexing agent being present in an amount from about 0.05% to about 5%, w/w based on the weight of particles, the particles dispersed in an aqueous solution which further contains at least two preservatives in an amount sufficient to inhibit microbial growth. The hydrophilic polymer may be in an amount from about 3% to about 50%, w/w, based on the weight of the solid particles. The wetting agent may be an amount from about 0.01% to about 10%, w/w, based on the weight of the solid particles. Ganaxolone may be in an amount from about 10% to about 80% (and in certain embodiments form about 50% to about 80%) based on the weight of the stabilized particles. The stabilized particles may exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm. The stabilized particles may exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SIF is less than about 750 nm.

The complexing agent can be any molecule with a lipophilic core and hydrophilic outer shell capable of solubilizing ganaxolone. In certain embodiments, complexing agent can be a substance containing a phenol moiety, an aromatic ester moiety or an aromatic acid moiety. In certain embodiments, complexing agents are selected from the group consisting of parabens, organic acids, carboxylic acids, aromatic acids, aromatic esters, acid salts of amino acids, methyl anthranilate, sodium metabisulphite, ascorbic acid and its derivatives, malic acid, isoascorbic acid, citric acid, tartaric acid, sodium sulphite, sodium bisulphate, tocopherol, water- and fat-soluble derivatives of tocopherol, sulphites, bisulphites and hydrogen sulphites, para-aminobenzoic acid and esters, 2,6-di-t-butyl-alpha-dimethylamino-p-cresol, t-butylhydroquinone, di-t-amylhydroquinone, di-t-butylhydroquinone, butylhydroxytoluene (BHT), butylhydroxyanisole (BHA), pyrocatechol, pyrogallol, propyl/gallate, nordihydroguaiaretic acid, phosphoric acids, sorbic and benzoic acids, esters, ascorbyl palmitate, derivatives and isomeric compounds thereof, pharmaceutically acceptable salts thereof, and mixtures thereof. In certain embodiments, the complexing agent is selected from the group consisting of a paraben, benzoic acid, phenol, sodium benzoate, methyl anthranilate, and the like. The hydrophilic polymer may be a cellulosic polymer, a vinyl polymer and mixtures thereof. The cellulosic polymer may be a cellulose ether, e.g., hydroxypropylmethylcellulose. The vinyl polymer may be polyvinyl alcohol, e.g., vinyl pyrrolidone/vinyl acetate copolymer (S630). The wetting agent may be sodium lauryl sulfate, a pharmaceutically acceptable salt of docusate, and mixtures thereof. The aqueous dispersion may further comprise a sweetener, e.g., sucralose. In certain embodiments, the preservative is selected from the group consisting of potassium sorbate, methylparaben, propylparaben, benzoic acid, butylparaben, ethyl alcohol, benzyl alcohol, phenol, benzalkonium chloride, and mixtures of any of the foregoing.

In some embodiments, liquid ganaxolone formulations are provided comprising the ganaxolone particles described herein and at least one dispersing agent or suspending agent for oral administration to a subject. The ganaxolone formulation may be a powder and/or granules for suspension, and upon admixture with water, a substantially uniform suspension is obtained. As described herein, the aqueous dispersion can comprise amorphous and non-amorphous ganaxolone particles of consisting of multiple effective particle sizes such that ganaxolone particles having a smaller effective particle size are absorbed more quickly and ganaxolone particles having a larger effective particle size are absorbed more slowly. In certain embodiments, the aqueous dispersion or suspension is an immediate release formulation. In another embodiment, an aqueous dispersion comprising amorphous ganaxolone particles is formulated such that about 50% of the ganaxolone particles are absorbed within about 3 hours after administration and about 90% of the ganaxolone particles are absorbed within about 10 hours after administration. In other embodiments, addition of a complexing agent to the aqueous dispersion results in a larger span of ganaxolone containing particles to extend the drug absorption phase such that 50-80% of the particles are absorbed in the first 3 hours and about 90% are absorbed by about 10 hours.

A suspension is "substantially uniform" when it is mostly homogenous, that is, when the suspension is composed of approximately the same concentration of ganaxolone at any point throughout the suspension. Preferred embodiments are those that provide concentrations essentially the same (within 15%) when measured at various points in a ganaxolone aqueous oral formulation after shaking. Especially preferred are aqueous suspensions and dispersions, which maintain homogeneity (up to 15% variation) when measured 2 hours after shaking. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

In some embodiments, ganaxolone formulations are powders for aqueous dispersion and comprise stable ganaxolone particles having an effective particle size by weight of less than 500 nm formulated with ganaxolone particles having an effective particle size by weight of greater than 500 nm. In such embodiments, the formulations have a particle size distribution wherein about 10% to about 100% of the ganaxolone particles by weight are between about 75 nm and about 500 nm, about 0% to about 90% of the ganaxolone particles by weight are between about 150 nm and about 400 nm, and about 0% to about 30% of the ganaxolone particles by weight are greater than about 600 nm. The ganaxolone particles describe herein can be amorphous, semi-amorphous, crystalline, semi-crystalline, or mixture thereof.

In one embodiment, the aqueous suspensions or dispersions described herein comprise ganaxolone particles or ganaxolone complex at a concentration of about 20 mg/ml to about 150 mg/ml of suspension. In another embodiment, the aqueous oral dispersions described herein comprise ganaxolone particles or ganaxolone complex particles at a concentration of about 25 mg/ml to about 75 mg/ml of solution. In yet another embodiment, the aqueous oral dispersions described herein comprise ganaxolone particles or ganaxolone complex at a concentration of about 50 mg/ml of suspension. The aqueous dispersions described herein are especially beneficial for the administration of ganaxolone to infants (less than 2 years old), children under 10 years of age and any patient group that is unable to swallow or ingest solid oral dosage forms.

Liquid ganaxolone formulation for oral administration can be aqueous suspensions selected from the group including, but not limited to, pharmaceutically acceptable aqueous oral dispersions, emulsions, solutions, and syrups. See, e.g., Singh et al., Encyclopedia of Pharmaceutical Technology, 2nd Ed., pp. 754-757 (2002). In addition to ganaxolone particles, the liquid dosage forms may comprise additives, such as: (a) disintegrating agents; (b) dispersing agents; (c) wetting agents; (d) at least one preservative, (e) viscosity enhancing agents, (f) at least one sweetening agent, (g) at least one flavoring agent, (h) a complexing agent, and (i) an ionic dispersion modulator. In some embodiments, the aqueous dispersions can further comprise a crystalline inhibitor.

Examples of disintegrating agents for use in the aqueous suspensions and dispersions include, but are not limited to, a starch, e.g., a natural starch such as corn starch or potato starch, a pregelatinized starch such as National 1551 or Amijele®, or sodium starch glycolate such as Promogel® or Explotab®; a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crosspovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 9080, also known as Poloxamine 9080, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908%).

Wetting agents (including surfactants) suitable for the aqueous suspensions and dispersions described herein are known in the art and include, but are not limited to, acetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carpool 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben) and their salts, benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth. In one embodiment, the aqueous liquid dispersion can comprise methylparaben and propylparaben in a concentration ranging from about 0.01% to about 0.3% methylparaben by weight to the weight of the aqueous dispersion and 0.005% to 0.03% propylparaben by weight to the total aqueous dispersion weight. In yet another embodiment, the aqueous liquid dispersion can comprise methylparaben 0.05 to about 0.1 weight % and propylparaben from 0.01-0.02 weight % of the aqueous dispersion.

Suitable viscosity enhancing agents for the aqueous suspensions or dispersions described herein include, but are not limited to, methyl cellulose, xanthan gum, carboxymethylcellulose, hydroxypropyl cellulose, hydroxypropylmethyl cellulose, Plasdone® S-630, carbomer, polyvinyl alcohol, alginates, acacia, chitosans and combinations thereof. The concentration of the viscosity enhancing agent will depend upon the agent selected and the viscosity desired.

Examples of natural and artificial sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet®. Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.0001% to about 10.0% the weight of the aqueous dispersion. In another embodiment, the aqueous liquid dispersion can comprise a sweetening agent or flavoring agent in a concentration ranging from about 0.0005% to about 5.0% wt % of the aqueous dispersion. In yet another embodiment, the aqueous liquid dispersion can comprise a sweetening agent or flavoring agent in a concentration ranging from about 0.0001% to 0.1 wt %, from about 0.001% to about 0.01 weight %, or from 0.0005% to 0.004% of the aqueous dispersion.

In addition to the additives listed above, the liquid ganaxolone formulations can also comprise inert diluents commonly used in the art, such as water or other solvents, solubilizing agents, and emulsifiers.

In some embodiments, the ganaxolone formulations can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art include, but are not limited to, for example, U.S. Pat. Nos. 5,858,401, 6,667,048, and 6,960, 563.

Exemplary emulsifiers are ethyl alcohol, isopropyl alcohol, ethyl carbonate, ethyl acetate, benzyl alcohol, benzyl benzoate, propylene glycol, 1,3-butyleneglycol, dimethylformamide, sodium lauryl sulfate, sodium docusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In certain preferred embodiments, the liquid pharmaceutical formulation comprising ganaxolone, hydroxypropyl methylcellulose, polyvinyl alcohol, sodium lauryl sulfate, simethicone, methyl paraben, propyl paraben, sodium benzoate, citric acid, and sodium citrate at pH 3.8-4.2. The suspension may comprise ganaxolone at a concentration of 50 mg/ml. The formulation may further comprise a pharmaceutically acceptable sweetener (e.g., sucralose) and/or a pharmaceutically acceptable flavorant (e.g., cherry). The formulation may be enclosed, e.g., in a 120 mL, 180 mL, 240 mL, or 480 mL bottle.

A formulation for oral administration may be an oral solid dosage form (e.g., an oral capsule or tablet) or a liquid (e.g., an oral suspension comprising ganaxolone). In certain embodiments, the oral suspension is administered to the patient via the use of an oral syringe.

In certain embodiments, the liquid formulation of the present invention may be a formulation as described and prepared in Applicant's prior U.S. Pat. No. 8,022,054, entitled "Liquid Ganaxolone Formulations and Methods for the Making and Use Thereof." However, the oral liquid (e.g., suspension) formulation of ganaxolone may be prepared in accordance with other methods known to those skilled in the art.

In certain preferred embodiments, the oral solid formulation of the present invention may be a formulation as described and prepared in Applicant's prior U.S. Pat. No. 7,858,609, entitled "Solid Ganaxolone Formulations and Methods for the Making and Use Thereof." However, the oral solid dosage formulation of ganaxolone may be prepared in accordance with other methods known to those skilled in the art.

For example, as disclosed in U.S. Pat. No. 7,858,609, the oral solid formulation may comprise stabilized particles comprising ganaxolone, a hydrophilic polymer, a wetting agent, and an effective amount of a complexing agent that stabilizes particle growth after an initial particle growth and endpoint is reached, the complexing agent being a small organic molecule having a molecular weight less than 550 and containing a moiety selected from the group consisting of a phenol moiety, an aromatic ester moiety and an aromatic acid moiety, wherein the stabilized particles have a volume weighted median diameter (D50) of the particles is from about 50 nm to about 500 nm, the complexing agent being present in an amount from about 0.05% to about 5% w/w, based on the weight particles of the solid. The hydrophilic polymer may be in an amount from about 3% to about 50%, w/w, based on the weight of the solid particles. The wetting agent may be an amount from about 0.01% to about 10%, w/w, based on the weight of the solid particles. Ganaxolone may be in an amount from about 10% to about 80% (and in certain embodiments form about 50% to about 80%) based on the weight of the stabilized particles. The stabilized particles may exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm. The stabilized particles may exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SIF is less than about 750 nm. The solid stabilized particles may be combined with optional excipients and prepared for administration in the form of a powder, or they may be incorporated into a dosage form selected from the group consisting of a tablet or capsule. The complexing agent may be a paraben, benzoic acid, phenol, sodium benzoate, methyl anthranilate, and the like. The hydrophilic polymer may be a cellulosic polymer, a vinyl polymer and mixtures thereof. The cellulosic polymer may be a cellulose ether, e.g., hydroxypropymethylcellulose. The vinyl polymer may be polyvinyl alcohol, e.g., vinyl pyrrolidone/vinyl acetate copolymer (S630). The wetting agent may be sodium lauryl sulfate, a pharmaceutically acceptable salt of docusate, and mixtures thereof. When the particles are incorporated into a solid dosage form, the solid dosage form may further comprise at least one pharmaceutically acceptable excipient, e.g., an ionic dispersion modulator, a water soluble spacer, a disintegrant, a binder, a surfactant, a plasticizer, a lubricant, a diluent and any combinations or mixtures thereof. The water soluble spacer may be a saccharide or an ammonium salt, e.g., fructose, sucrose, glucose, lactose, mannitol. The surfactant may be, e.g., polysorbate. The plasticizer may be, e.g., polyethylene glycol. The disintegrant may be cross-linked sodium carboxymethylcellulose, crospovidone, mixtures thereof, and the like.

A capsule may be prepared, e.g., by placing the bulk blend ganaxolone formulation, described herein, inside of a capsule. In some embodiments, the ganaxolone formulations (non-aqueous suspensions and solutions) are placed in a soft gelatin capsule. In other embodiments, the ganaxolone formulations are placed in standard gelatin capsules or non-gelatin capsules such as capsules comprising HPMC. In other embodiments, the ganaxolone formulations are placed in a sprinkle capsule, wherein the capsule may be swallowed whole or the capsule may be opened and the contents sprinkled on food prior to eating. In some embodiments of the present invention, the therapeutic dose is split into multiple (e.g., two, three, or four) capsules. In some embodiments, the entire dose of the ganaxolone formulation is delivered in a capsule form.

In certain embodiments, each capsule contains either 200 mg or 225 mg ganaxolone, and hydroxypropyl methylcellulose, sucrose, polyethylene glycol 3350, polyethylene glycol 400, sodium lauryl sulfate, sodium benzoate, citric acid anhydrous, sodium methyl paraben, microcrystalline cellulose, 30% Simethicone Emulsion, gelatin capsules, polysorbate 80, and sodium chloride. In some of the embodiments, the size of the capsule is 00.

Alternatively, the oral dosage forms of the present invention may be in the form of a controlled release dosage form, as described in U.S. Pat. No. 7,858,609.

In certain preferred embodiments, the oral solid formulation of the present invention may be a formulation as described and prepared U.S. Pat. No. 8,367,651.

As described in U.S. Pat. No. 8,367,651, solid stabilized particles may comprise ganaxolone, a hydrophilic polymer, a wetting agent, and an effective amount of a complexing agent that stabilizes particle growth after an initial particle growth and endpoint is reached, the complexing agent being a small organic molecule having a molecular weight less than 550 and containing a moiety selected from the group consisting of a phenol moiety, an aromatic ester moiety and an aromatic acid moiety, wherein the stabilized particles have a volume weighted median diameter (D50) of the particles is from about 50 nm to about 500 nm and the concentration of ganaxolone in the solid stabilized particles is at least 50% by weight. The hydrophilic polymer maybe in an amount from about 3% to about 50%, w/w, based on the weight of the solid particles. The wetting agent may be in an amount from about 0.01% to about 10%, w/w, based on the weight of the solid particles. In some of the embodiments, the stabilized particles exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm. In some embodiments, the stabilized particles exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SIF is less than about 750 nm. In some embodiments, ganaxolone may be present in an amount greater than 50% to about 80%, based on the weight of the particles. In some embodiments, the stabilized particles may exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour, as compared to the D50 of the stabilized particles when the particles are dispersed in distilled water under the same conditions, wherein the volume weighted median diameter (D50) of the stabilized particles dispersed in SGF or SIF is less than about 750 nm. In some embodiments, the solid stabilized particles may be in the form of a powder. In some embodiments, the particles may be incorporated into a dosage form selected from the group consisting of a tablet or capsule. In some embodiments, the volume weighted median diameter (D50) of the stabilized particles dispersed in distilled water is from about 100 nm to about 350 nm. In some embodiments, the complexing agent is selected from the group consisting of parabens, benzoic acid, methyl anthranilate, and pharmaceutically acceptable salts thereof and mixtures thereof. In some embodiments, paraben is selected from the group consisting of methylparaben, ethylparaben, propylparaben, pharmaceutically acceptable salts thereof and mixtures thereof. In some embodiments, the hydrophilic polymer is selected from the group consisting of a cellulosic polymer, a vinyl polymer and mixtures thereof. In some embodiments, the cellulosic polymer is a cellulose ether. In some embodiments, the cellulose ether is hydroxypropylmethylcellulose. In some embodiments, the vinyl polymer is polyvinyl alcohol. In some embodiments, the wetting agent is selected from the group consisting of sodium lauryl sulfate, a pharmaceutically acceptable salt of docusate, and mixtures thereof. Is some embodiments, the particles are incorporated into a solid dosage form, further comprising at least one pharmaceutically acceptable excipient selected from the group consisting of an ionic dispersion modulator, an water soluble spacer, a disintegrant, a binder, a surfactant, a plasticizer, a lubricant, and any combinations or mixtures thereof. In some embodiments, the pharmaceutically acceptable excipient comprises an ionic dispersion modulator. In some embodiments, the ionic dispersion modulator is in an amount from about 1% to about 50%, w/w, based on the weight of the solid particles. In some embodiments, the ionic dispersion modulator is a salt. In some embodiments, the ionic dispersion modulator is an inorganic salt is selected from the group consisting of a magnesium salt, a calcium salt, a lithium salt, a potassium salt, a sodium salt and mixtures thereof. In some embodiments, the ionic dispersion modulator is an organic salt is selected from the group consisting of a citrate salt, a succinate salt, a fumarate salt, a malate salt, maleate salt, a tartrate salt, a glutarate salt, a lactate salt and mixtures thereof. In some embodiments, the pharmaceutically acceptable excipient comprises a water soluble spacer. In some embodiments, the water soluble spacer is in an amount from about 2% to about 60%, w/w, based on the weight of the solid particles. In some embodiments, the water soluble spacer is a saccharide or an ammonium salt. In some embodiments, the saccharide is selected from the group consisting of fructose, sucrose, glucose, lactose, mannitol and mixtures thereof. In some embodiments, the disintegrant is selected from the group consisting of cross-linked sodium carboxymethylcellulose, crospovidone and any combinations or mixtures thereof. In some embodiments, the surfactant is a polysorbate. In some embodiments, the plasticizer is polyethylene glycol. In some embodiments, the solid dosage form is an immediate release dosage form. In some embodiments, the solid dosage form is a controlled release dosage form. In some embodiments, the particles are incorporated into an oral solid dosage form comprising (i) a controlled release component comprising a first portion of the stabilized particles; and a controlled release material, and (ii) an immediate release component comprising a second portion of the stabilized particles, the first and second portion of stabilized particles having a volume weighted median diameter (D50) of from about 50 nm to about 500 nm. In some embodiments, the ratio of ganaxolone in controlled release to immediate release is from about 4:1 to about 1:4. In some embodiments, the dosage form provides a therapeutic effect for about 8 to about 24 hours after administration. In some embodiments, the complexing agent is in an amount from about 0.05% to about 5%, w/w, based on the weight of the solid particles. In some embodiments, the complexing agent comprises methylparaben or a salt thereof. In some embodiments, the complexing agent comprises benzoic acid or a salt thereof. In some embodiments, the complexing agent comprises methyl anthranilate. In some embodiments, the formulation includes from about 200 mg to about 800 mg ganaxolone.

As further described in U.S. Pat. No. 8,367,651, solid stabilized particles may also comprise ganaxolone, a hydrophilic polymer, a wetting agent, and an effective amount of a complexing agent selected from the group of small organic molecules having a molecular weight less than 550 and containing a moiety selected from the group consisting of a phenol moiety, an aromatic ester moiety and an aromatic acid moiety, the stabilized particles having a volume weighted median diameter (D50) of the particles from about 50 nm to about 500 nm, the concentration of ganaxolone in the solid stabilized particles being at least 50% by weight. In some embodiments, ganaxolone is present in an amount greater than 50% to about 80%, based on the weight of the particles. In some embodiments, the particles are incorporated into a dosage form selected from the group consisting of a tablet or capsule. In some embodiments, the complexing agent is selected from the group consisting of parabens, benzoic acid, methyl anthranilate, and pharmaceutically acceptable salts thereof and mixtures thereof.

In certain preferred embodiments, the formulation of the present invention may be a pharmaceutical composition described in U.S. Pat. No. 9,029,355.

In certain embodiments, the composition may comprise the ganaxolone nanoparticles as described above, further in formulations as described in U.S. Pat. No. 9,029,355. In some embodiments, the pharmaceutical composition is a compressed tablet. In some embodiments, the pharmaceutical composition is contained inside a capsule.

E. Combination

In certain embodiments, an additional antiepileptic drug is administered before, during or after the continuous intravenous infusion of ganaxolone. Examples of additional antiepileptic drugs that may be administered are provided in the Additional Antiepileptic Drugs section below. In some embodiments, the additional antiepileptic drug may be selected from the group consisting benzodiazepines, phenytoin, fosphenytoin, valproic acid, phenobarbital, and/or levetiracetam. In some embodiments, the antiepileptic drug is a benzodiazepine (e.g., diazepam, lorazepam, etc.).

In certain embodiments, the additional antileptic drug administered along with ganaxolone is selected from the group consisting of chlordesmethyldiazepam, loreclezole, methsuximide, dipropylacetamide, pheneturide, 2-fluoro-2-phenyl-1,3-propanediyl dicarbamate, ethylphenylhydantoin, 6-methoxytryptoline, N-desmethylclobazam, anthranilic acid, Org 2766, sulthiame, dimethadione, 2-(2,3-dicarboxycyclopropyl)glycine, NCS 382, pipequaline, bretazenil, denzimol, stiripentol, progabide acid, brivaracetam, U 54494A, epidiolex, bromides, mephenytoin, ethosuximide, trimethadione, mebeverine, 5-(2-cyclohexylidene-ethyl)-5-ethyl-barbiturate, 2-propyl-2-pentenoic acid, neo-kyotorphin, 4-phenyl-perhydropyrrole(1,2-a)pyrazine-1,3-dione, alpha-hexachlorocyclohexane, abecarnil, tramiprosate, thioperamide, DN 1417, remacemide, bemethyl, taglutimide, N-(4,4-diphenyl-3-butenyl)nipecotic acid, gaboxadol, ZK 93423, PD 117302, ZK 93426, indeloxazine, milacemide, primidone, ZK 91296, ezogabine, kavain, vanillin, neurotropin, fosphenytoin, zaleplon, CGP 39551, 2-amino-7-phosphonoheptanoic, 2-amino-4-phosphonobutyric acid, 3-(2-carboxypiperazin-4-yl)propyl-1-phosphonic acid, 2-amino-4-methyl-5-phosphono-3-pentenoic acid, rimcazole, angelicin, tiagabine, levetiracetam, zonisamide, paraldehyde, 2,3-piperidinedicarboxylic acid, 6-(1H-imidazol-1-yl)-7-nitro-2,3(1H,4H)-quinoxalinedione, eslicarbazepine acetate, vigabatrin, 1-(4-chlorophenyl)-4-piperidin-1-yl-1,5-dihydroimidazol-2-one, glutamic acid diethyl ester, fludiazepam, gidazepam, ethotoin, mephobarbital, acetazolamide, NNC 711, indol-3-yl pyruvic acid, rufinamide, topiramate, clonazepam, tiletamine, riluzole, progabide, deramciclane, doramectin, chlormethiazole, L 701324, clorazepate dipotassium, lacosamide, thiopental, valproic acid, felbamate, 2,3-dioxo-6-nitro-7-sulfamoylbenzo(f)quinoxaline, 7-nitroindazole, GYKI 52466, phenazepam, 4-amino-3-phenylbutyric acid, eperisone, sidnocarb, ryodipine, nimetazepam, nitrazepam, meprobamate, clobazam, estazolam, lorazepam, benzobarbital, magnesium sulfate, tizanidine, lamotrigine, flunarizine, pregabalin, gabapentin, phenytoin, phenobarbital, oxcarbazepine, carbamazepine, medazepam, pharmaceutically acceptable salts thereof, and mixtures of any of the foregoing.

In certain embodiments, the additional antileptic drug administered along with ganaxolone is selected from the group consisting of benzodiazepines, phenytoin, fosphenytoin, valproic acid, phenobarbital, and/or levetiracetam.

In certain embodiments, the additional antiepileptic drug is a benzodiazepine (e.g., diazepam, lorazepam, etc.).

F. Definitions

All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present disclosure. When a range of values is expressed, it includes embodiments using any particular value within the range. Further, reference to values stated in ranges includes each and every value within that range. All ranges are inclusive of their endpoints and combinable.

The terms "a" and "an" do not denote a limitation of quantity, but rather denote the presence of at least one of the referenced item.

The term "about" is used synonymously with the term "approximately." The use of the term "about" with respect to doses and amounts of ganaxolone refers to values slightly outside the cited values, i.e., plus or minus 0.1% to 20%. The use of the term "about" with respect to time periods of administration means, for the purposes of the present invention, to comprise 2 hours before and 2 hours after that time period. For example, a time period of "about 6 hours" encompasses a time period of 4 hours and a time period of 8 hours. The term "about" with respect to a recited pharmacokinetic parameter value (e.g., a plasma concentration) or a range of pharmacokinetic parameters values (e.g., a range of plasma concentrations values) encompass pharmacokinetic parameters and ranges within 80% to 120% of the recited value or range.

An "active agent" is any compound, element, or mixture that when administered to a subject alone or in combination with another agent confers, directly or indirectly, a physiological effect on the patient. When the active agent is a compound, salts, solvates (including hydrates) of the free compound or salt, crystalline and non-crystalline forms, as well as various polymorphs of the compound are included. Compounds may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers in pure form and mixtures thereof are encompassed. In addition, compounds with carbon-carbon double bonds may occur in Z- and E-forms, with all isomeric forms of the compounds being included in the present invention. In these situations, the single enantiomers, i.e. optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

As used herein, the term, "antiepileptic" is a synonym of the term "antiseizure" and means a medication that is used to control seizures and/or epilepsy. The term "antiepileptic" encompasses anticonvulsant medications (i.e., medications that that prevent, stop, or lessens convulsions) and medications that prevent epileptic seizures.

As used herein, the term "Acute Repetitive Seizures" (ARS) refers to a condition manifested by multiple seizures occurring over a relatively brief period of time—generally 24 hours—in patients with epilepsy. ARS could be convulsive or non-convulsive. ARS could progress in SE, but typically there is a recovery period (break) between the seizures and/or convulsions.

The abbreviation "EEG" means electroencephalography.

The terms "serum" and "plasma" as disclosed herein may be used interchangeably.

The term "intravenous bolus" is a relatively large dose of medication (e.g., ganaxolone) administered in a short period, for example within 1 to 60 minutes (e.g., 3 or 5 minutes).

The term "Cmax" refers to the concentration of ganaxolone in the plasma at the point of maximum concentration.

The abbreviation "eIND" means emergency treatment Investigational New Drug Application.

The abbreviation "GNX" means ganaxolone.

"Ganaxolone" means 3α-hydroxy-3β-methyl-5α-pregnan-20-one.

"Infusion" administration is a non-oral administration, typically intravenous, though other non-oral routes such as epidural administration are included in some embodiments. Infusion administration occurs over a longer period than a bolus administration, for example for a time period greater than 1 hour (e.g., from about 1 hour to about 120 hours).

The term "subject" as used herein refers to a human in need of medical treatment for status epilepticus.

"Pharmaceutical compositions" are compositions comprising at least one active agent, such as a compound or salt, solvate, or hydrate of ganaxolone, and at least one other substance, such as a carrier. Pharmaceutical compositions optionally contain one or more additional active agents. When specified, pharmaceutical compositions meet the U.S. FDA's GMP (good manufacturing practice) standards for human or non-human drugs. "Pharmaceutical combinations" are combinations of at least two active agents which may be combined in a single dosage form or provided together in separate dosage forms with instructions that the active agents are to be used together to treat a disorder, such as status epilepticus.

The term "status epilepticus" (SE) is defined as a prolonged self-sustaining seizure or recurrent seizures without recovery of consciousness between seizures (Lowenstein and Alldredge, 1998). The International League Against Epilepsy further defined SE as a condition resulting either from the failure of mechanisms responsible for seizure termination or from the initiation of mechanisms, which lead to abnormally, prolonged seizures (5 minutes for tonic-clonic SE and 10 minutes for focal SE with impaired consciousness) and which can have long-term consequences (after 30 minutes for tonic-clonic SE and after 60 minutes for focal SE with impaired consciousness), including neuronal death and/or injury, and alteration of neuronal networks, depending on the type and duration of seizures. SE encompasses a generalized convulsive status epilepticus (GCSE), non-convulsive status epilepticus (NCSE), early status epilepticus, established status eplilepticus (ESE), refractory status epilepticus (RSE), and super-refractory status epilepticus (SRSE).

GCSE is defined as status epilepticus that is characterized by convulsions that are associated with tonic-clonic movements of the extremities and mental status impairment, and may result in focal neurologic deficits lasting hours to days following an episode (Brophy et al, 2012). GCSE is associated with many complications, including cardiac arrhythmias, rhabdomyolysis, pulmonary edema, electrolyte and glucose imbalance, and temperature disturbances.

NCSE is defined as status epilepticus in which seizure activity is seen on EEG without convulsive symptoms; however, acutely ill subjects may present with impaired mental status during an NCSE episode (Brophy et al, 2012).

RSE is defined as status epilepticus that failed to abort after a first-line (i.e., a benzodiazepine) and a second-line anti-seizure medication have been given. Duration is not part of the definition for RSE, which is based solely on the medications given and persistence of seizures (Falco-Walter et al, 2016).

SRSE is defined as SE that continues 24 hours or more after the onset of anesthesia, including those cases in which the SE recurs on the reduction or withdrawal of anesthesia' (Shorvon and Ferlisi, 2011).

The term "seizure" or "an epileptic seizure" means a transient occurrence of signs and/or symptoms related to abnormal, excessive or synchronous neuronal activity in the brain. Seizures are detected in the brain by measuring EEG activity. There can be seizures (in the brain) that will not be manifested as convulsions and can only be detected by EEG activity. The term "seizure activity" encompasses convulsions and EEG seizures.

A "taper period" is a period during which the continuous intravenous infusion of ganaxolone is gradually lowered prior to the discontinuation of the intravenous infusion.

The term "therapeutically effective amount" as used herein refers to the amount of ganaxolone that is sufficient to stop or reduce severity of status epilepticus or one or more of its symptom(s). For example, an amount for sufficient seizure suppression. The term "therapeutically effective amount" includes, for example, a prophylactically effective amount. The effective amount of ganaxolone will be selected by those skilled in the art depending on the particular patient and the disease. It is understood that a therapeutically effective amount can vary from subject to subject, due to variation in metabolism of ganaxolone, age, weight, general condition of the subject, the condition being treated, the severity of the condition being treated, and the judgment of the prescribing physician.

As used herein, the terms "treat" or "treatment" refer to any to any improvement or any consequence of status epilepticus, such as reduced or eliminated seizure activity and/or reduced or eliminated convulsions and/or completely suppresses status epilepticus (i.e., suppress EEG seizure activity and convulsions). As is readily appreciated in the art, full eradication of SE is preferred but albeit not a requirement for a treatment act. The treatment can be to cure, heal, alleviate, relieve, alter, remedy, ameliorate, palliate, improve or affect the disorder, the symptoms of SE or the predisposition toward SE. For example, treating may achieve seizure suppression.

5. EQUIVALENTS

It will be readily apparent to those skilled in the art that other suitable modifications and adaptions of the methods of the invention described herein are obvious and may be made using suitable equivalents without departing from the scope of the disclosure or the embodiments. Having now described certain compounds and methods in detail, the same will be more clearly understood by reference to the following examples, which are introduced for illustration only and not intended to be limiting.

6. EXAMPLES

The present invention is further described by the following examples, which are not intended to be limiting in any way.

Example 1: Preliminary Clinical Evidence of Intravenous Ganaxolone Pharmacokinetics and Pharmacodynamics A Phase I clinical trial evaluating IV ganaxolone formulation was performed. The clinical trial was designed to investigate the safety, pharmacokinetics, and pharmacodynamics of an intravenous bolus of ganaxolone and continuous intravenous infusion of ganaxolone in 30 healthy subjects. Subjects were administered either an intravenous bolus of ganaxolone in an amount of 10-20 mg for a period of 2 minutes to 1 hour, or an intravenous bolus of ganaxolone in an amount of 6 mg for a period of 5 minutes with a continuous intravenous infusion in an amount of 20 mg/hr for a period of 4 hours.

Pharmacokinetic analysis showed that all 30 healthy subjects treated with active ganaxolone had quantifiable ganaxolone levels in plasma and ganaxolone concentrations in plasma were generally proportional to the administered dose. Plasma concentrations that were achieved in this study were in the range of those associated with a potential anticonvulsant effect, based on historic data from subjects given oral ganaxolone. Analysis of pharmacodynamic data showed that the bispectral index (BIS) score correlated with estimated ganaxolone plasma concentrations at the time of BIS measurement. As expected, higher plasma concentration was associated with lower BIS scores (FIG. 1). There was little or no delay between the appearance of drug in plasma and a change in the BIS score.

Example 2: Preliminary Clinical Evidence of Efficacy in Subject with Status Epilepticus Example 2 is an ongoing, double-blind, randomized, placebo-controlled Phase 2 study designed to evaluate the safety, tolerability, and efficacy of adjunctive IV GNX in subjects with SE who have failed initial treatment with benzodiazepines and at least one AED. The study consists of a small open-label group to optimize the infusion parameters and provide a preliminary assessment of safety, efficacy, and tolerability of GNX administration, followed by a double-blind group who will be randomized to receive GNX or placebo in a 1:1 ratio. In both the open-label and double-blind groups, the study drug treatment is adjunctive therapy to standard of care, and subjects will receive a study drug bolus dose with a concurrent continuous infusion treatment with the goal of administering a therapeutic dose as quickly as possible to stop the seizures and prevent permanent neurological damage. Specifically, study drug will be added to the standard of care at the time that the first 2nd-line IV AED has failed and the second 2nd-line IV AED is medically indicated during the treatment of SE. Study drug must be administered with the second-line IV AED as close to the dose initiation of the second 2nd-line IV AED as possible, but before the initiation of the third-line IV anesthetic for burst suppression.

Ganaxolone for this study is a proprietary IV formulation solubilized by Captisol® (betadex sulfobutyl ether sodium). The maximum level of Captisol® will not exceed 50 g/per day. Ganaxolone for IV administration will be provided to the site as individual glass vials containing 3 mg/mL of ganaxolone for the open-label group and 5 mg/mL of ganaxolone for the double-blind group. Placebo for double-blind group IV administration will be provided to the site as blinded matching vials containing 0.9% sodium chloride solution.

The primary objective of the study is to establish that IV GNX given concomitantly with second-line IV AED therapy is safe and effective in stopping SE that has already failed at least one second-line IV AED therapy and prevents escalation of treatment requiring an IV anesthetic drug (a third-line treatment) for seizure suppression. Secondary objectives include assessment of mortality, seizure cessation in subjects with SE, and evaluation of pharmacokinetics of IV GNX in subjects with SE. Approximately 262 subjects will be enrolled across the open-label and the double-blind groups.

Total adjunctive GNX therapy infusion treatment is planned to be 3 or 5 days (including an 18-hour taper). All subjects will have a 3-minute bolus dose with a continuous infusion at the rate from about 10 mg/hour to about 85 mg/hour or from about 18 mg/hr to 80 mg/hr, and an 18-hour taper. Once study drug administration is started it will be delivered for a full 2 or 4 days (48 or 96 hours) prior to tapering. At the end of second day administration, the decision to administer the study drug for an additional 2 days (i.e., for a total of 4 days) will be made. If in the investigator's medical judgment the subject will continue benefitting from study drug administration, ganaxolone will be administered to the additional 2 days.

Ganaxolone dose will be tapered prior to the discontinuation. To taper ganaxolone after 2 or 4 days of treatment, the continuous infusion will be reduced by 25% every 6 hours; 75%, 50%, 25% over 18 hours and then discontinued. If the infusion rate becomes too low during these 18-hours to sustain the infusion line it can be discontinued at that point. It is contemplated that, if a subject takes study drug for less than 2 hours and/or requires an IV anesthetic drug (a 3rd line treatment) for seizure suppression, they should be discontinued from the study drug without the study drug taper.

The following dosing schedule is planned.

Subjects Weighing at Least 40 kg:

A 25-mg bolus dose (over ~3 minutes) will be administered with a continuous infusion of 80 mg/hour for 2 hours followed by a continuous infusion rate of 40 mg/hour for 6 hours, and then 18 mg/hour for the remaining 16 hours of Day 1. At the end of the first 24 hours of continuous infusion (Day 1), the infusion rate will be increased to 29 mg/hour for the remaining treatment, Day 2 (24-48 hours) or Day 2 through 4 (24-96 hours).

TABLE 2

Dosing for Subjects ≥40 kg (on an mg/hour basis)

| Days | Start Time from Dose Initiation | Dose Level of Study Drug IV (infusion rate) | Duration |
|---|---|---|---|
| Day 1 | 0 hours: bolus dose via syringe or infusion pump | 25 mg | 3 minutes |
| Day 1 | 0 hours through 2 hours post-dose: continuous infusion, started with bolus | 80 mg/hour | 2 hours |
| Day 1 | 2 hours post-dose through 8 hours post-dose | 40 mg/hour | 6 hours |
| Day 1 | 8 hours post-dose through 24 hours post-dose | 18 mg/hour | 16 hours |
| Day 2 or Day 2 through Day 4 | 24 hours post-dose through 48 hours post dose (Day 2) or 24 hours post-dose though 96 hours post-dose (Day 2-4) | 29 mg/hour | 24-72 hours (Day 2 or Day 4) |
| Taper for subjects discontinuing study drug | | | |
| Day 3 or Day 5 | 48 or 96 hours post-dose: 18-hour taper | Reduce infusion rate by 25% | 6 hours |
|  |  | Reduce infusion rate by 25% | 6 hours |
|  |  | Reduce infusion rate by 25% | 6 hours |

Subjects Weighing <40 kg Will be Dosed on a Per-Kilogram Basis:

A 0.375-mg/kg bolus dose (over ~3 minutes) will be administered with a continuous infusion of 1.2 mg/kg/hour for 2 hours followed by a continuous infusion rate of 0.6 mg/kg/hour for 6 hours, and 0.27 mg/kg/hour for the remaining 16 hours of Day 1. At the end of the first 24 hours of continuous infusion (Day 1), the infusion rate will be increased to 0.435 mg/kg/hour for the remaining treatment period, Day 2 (24-48 hours) or Day 2 through 4 (24-96 hours).

TABLE 3

Dosing for Subjects <40 kg (on an mg/kg/hour basis)

| Days | Start Time from Dose Initiation | Dose Level of Study Drug | Duration |
|---|---|---|---|
| Day 1 | 0 hours: bolus dose via syringe or infusion pump | 0.375 mg/kg | 3 minutes |
| Day 1 | 0 hours through 2 hours post-dose: continuous infusion, started with bolus | 1.2 mg/kg/hour | 2 hours |
| Day 1 | 2 hours post-dose through 8 hours post-dose | 0.6 mg/kg/hour | 6 hours |
| Day 1 | 8 hours post-dose through 24 hours post-dose | 0.27 mg/kg/hour | 16 hours |
| Day 2 or Day 2 through Day 4 | 24 hours post-dose through 48 hours post dose (Day 2) or 24 hours post-dose though 96 hours post-dose (Days 2-4) | 0.435 mg/kg/hour | 24-72 hours (Day 2 or Days 2-4) |
| Taper for subjects discontinuing study drug | | | |
| Day 3 or Day 5 | 48 or 96 hours post-dose: 18-hour taper | Reduce infusion rate by 25% | 6 hours |
|  |  | Reduce infusion rate by 25% | 6 hours |
|  |  | Reduce infusion rate by 25% | 6 hours |

These infusion dosing parameters are expected to result in daily doses of ganaxolone of about ≤714 mg/day and Captisol of about ≤50 grams/day. Based on PK modeling, it is predicted that maximum concentrations of ganaxolone should remain within 1,000 ng/mL during infusion, but some variability is expected due to, for example, differences in subjects' weight.

As of 22 Mar. 2019, 5 subjects were enrolled into the Study 1042-SE-2001 open-label group under the original protocol that limits daily Captisol exposure at 35 g/day. In all 5 cases, the initial 3-minute bolus dose of 30 mg GNX with concurrent continuous infusion at 85 mg/hr for 2 hours followed by 40 mg/hr for 2 hours of GNX infusion resulted in the immediate cessation of seizures as evidenced by EEG activity in subjects with SE that was otherwise resistant to several second line IV AEDs considered standard-of-care. The initial EEG pattern post-infusion initiation was described by study physicians as a "light" burst suppression that was maintained for several hours in all subjects.

Figure 2:
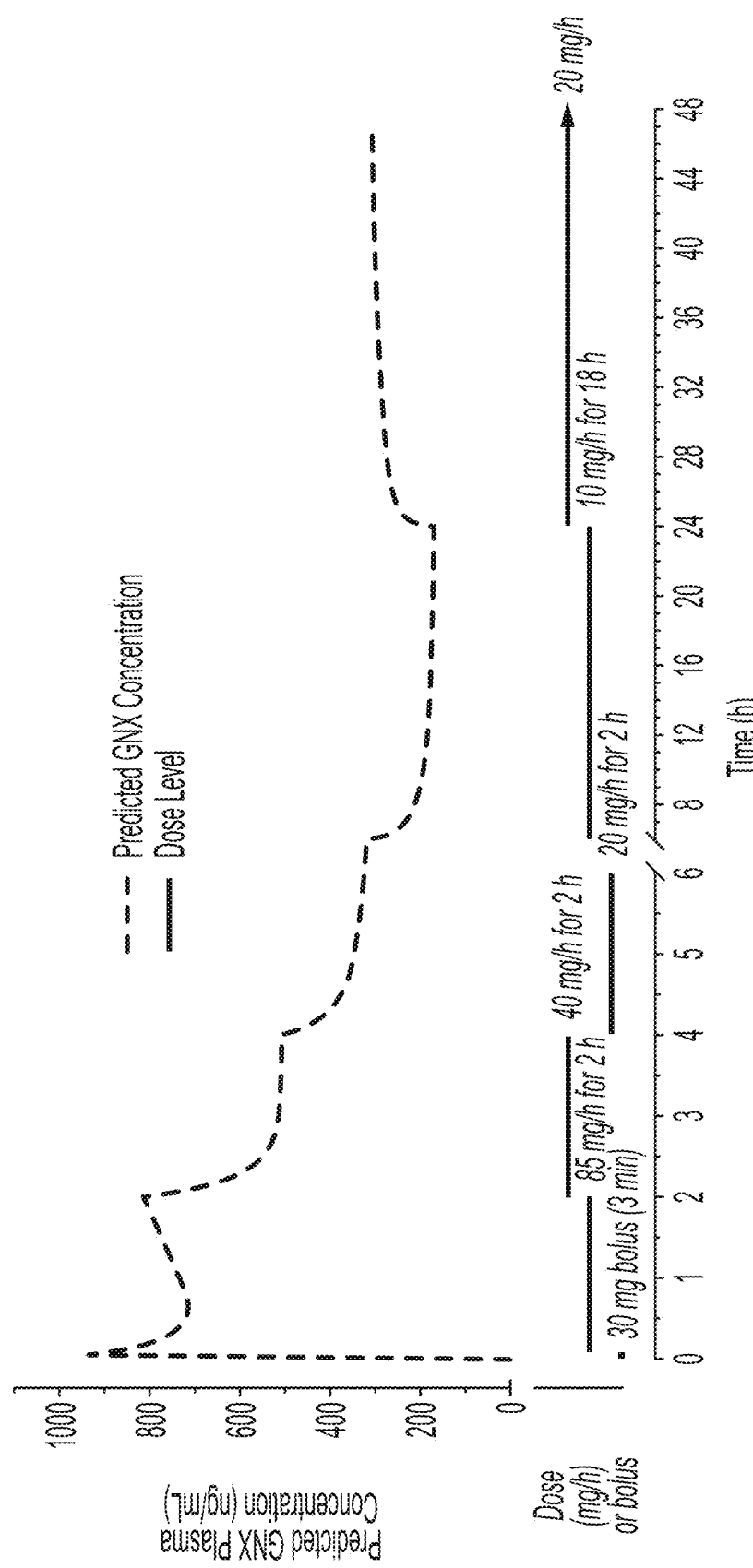
FIG. 2 is a graph showing predicted ganaxolone plasma concentration against time.

Although some subjects required intubation for airway protection, no subjects had to be intubated as a direct result of GNX therapy. In addition, no GNX-related cardiovascular events that required pharmacological intervention were observed. It was observed that when GNX exposure was lowered (20 mg/hr for 2 hours and ending with 10 mg/hr for the remaining 18 hours on Day 1) in order not to exceed this limit, seizure control could not be maintained and seizure activity (but not SE) re-occurred as evidenced by EEG changes. Pharmacokinetic modeling data (FIG. 2) from these 5 subjects suggested that exposure levels of GNX at approximately 1000 ng/mL were associated with rapid and complete SE suppression, and lower GNX exposures at <500 ng/mL were associated with seizure relapse. Seizure activity relapsed when plasma concentrations of GNX decreased <500 ng/mL in 4 out of 5 subjects.

Case reports of the 5 subjects are presented below.

1. Subject 004-101

Subject 004-101 was a 75-year-old female who presented with a subdural hematoma due to a fall (Day 1). Levetiracetam was started. Upon physician exam, the subject was noted to be lying in the bed unresponsive to both verbal and noxious stimuli. Pupils were equal, round, and reactive to light, no corneal, no gag, and vestibulo-occular reflex was intact. Blood pressure and saturation were stable. Due to the mental status change, the decision was made to intubate the subject for airway protection. On Day 3, EEG showed partial seizures and additional infusions of levetiracetam were given, followed by multiple infusions of lacosamide. During the study enrollment discussion, the family reported that the subject was slow to come out of anesthesia in the past.

Figure 3:
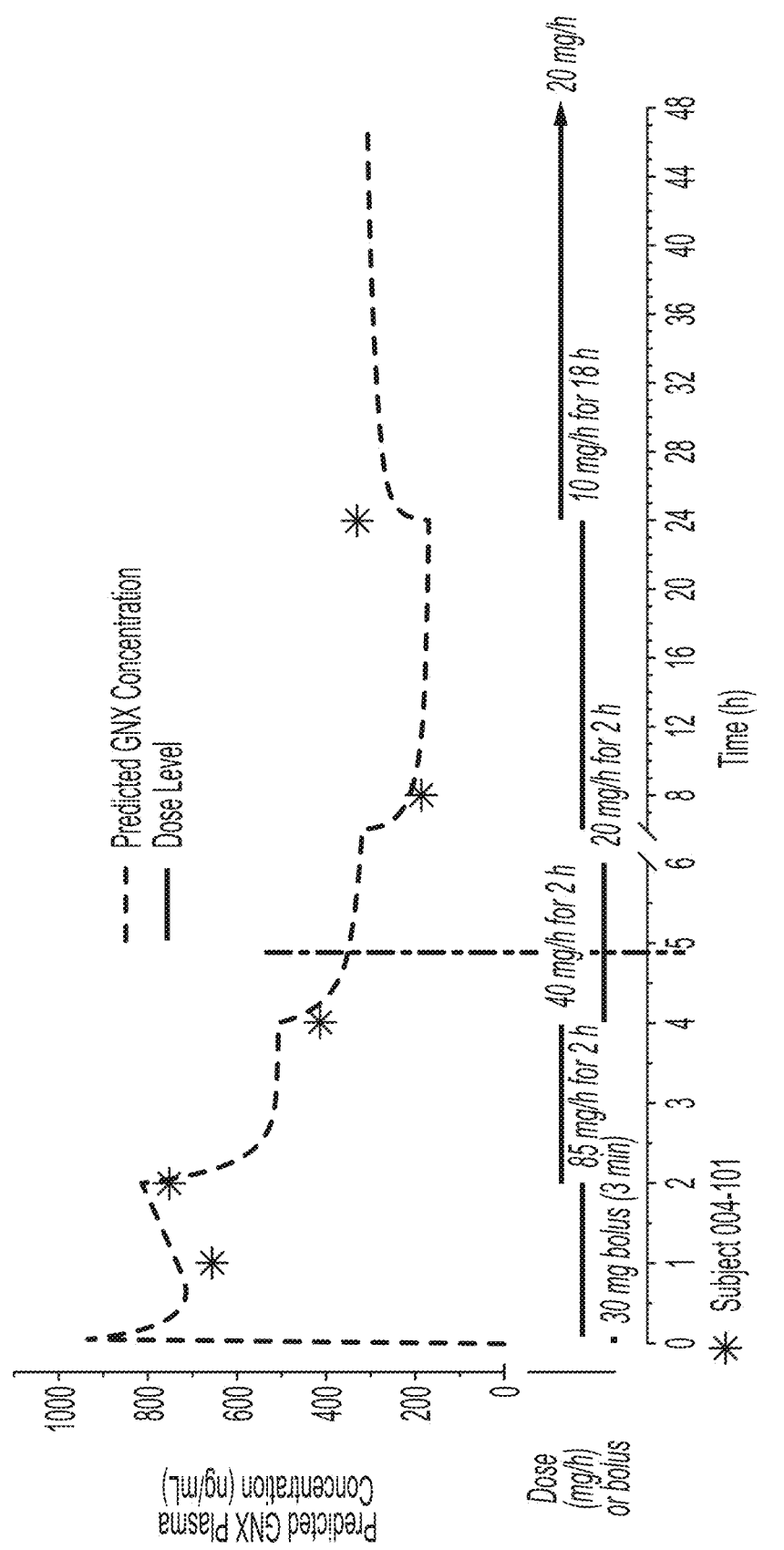
FIG. 3 is a graph showing predicted and actual ganaxolone plasma concentration against time for subject 004-101. The vertical line marks the time of seizure relapse.
Figure 4:
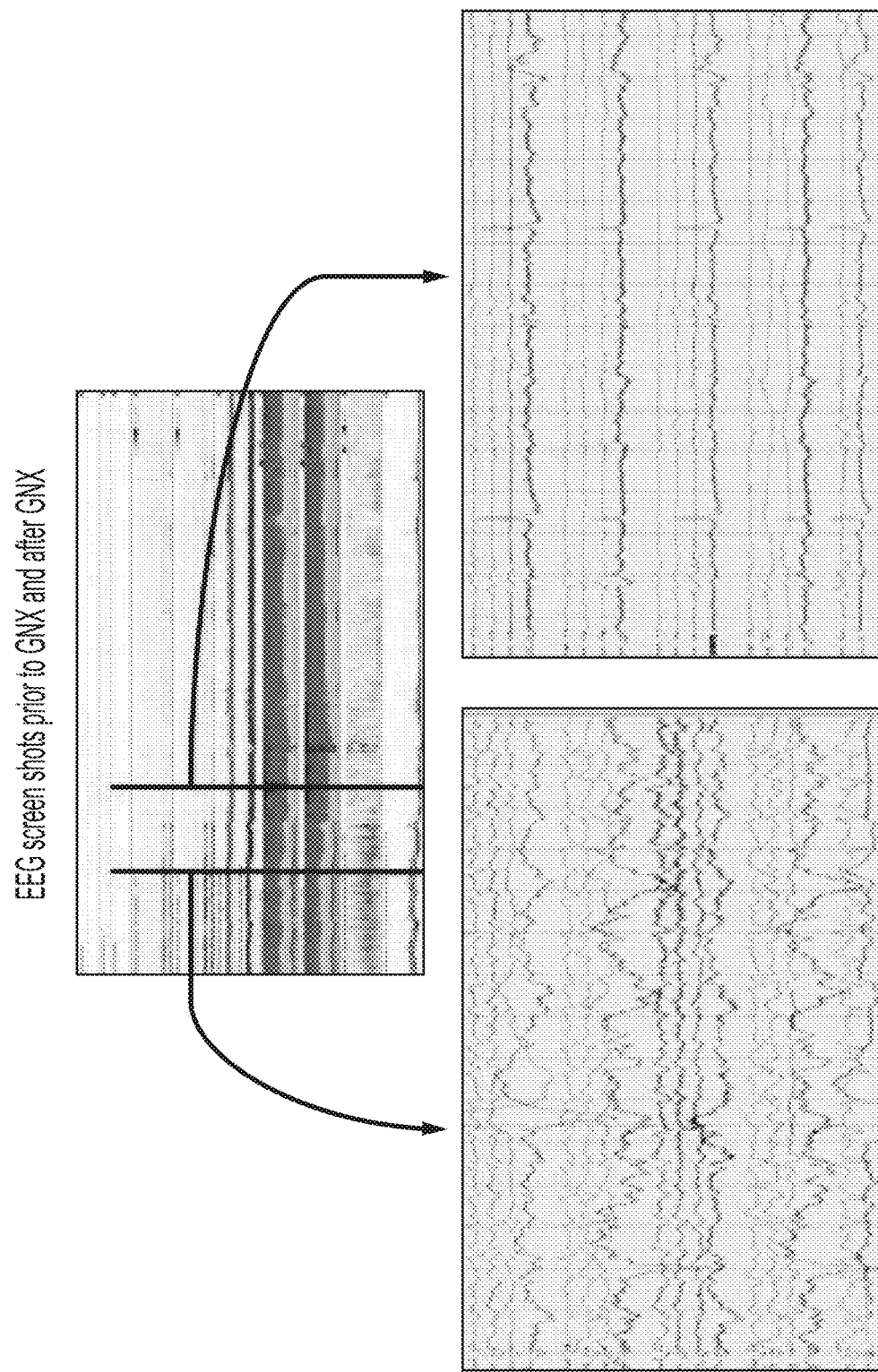
FIG. 4 is a snapshot of electroencephalography for subject 004-101.

On Day 3, IV GNX was administered starting with a 30 mg bolus over 3 minutes and a continuous infusion of 85 mg/hr for 2 hours. Almost immediately the EEG showed seizure suppression, with the EEG pattern described as by the Principal Investigator as, "putting the subject in weak burst suppression." During the second hour of treatment the study drug administration was interrupted for 14 minutes while the subject was intubated for airway protection. The intubation was not considered related to the study drug; the decision to intubate was made before starting GNX infusion. The continuous infusion was restarted without incident. Dosing continued per protocol with infusion rate reductions to 40 mg/hr at 2 hours post-dose, 20 mg/hr at 4 hours post-dose, and 10 mg/hr at 6 hours post dose. Seizure relapse occurred at approximately 5 hours post infusion start, at which time the subject was receiving GNX at a 20 mg/hr infusion rate. GNX was discontinued on Day 2. The subject's GNX plasma concentration was <500 ng/mL at the time of seizure relapse (FIG. 3). A snapshot of the subject's EEG patterns prior to and after initiation of GNX is provided in FIG. 4.

2. Subject 004-102

Figure 5:
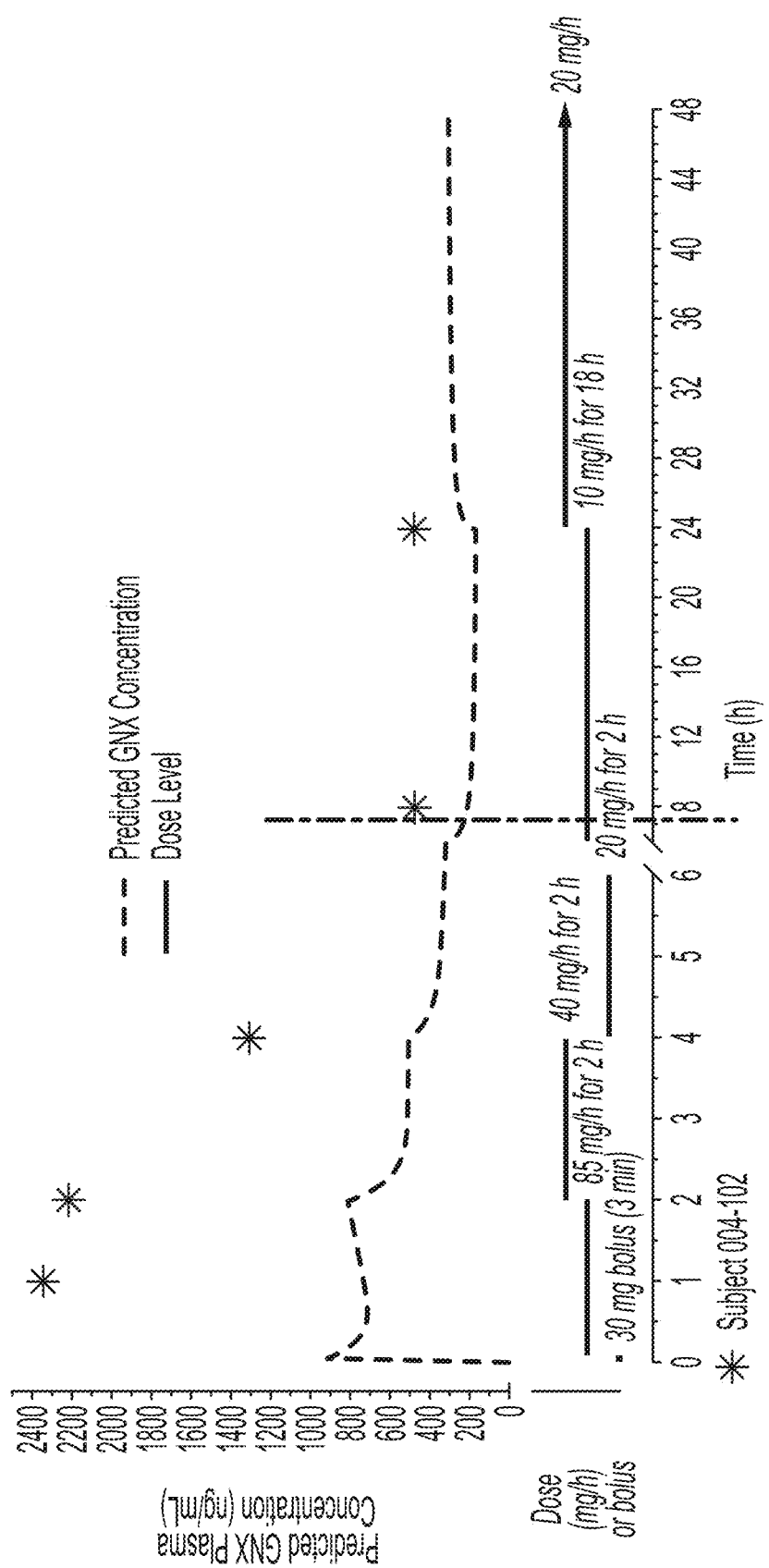
FIG. 5 is a graph showing predicted and actual ganaxolone plasma concentration against time for subject 004-102. The vertical line marks the beginning of the return of abnormal EEG activity that later required additional intervention.
Figure 6:
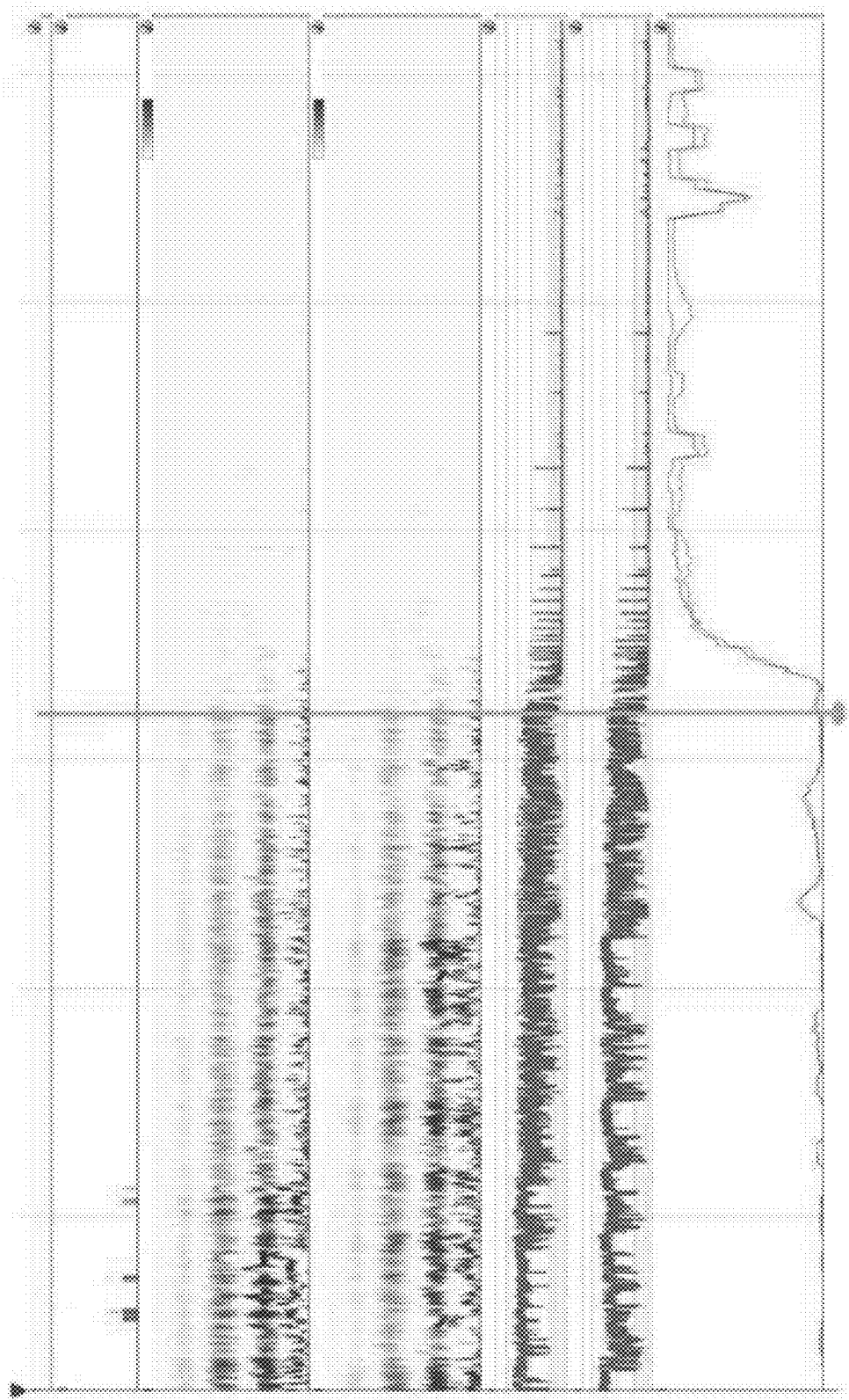
FIG. 6 is a snapshot electroencephalography for subject 004-102.

Subject 004-102 was a 43-year-old female with a history of seizures who presented in NCSE (Day 1). Prior AED medications included lamotrigine. The subject was intubated and given a single dose of fosphenytoin followed by levetiracetam. On the same day, IV GNX 30 mg bolus was given over 3 minutes and the continuous infusion (85 mg/hr) was initiated. There was no seizure activity noted on EEG at 60 minutes and 2 hours post-dose initiation. As per the protocol, GNX was decreased to 40 mg/hr, 20 mg/hr, and 10 mg/hr sequentially. The 10 mg/hr was continued for the remaining 18 hours of Day 1. The subject continued to be seizure free; however, a concerning EEG pattern returned between 5 to 6 hours post-dose initiation, at which time the subject was receiving GNX at a 20 mg/hr infusion rate. The subject's GNX plasma concentration at the time of seizure relapse is shown in FIG. 5. A return of an EEG pattern occurred around the same timeframe and it evolved over the next 48 hours and required additional intervention approximately 42.5 hours post-dose initiation while the subject was receiving GNX at a 20 mg/hr infusion rate. GNX was discontinued on Day 2. A snapshot of the subject's qualitative EEG patterns prior to and after initiation of GNX is provided in FIG. 6.

3. Subject 006-101

Figure 7:
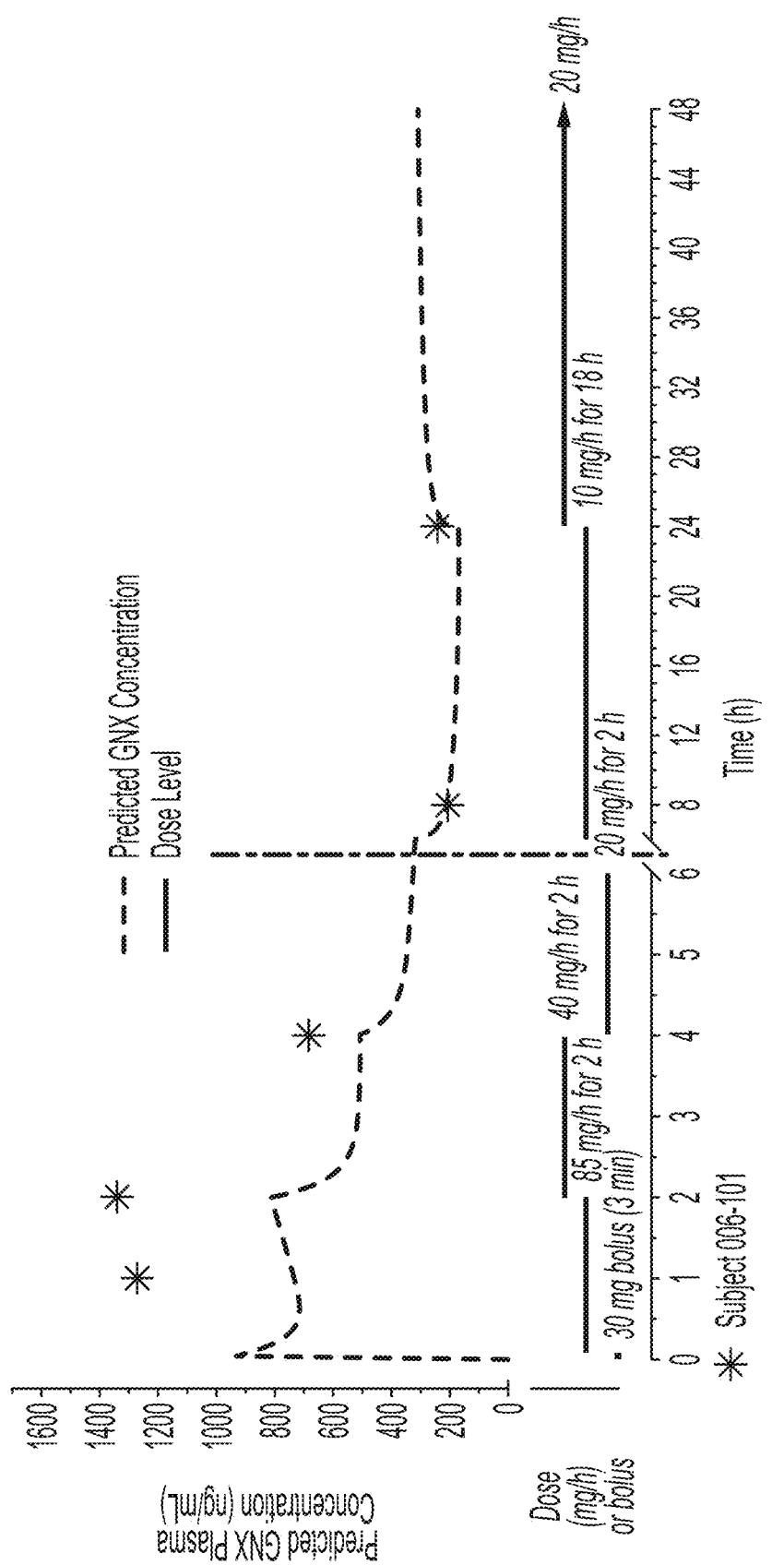
FIG. 7 is a graph showing predicted and actual ganaxolone plasma concentration against time for subject 006-101. The vertical line marks the time of seizure relapse.
Figure 8:
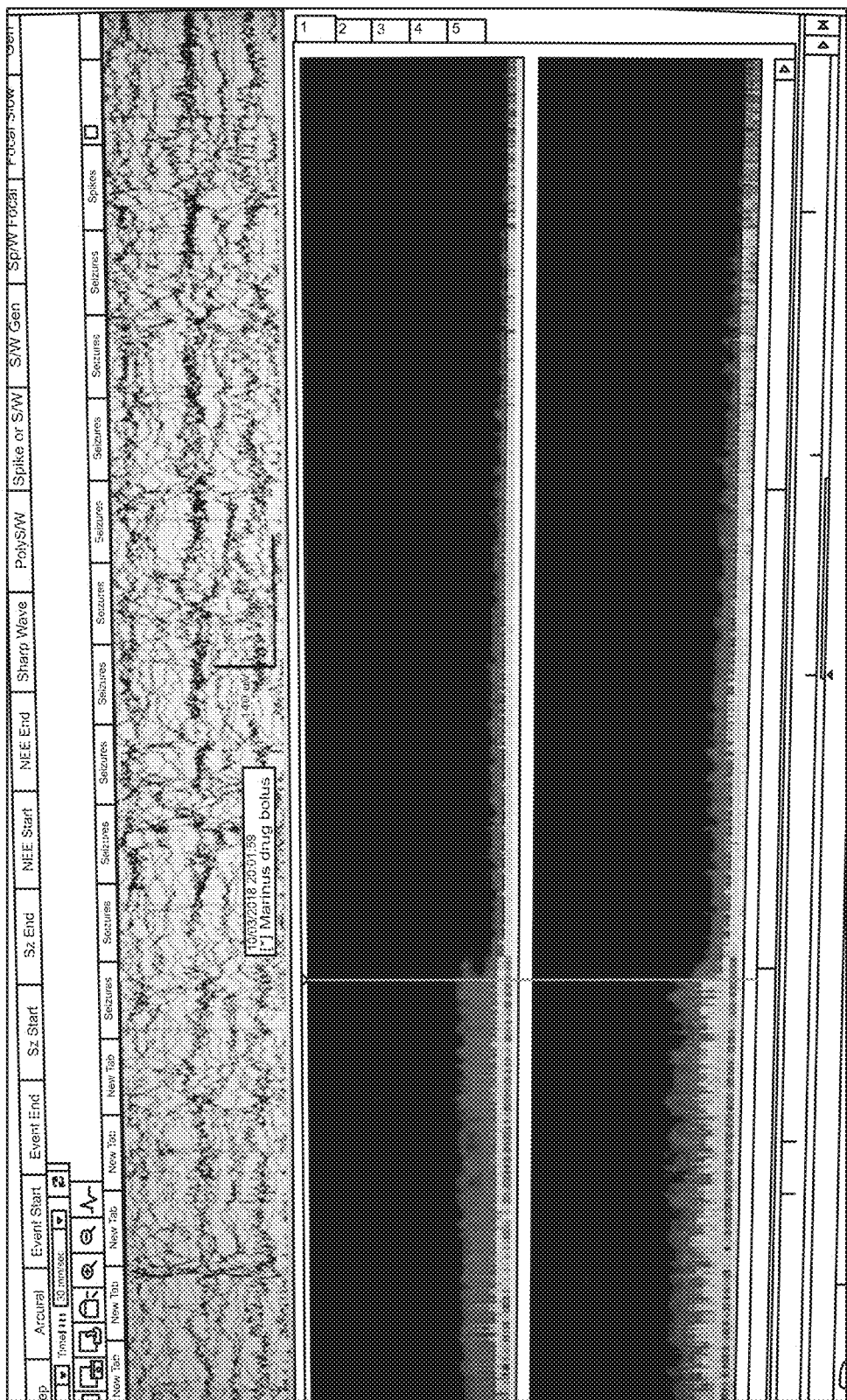
FIG. 8 is a photograph of electroencephalography for subject 106-102. The vertical line marks the time of ganaxolone treatment initiation.

Subject 006-101 was a 59-year-old female who presented in NCSE, etiology unknown (Day 1). Subject was unresponsive to verbal and physical stimuli. A single dose of lacosamide was given and subject was intubated for airway protection. EEG showed epileptiform discharges associated with obtundation and limb switches, and was subject was given lorazepam dose with no improvement. On the same day, IV GNX 30 mg bolus was given and the continuous infusion (85 mg/hr) was initiated. Per site report, the SE aborted within 1 minute of the bolus administration. There was no seizure activity noted on EEG at 60 minutes and 2 hours post-dose initiation. Per the protocol, GNX was sequentially decreased to 40 mg/hr, 20 mg/hr, and 10 mg/hr. Seizure relapse occurred at approximately 6 hours post infusion start, at which time the subject was receiving GNX at a 20 mg/hr infusion rate. GNX taper was initiated on Day 4. The subject's GNX plasma concentration was <500 ng/mL at the time of seizure relapse (FIG. 7). A snapshot of the subject's EEG patterns prior to and after initiation of GNX is provided in FIG. 8.

The SE relapse occurred while the subject's infusion rate was 10 mg/hr. The two adjacent PK sample results were within the low predicted values for the infusion rate. It was confirmed that PK samples were collected from the infusion site. It was confirmed that the correct analysis procedures where performed by the bioanalytical laboratory.

4. Subject 006-102

Figure 9:
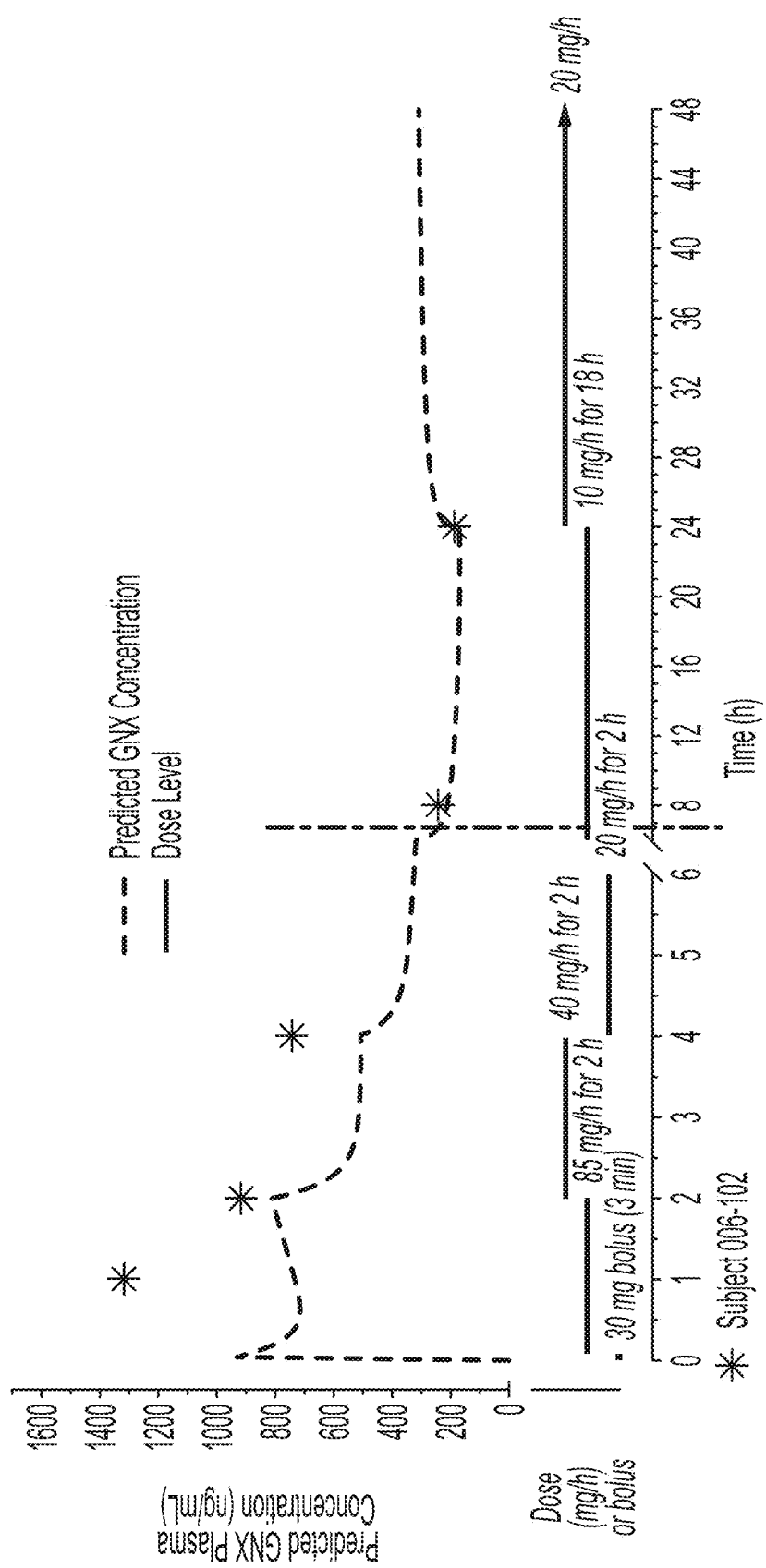
FIG. 9 is a graph showing predicted and actual ganaxolone plasma concentration against time for subject 006-102. The vertical line marks the time of seizure relapse.

Subject 006-102 was an 88-year-old female with a history of seizures and dementia who was transferred from a nursing home after having been found by her daughter with altered mental status and inability to verbalize her complaints (Day 1). The family confirmed that the subject had fallen and possibly hit her head the previous week. Subdural hematoma (1.4 cm) was identified on computed tomography (CT) scan. Subject was intubated, placed on propofol, and transferred from the remote hospital to the study site where she was prepared for evacuation of the subdural hematoma. Propofol was stopped. During physical examination, the subject's eyes opened spontaneously, the pupils were equal round, and reactive to the light. She followed simple commands and moved all the extremities spontaneously. The subject was administered single doses of levetiracetam on Day 1 and Day 4 and twice daily dosing on Day 3. Three single doses of lorazepam were administered on Day 5 prior to GNX administration along with multiple doses of levetiracetam and a single dose of lacosamide. On Day 5, the subject had worsening neurological exam and CT of the head showed signs of stroke on the right cerebral hemisphere. On the same day, an EEG confirmed a diagnosis of NCSE at which time the subject was enrolled in the clinical study and started on IV GNX 30 mg bolus dose plus continuous infusion (85 mg/hr). Per site report, the SE aborted upon administration of the bolus GNX administration. There was no seizure activity noted on EEG at 60 minutes, 2 hours, and 4 hours post-dose initiation. Per the protocol, GNX was sequentially decreased to 40 mg/hr, 20 mg/hr, and 10 mg/hr. Seizure relapse occurred at approximately 6 hours post infusion start, at which time the subject was receiving GNX at a 20 mg/hr infusion rate. GNX taper was initiated on the fourth day of GNX therapy. The subject's GNX plasma concentration was <500 ng/mL at the time of seizure relapse (FIG. 9).

5. Subject 015-101

Figure 10:
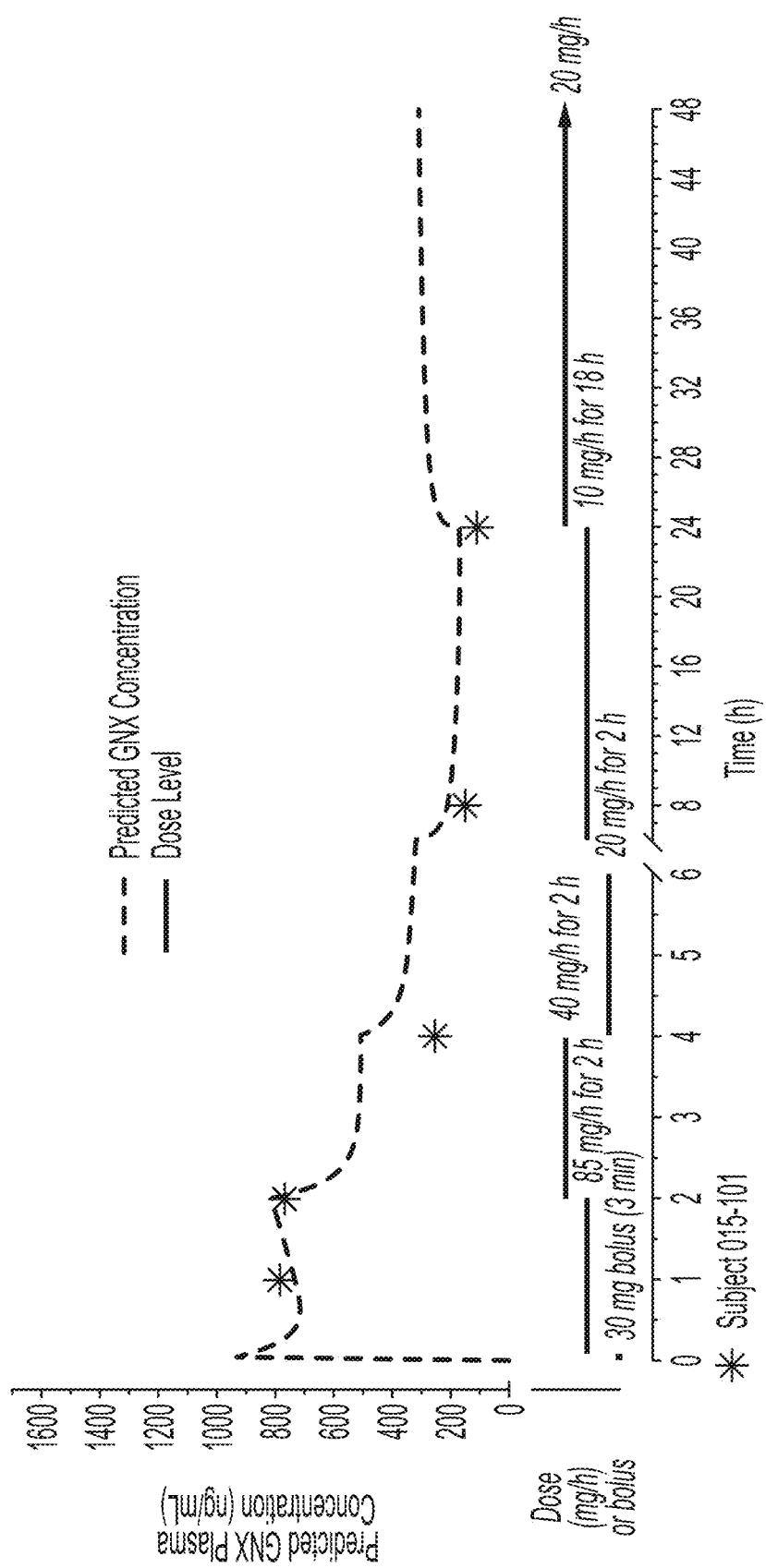
FIG. 10 is a graph showing predicted and actual ganaxolone plasma concentration against time for subject 015-101.

Subject 015-101 was a 24-year-old female who presented with focal convulsive SE due to a tumor (Day 1). Recent medical history included convulsive seizures, SE, and Glioblastoma multiform of parietal lobe. Subject was administered levetiracetam for SE and lorazepam, diazepam, dexamethasone, and multiple doses of levetiracetam for seizure control prior to study enrollment. On Day 3, the subject was enrolled in the study and started on IV GNX 30 mg bolus dose plus continuous infusion (85 mg/hr). At the start of dose initiation the subject was alert. Shortly after the bolus started the subject developed significant somnolence. She was arousable to voice but required continuous stimulation to stay awake or follow commands. She maintained her airway and was able to endorse that the numbness had resolved and reported that she no longer felt twitches. She had a feeling of impending doom and death. The subject had significant direction-changing nystagmus and complained of blurry vision. At the same time she developed urinary retention with urgency. The bladder scanner demonstrated at least 750 mL of urine and Foley catheter was placed. During the next 2 hours the subject remained somnolent and was becoming increasingly restless. As per the protocol, GNX was decreased to 40 mg/hr at 2 hours post dose initiation. Approximately 10 to 15 minutes after the infusion rate was decreased to 40 mg/hr, the subject's arousal improved, she became conversational, and wanted to eat. She had no seizures at this time. Vital signs remained stable. During the GNX infusion, concomitant lacosamide was increased due to increased numbness. Seizures did not return during the treatment period and the investigator tapered the study drug per the protocol after 2 days. Once the GNX taper was completed the investigator reported there were no sequelae. The subject's GNX plasma concentration over time is provided in FIG. 10.

In summary, all 5 subjects showed immediate cessation of SE with the initiation of the initial bolus plus continuous infusion dose. Based on these data, the United States Food and Drug Administration (FDA) allowed the daily limit of Captisol exposure to increase to 50 g/day (and the total daily dose of GNX to increase from 500 to 715 mg), thereby allowing for GNX exposure to be maintained at >500 ng/ml for approximately 8 hours.

Under the protocol amended with the 50 g/day Captisol limit, 1 subject was enrolled in the open-label study as of 26 Mar. 2019. The male subject presented with NCSE due to a tumor. The subject failed 3 second-line IV AEDs and qualified for the study based on the study's inclusion/exclusion criteria. Within 3 minutes after starting the IV GNX infusion, the RSE ceased and seizure protection was maintained for the remaining 48 hours of GNX treatment. The subject was successfully weaned off GNX (i.e., no seizure relapse). Based on the preliminary assessment, the only safety finding related to GNX was an increased sedation (likely due to a concomitant use of GNX with several AEDs with CNS-depressant properties as part of standard of care anti-seizure therapy). Pharmacokinetic data were unavailable at the time of this report.

In addition, GNX has been administered to 2 subjects with SRSE under separate emergency treatment INDs (eINDs).

Figure 11:
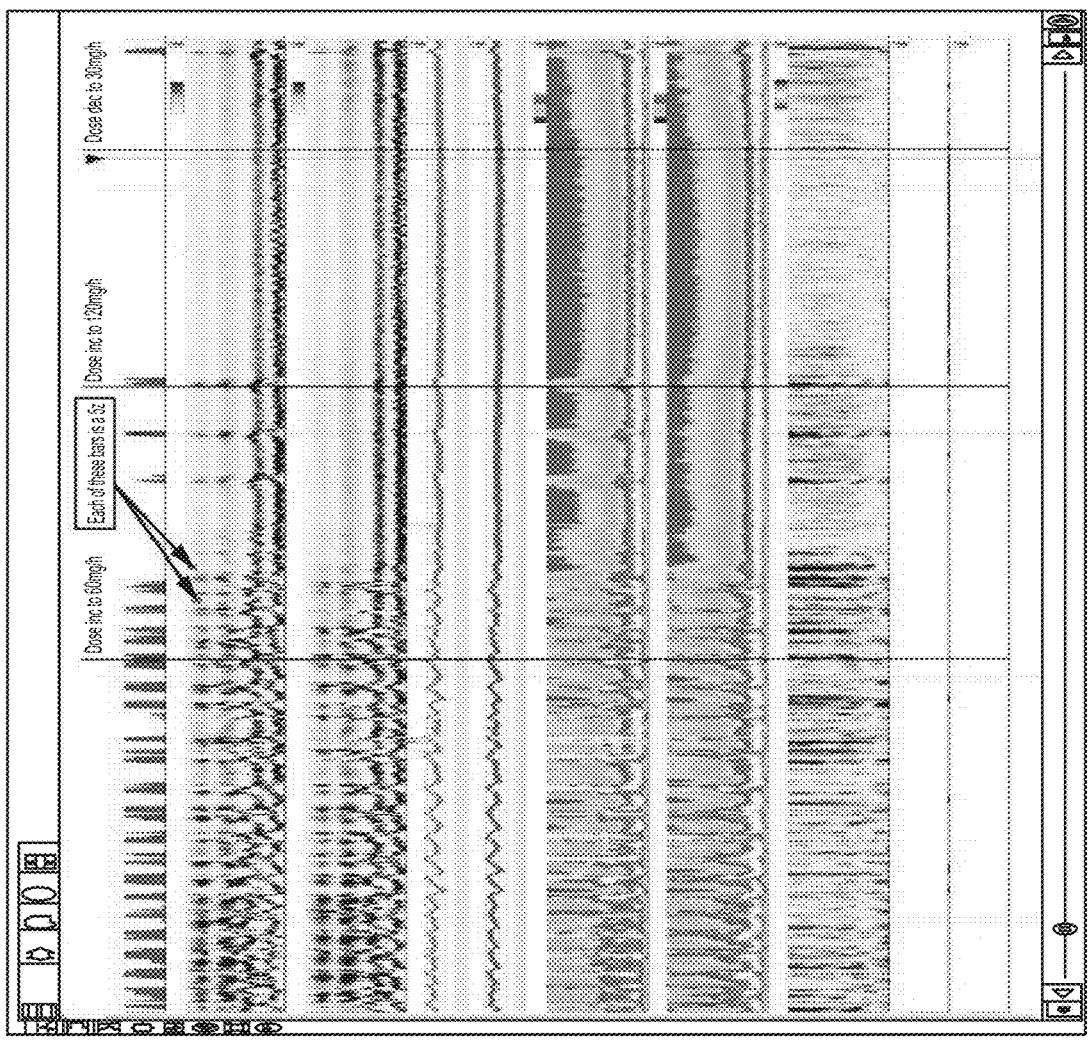
FIG. 11 is a snapshot of electroencephalography of Subject from eIND No. 131,642. Seizures appear as dark areas, as indicated by the comments on the upper margin.

Under eIND No. 131,642, IV GNX was administered to a subject with SRSE who was unable to maintain status cessation with ketamine and barbiturates. The Day 1 dosage regimen delivered 900 mg of GNX, equating to a 900 to 1200 ng/mL plasma concentration of GNX. As the subject could not be maintained in burst suppression, the clinical team was able to utilize EEG changes to gauge the response (FIG. 11). The effect of GNX started at 60 mg/hr dose and resulted in complete seizure cessation at the 120 mg/hr dose. However, due to the dosing plan agreed upon with the FDA with a daily Captisol limit of 63 g/day, the initial 120 mg/hr dose on Day 1 could not be maintained for longer than 1 hour and then had to be decreased to the 30 mg/hr dose. The first seizures re-occurred within 15 to 20 minutes of the change in GNX dose from 120 mg/hr to 30 mg/hr.

Additionally, under eIND No. 137,883, IV GNX was administered to a pediatric subject with SRSE who had previously failed treatment with levetiracetam, topiramate, clobazam, phenobarbital, rufinamide, perampanel, pentobarbital, and ketamine. At the time of the eIND, no pediatric pharmacokinetic data was available for the IV formulation of GNX. The dose regimen (GNX initiated at 75 mg/hr and rate decreased to 40 mg/hr 1 hour later) was based on plasma drug concentration levels measured in adults and designed to achieve a plasma drug concentration of approximately 1000 ng/mL within 1 hour and hold that level for 23 additional hours. At the time of GNX initiation, the subject was intubated and receiving pentobarbital at a rate of 2.25 mg/kg/hr. At the time of the GNX bolus infusion, the EEG showed a continuous suppressed background. This activity lasted for approximately 2 hours at which point the pentobarbital was decreased to 1 mg/kg/h. On examination the subject had nonreactive pupils and GNX infusion was stopped.

With these encouraging data, Marinus received permission from the U.S. FDA to increase daily Captisol limits from 35 to 50 g/day. One subject under the increased Captisol daily limit experienced rapid RSE cessation following GNX treatment despite failing 3 second-line IV AEDs and was successfully weaned off GNX without seizure relapse.

This study is ongoing and once completed will be used to design the pivotal Phase 3 study in subjects with RSE.

Example 3: Phase 2 Open-Label Dose Range Study

An open-label, dose range finding study in which IV ganaxolone was added to standard-of-care IV AEDs in SE patients who had failed initial benzodiazepines and at least one 2nd line IV AED but had not progressed to IV anesthetics was performed. The primary objective of the study was to establish that IV ganaxolone was safe and effective when added to standard of care IV AED therapy in stopping SE and preventing the escalation of treatment to IV anesthesia for seizure suppression. Secondary objectives included assessment of adverse events and evaluation of the pharmacokinetics of IV ganaxolone in patients with SE.

Eligible patients were treated with continuous adjunctive IV ganaxolone infusion. Initial dosing included a 3-minute bolus dose (25 or 30 mg) with a continuous infusion at rates ranging from 10 to 85 mg/hour for up to 96-hours, followed by an 18-hour study drug taper.

The study enrolled 17 patients divided among 3 dosing cohorts. The IV solution utilizes Captisol® as an excipient for solubilization of ganaxolone. In an agreement with the Food and Drug Administration (FDA), the Captisol exposure for patients participating in Study 1042-SE-2001 was not to exceed 50 g/day. Given the daily Captisol limit, 3 different doses of GNX IV solution were investigated; 500, 650, and 713 mg/day total GNX referred to as the low, medium, and high dose level cohorts, respectively.

The details on the infusion parameters during the firsts 24 hours for each of the dose groups are provided below:

TABLE 4

Infusion parameters for each dose cohort

| Dose Cohort | Dose |
|---|---|
| Low dose | 30 mg bolus, 85 mg/hr for 2 hours, 40 mg/hr for 2 hours, 20 mg/hr for 2 hours, and 18 mg/hr for 18 hours |
| Medium dose | 25 mg bolus, 35 mg/hr for 12 hours, 25 mg/hr for 4 hours, and 13 mg/hr for 8 hours |
| High dose | 25 mg bolus, 80 mg/hr for 2 hours, 40 mg/hr for 6 hours, and 18 mg/hr for 16 hours. |

TABLE 5

Participant enrollment in the study

| Cohort | Dose of GNX/day | Duration ≥500 ng/ml | Number of Participants Enrolled |
|---|---|---|---|
| Low | 500 mg/day | 4 hours | 5 |
| Medium | 650 mg/day | 0 hours | 4 |
| High | 713 mg/day | 8 hours | 8 |

GNX = ganaxolone

Preliminary results from this open-label, dose-finding Study 1042-SE-2001 in RSE patients showed that all patients (100%; n=17) did not require escalation of treatment to an IV anesthetic drug for SE control within the first 24-hours after initiation of GNX treatment, thereby meeting the primary endpoint. 16 patients (94%) achieved and maintained SE cessation within the first 24-hours following initiation of GNX treatment. 14 patients (82%) did not require additional IV AEDS or IV anesthetics for status relapse up to 4 weeks. A summary is provided below in Table 6.

TABLE 6

Preliminary results from open-label, dose-finding study in RSE patients

| Cohort | No escalation to IV anesthetics within 24 hrs from infusion initiation (Primary Endpoint) | Status-free through 24 hrs from infusion initiation | No escalation to additional IV AEDs or IV anesthetics for status relapse at any time through 24 hrs after GNX discontinuation | No SE Relapse at anytime during the 4-wk follow up period |
|---|---|---|---|---|
| Target (713 mg/day) (n = 8) | 100% (8 of 8) | 88% (7 of 8) | 100% (8 of 8) | 100% (6 of 6) (1ET, 1 died) |
| Medium (650 mg/day) (n = 4) | 100% (4 of 4) | 100% (4 of 4) | 75% (3 of 4) | 67% (2 of 3) (1 ET) |
| Low (500 mg/day) (n = 5) | 100% (5 of 5) | 100% (5 of 5) | 60% (3 of 5) | 50% (1 of 2) (1 died) |

Figure 14:
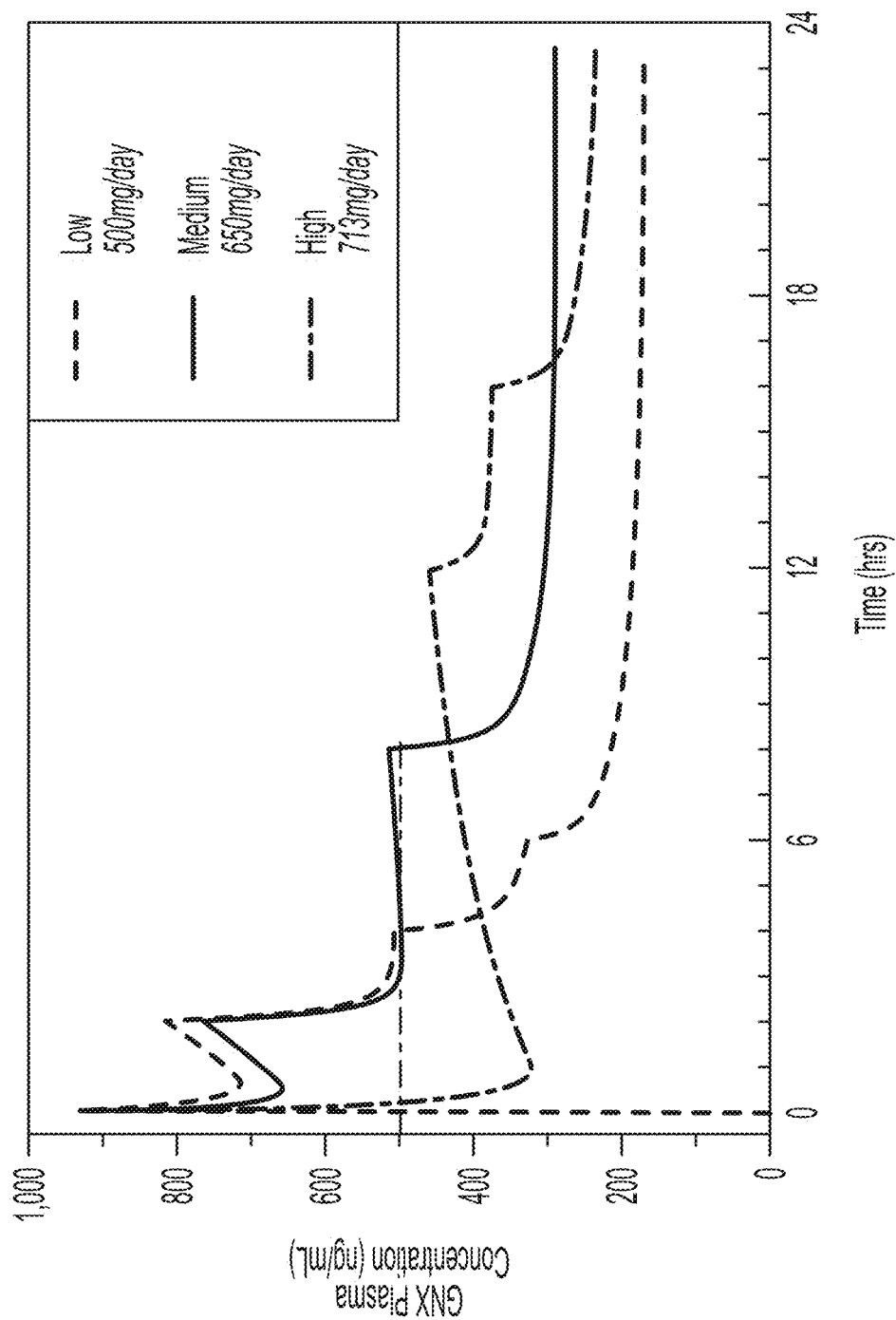
FIG. 14 is a graph depicting modeled PK curves for low, medium, and high dosing cohorts.

The major difference between the low and high dosing cohorts was the duration of predicted plasma GNX levels ≥500 ng/ml (4 vs. 8-hours, respectively). The major differences between the medium and low/high dose cohorts was the duration of initial predicted plasma levels of GNX≥700 ng/mL (minutes vs. 2-hours, respectively) and that the predicted plasma levels of GNX in the medium dose cohort never exceeded 500 ng/mL. The predicted 24-hr GNX plasma concentrations associated with each dosing cohort are shown in FIG. 14.

The number of patients enrolled into each of the three dose level cohorts are presented in table 5 below.

Figure 12:
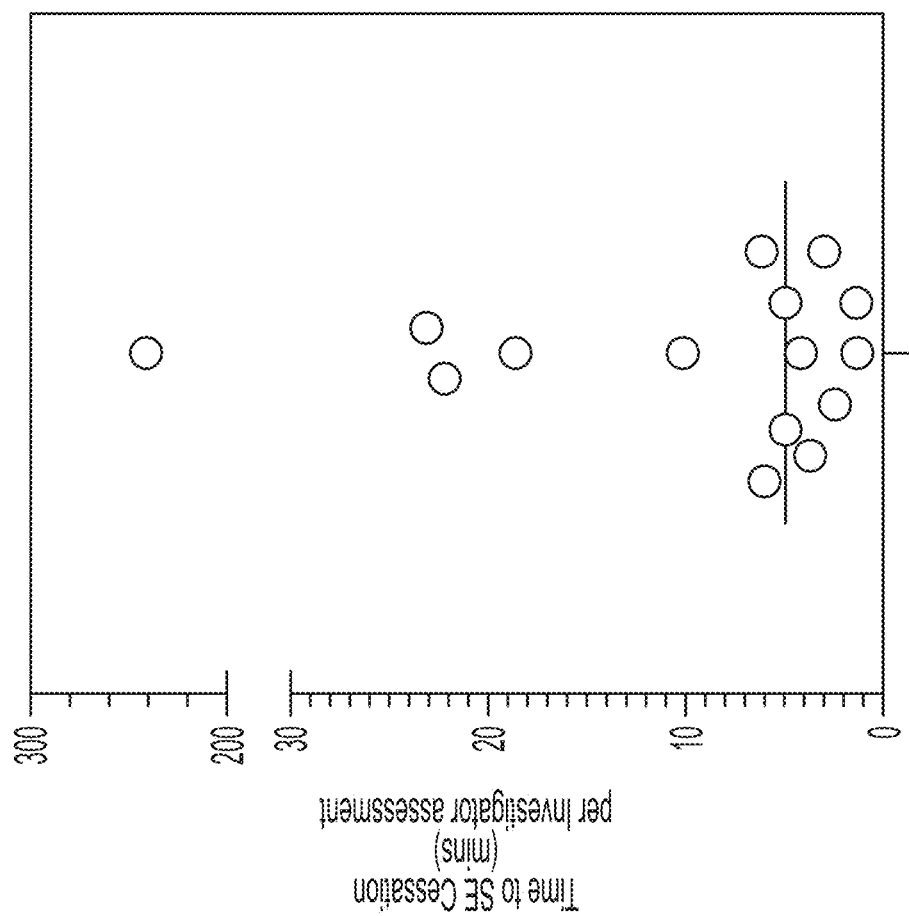
FIG. 12 is a graph showing the time to SE cessation in low, medium, and high dose groups. The graph shows that the median for SE cessation in all dose groups was 5 minutes.
Figure 13A:
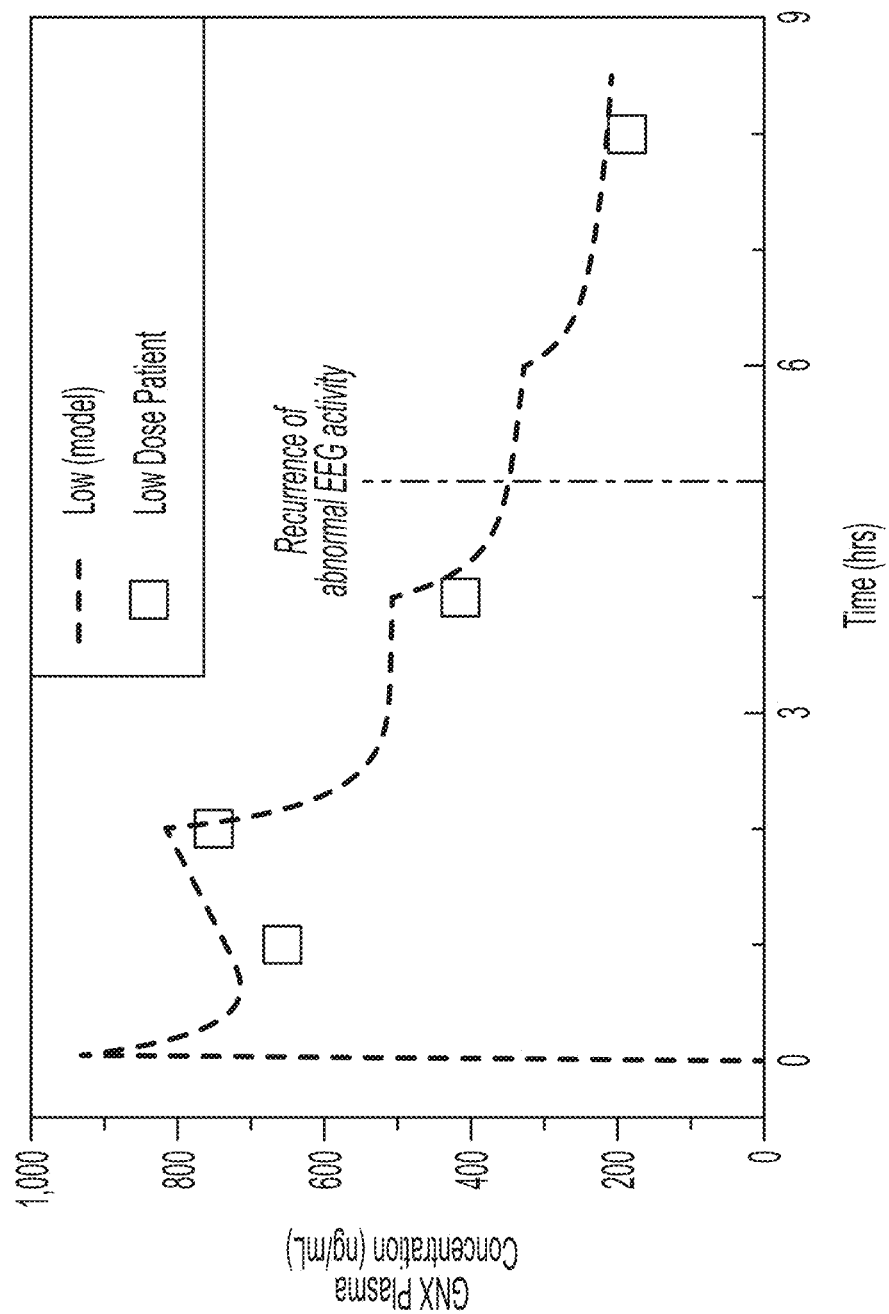
FIG. 13A is a graph showing the PK/PD relationship and rationale for the target dose.
Figure 13D:
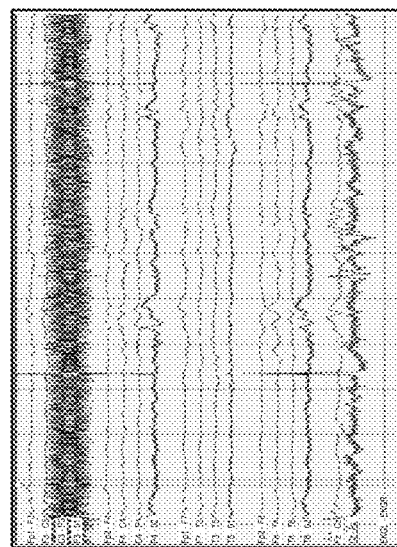
FIGS. 13B-13D are exemplary electroencephalograms (EEG) showing that acute maintenance of ganaxolone plasma concentrations ≥500 ng/mL resulted in improved seizure control on EEG.
Figure 13C:
Figure 13B:
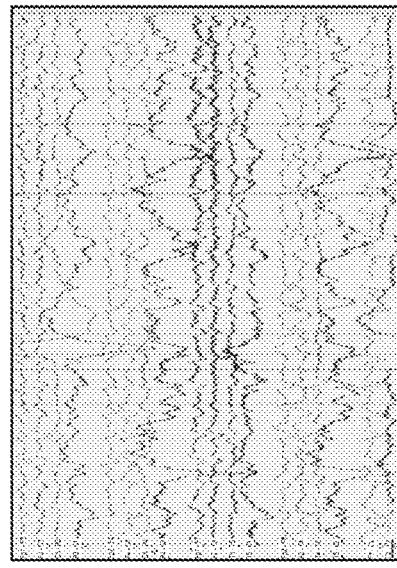

Median time to SE cessation was 5 minutes from initiation of GNX treatment (n=15 evaluable patients). FIG. 12. In 14 out of 15 patients, SE cessation was achieved in <30 min.

Figure 15:
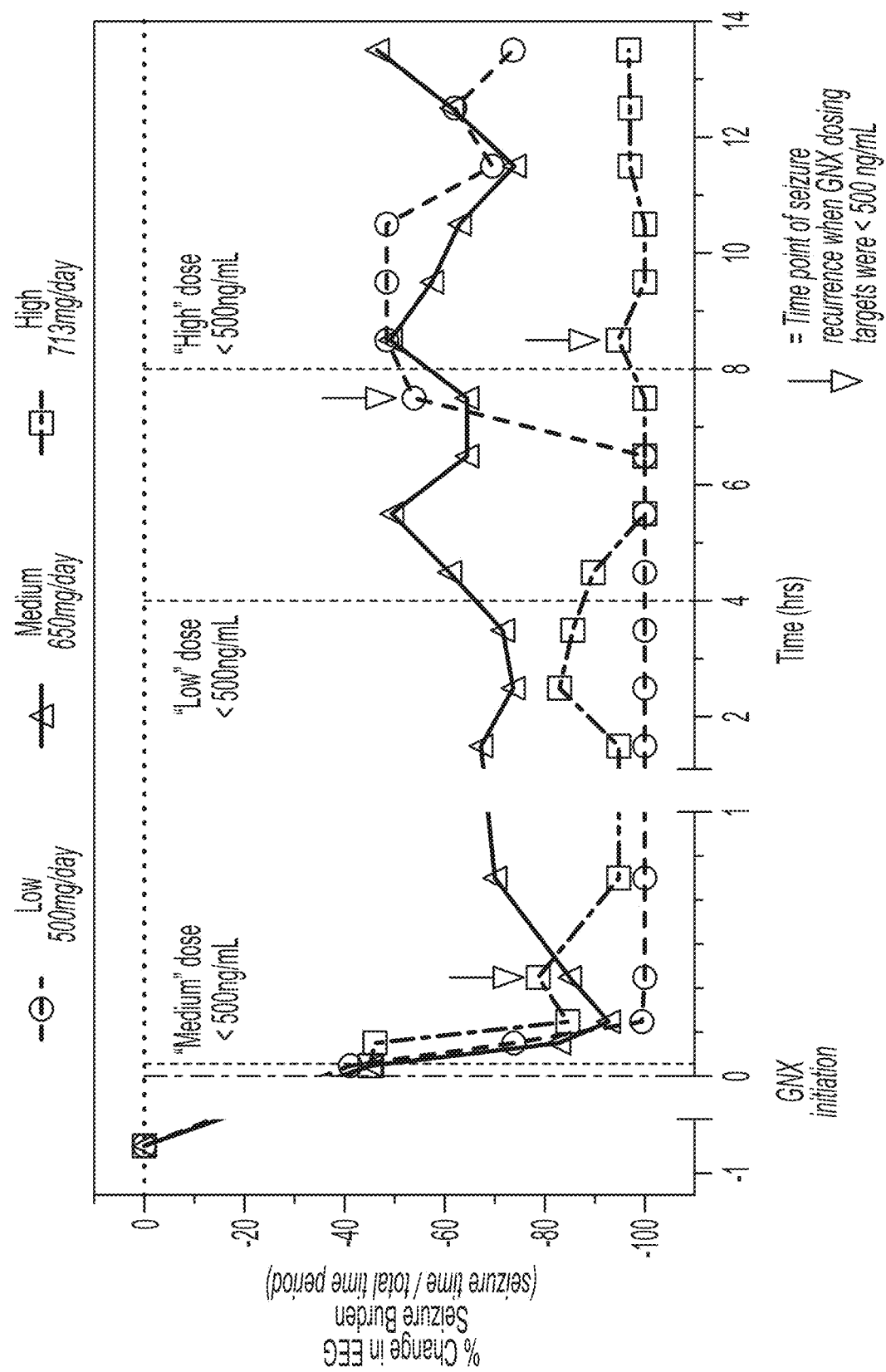
FIG. 15 is a graph depicting percent change in EEG seizure burden in refractory SE patients administered IV ganaxolone in low, medium, and high dosing cohorts.

IV GNX achieved a rapid and dose-dependent sustained reduction in EEG seizure burden in 15 evaluable patients (FIG. 15).

Acute maintenance of GNX plasma concentrations >500 ng/mL was associated with improved seizure control on EEG (FIGS. 13A-13D).

GNX infusion was generally well-tolerated in this patient population and the safety profile of GNX was consistent with its GABAergic mechanism of action. SAEs (severe sedation) assessed as related to GNX treatment were reported in 2 participants that led to early GNX discontinuation. These 2 cases occurred in participants who were concomitantly receiving several other CNS depressant medications and did not occur at the time of the highest predicted plasma concentrations of GNX.

The invention claimed is:

1. A method for treating status epilepticus (SE), comprising administering to a subject in need thereof:
   a) an intravenous bolus of ganaxolone in an amount sufficient to suppress SE, and
   b) a continuous intravenous infusion of ganaxolone in an amount sufficient for continued SE suppression, wherein the continuous intravenous infusion i) is initiated periprocedurally with the intravenous bolus, ii) is administered for a treatment period of about 24 hours to about 36 hours and the amount of ganaxolone infused is decreased at least twice during the treatment period, and iii) is intended to produce a ganaxolone plasma concentration in the subject of at least about 500 ng/ml to about 1000 ng/ml for at least about 8 hours to about 12 hours.

2. The method of claim 1, wherein the intravenous bolus and the continuous intravenous infusion does not result in anesthesia of the subject.

3. The method of claim 1, wherein the intravenous bolus produces a ganaxolone plasma concentration in the subject of at least about 500 ng/ml to about 1000 ng/ml.

4. The method of claim 1, wherein the amount of ganaxolone administered to the subject per hour by continuous intravenous infusion is decreased over a period of about 24 hours from the initiation of the continuous intravenous infusion.

5. The method of claim 1, wherein the amount of ganaxolone administered to the subject per hour by continuous intravenous infusion is first decreased about 2 hours after the initiation of the continuous intravenous infusion.

6. The method of claim 5, wherein the amount of ganaxolone administered to the subject per hour by continuous intravenous infusion is first decreased by about 50%, relative to the amount administered per hour at the initiation of the continuous intravenous infusion, about 2 hours after the initiation of the continuous intravenous infusion.

7. The method of claim 5, wherein the amount of ganaxolone administered to the subject per hour by continuous intravenous infusion is decreased a second time about 10 hours to about 14 hours after the initiation of the continuous intravenous infusion.

8. The method of claim 7, wherein the amount of ganaxolone administered to the subject per hour by continuous intravenous infusion is decreased by about 75%, relative to the amount administered per hour at the initiation of the continuous intravenous infusion, about 10 hours to about 14 hours after the initiation of the continuous intravenous infusion.

9. The method of claim 1, wherein the amount of ganaxolone administered to the subject per hour by continuous intravenous infusion is first decreased about 2 hours after the initiation of the continuous intravenous infusion, and then decreased again about 10 hours to about 14 hours after the initiation of the continuous intravenous infusion.

10. The method of claim 9, wherein the amount of ganaxolone administered to the subject per hour by continuous intravenous infusion is decreased by about 50%, relative to the amount administered per hour by the initiation of the continuous intravenous infusion, about 2 hours after the initiation of the continuous infusion, and then by about 75%, relative to the amount administered per hour at the initiation of the continuous intravenous infusion, about 10 hours to about 14 hours after the initiation of the continuous infusion.

11. The method of claim 1, wherein the amount of ganaxolone administered to the subject per hour by continuous intravenous infusion is increased after about 24 hours from the initiation of the continuous intravenous infusion.

12. The method of claim 11, wherein the amount of ganaxolone administered to the subject per hour by continuous intravenous infusion is increased by up to about 45%, relative to the amount administered per hour starting after about 24 hours after initiation of the continuous intravenous infusion.

13. The method of claim 11, wherein the amount of ganaxolone administered to the subject per hour by continuous intravenous infusion is increased for a period up to about 12 hours.

14. The method of claim 1, further comprising c) continuing to administer the continuous intravenous infusion for a taper period following the treatment period.

15. The method of claim 1, wherein the taper period starts at about 36 hours from the initiation of the continuous intravenous infusion.

16. The method of claim 14, wherein the amount of ganaxolone administered to the subject per hour by continuous intravenous infusion during the taper period is reduce by about one third about every 4 hours.

17. The method of claim 1, wherein the intravenous bolus comprises about 5 mg to about 40 mg of ganaxolone.

18. The method of claim 1, wherein the intravenous bolus is administered to the subject for about 1 minute to about 5 minutes.

19. The method of claim 1, wherein about 20 mg of ganaxolone per hour to about 80 mg of ganaxolone per hour are infused into the subject during the continuous infusion treatment period.

20. The method of claim 1, wherein about 80 mg of ganaxolone per hour are infused into the subject at the initiation of the continuous intravenous infusion.

21. The method of claim 1, wherein the amount of ganaxolone infused into the subject by the continuous intravenous infusion is decreased to about 40 mg ganaxolone per hour and then to about 20 mg ganaxolone per hour during the treatment period.

22. The method of claim 1, wherein about 80 mg of ganaxolone per hour is administered to the subject by the continuous intravenous infusion from initiation and for at least about 2 hours thereafter.

23. The method of claim 1, wherein about 40 mg of ganaxolone per hour is administered to the subject by continuous intravenous infusion starting about 2 hours after initiation and for about 6 hours to about 10 hours thereafter.

24. The method of claim 1, wherein about 20 mg of ganaxolone per hour is administered to the subject by continuous intravenous infusion starting about 12 hours after initiation and for about 12 hours to about 24 hours thereafter.

25. The method of claim 1, wherein the amount of ganaxolone infused into the subject by continuous intravenous infusion is increased up to about 45 mg of ganaxolone per hour starting about 24 hours after initiation and for up to about 12 hours thereafter.

26. The method of claim 25, wherein the amount of ganaxolone administered to the subject by continuous intravenous infusion does not exceed 45 mg ganaxolone per hour.

* * * * *